United States Patent [19]
Müller et al.

[11] Patent Number: 5,493,593
[45] Date of Patent: Feb. 20, 1996

[54] TILTED DETECTOR MICROSCOPY IN COMPUTERIZED TOMOGRAPHY

[75] Inventors: Martin Müller, Ludwigsburg, Germany; Gonzalo R. Arce, Wilmington, Del.

[73] Assignee: University of Delaware, Newark, Del.

[21] Appl. No.: 312,719

[22] Filed: Sep. 27, 1994

[51] Int. Cl.$^6$ ................................................. A61B 6/03
[52] U.S. Cl. ....................................... 378/19; 378/4
[58] Field of Search .................... 378/4, 11, 17, 378/19, 20

[56]  References Cited

U.S. PATENT DOCUMENTS

| | | | |
|---|---|---|---|
| 4,176,279 | 11/1979 | Schwierz et al. | 378/19 X |
| 4,206,362 | 6/1980 | Bagby | 250/445 |
| 4,345,158 | 8/1982 | Pfeiler et al. | 378/5 |
| 4,417,354 | 11/1983 | Pfeiler | 378/19 |
| 4,637,040 | 1/1987 | Sohual et al. | 378/19 X |
| 4,694,399 | 9/1987 | Tan et al. | 364/414 |

Primary Examiner—David P. Porta
Attorney, Agent, or Firm—Connolly & Hutz

[57] ABSTRACT

The present invention relates to a method and setup for providing high resolution CT images at a low cost. The method utilizes a modified version of the standard CT setup wherein the radiation receiver (e.g., a detector(s)) is tilted with respect to an axis perpendicular to the plane of fan beam projection (e.g., when a fan shaped radiation beam is used). Moreover, to maximize the utilization of the radiation receiver and obtain the highest resolution in the final image, the radiation receiver is also shifted horizontally within the radiation beam.

9 Claims, 42 Drawing Sheets

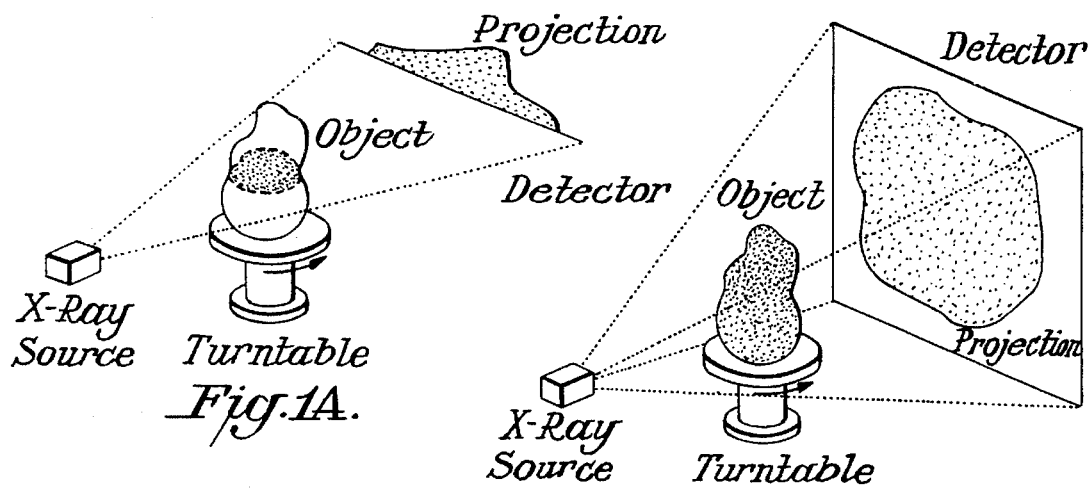
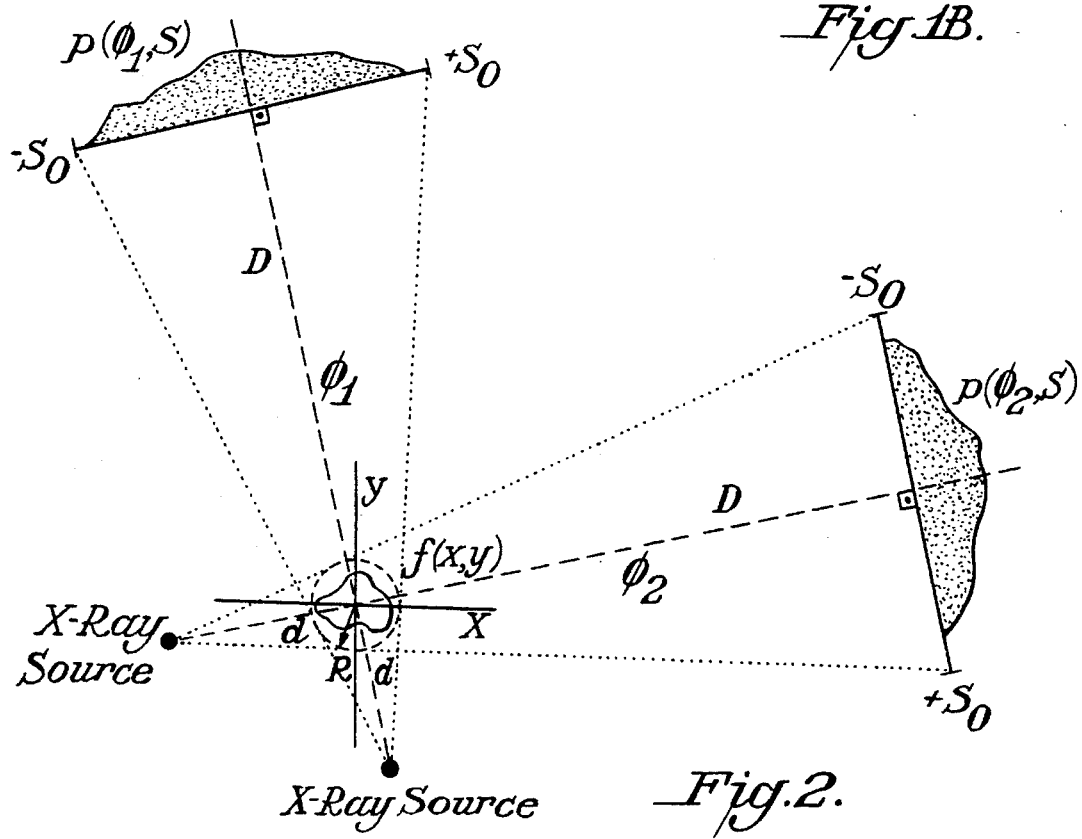

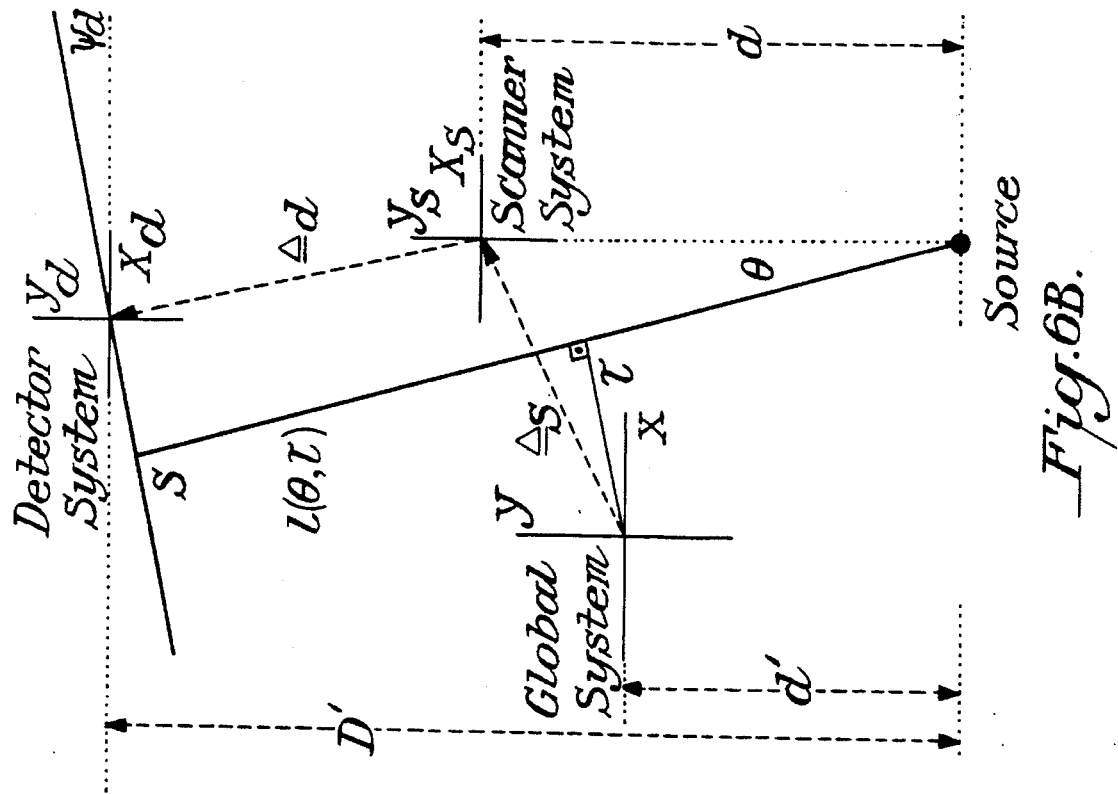
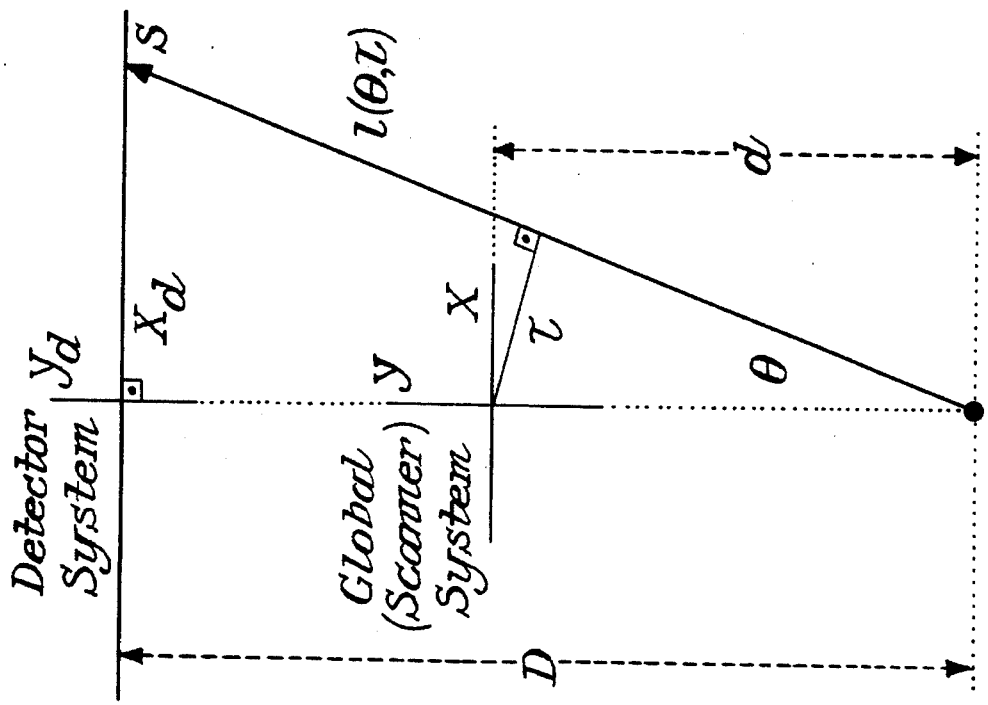
Fig.6B.
Fig.6A.

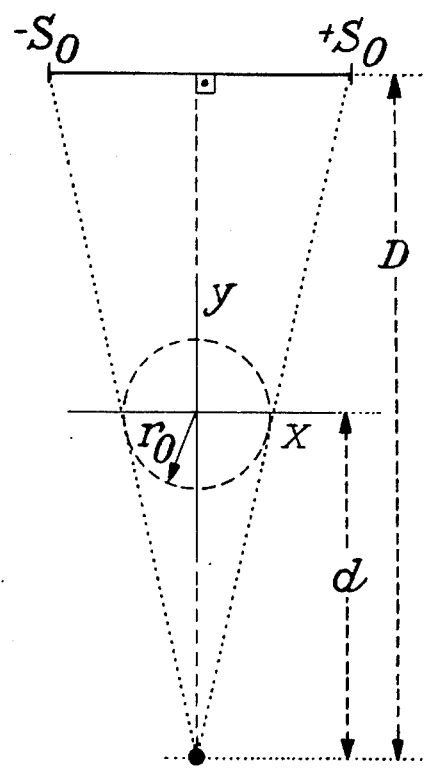
_Fig.12A._
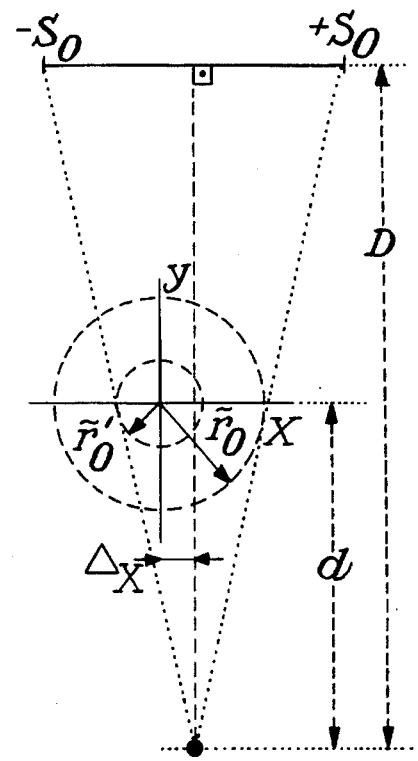
_Fig.12B._

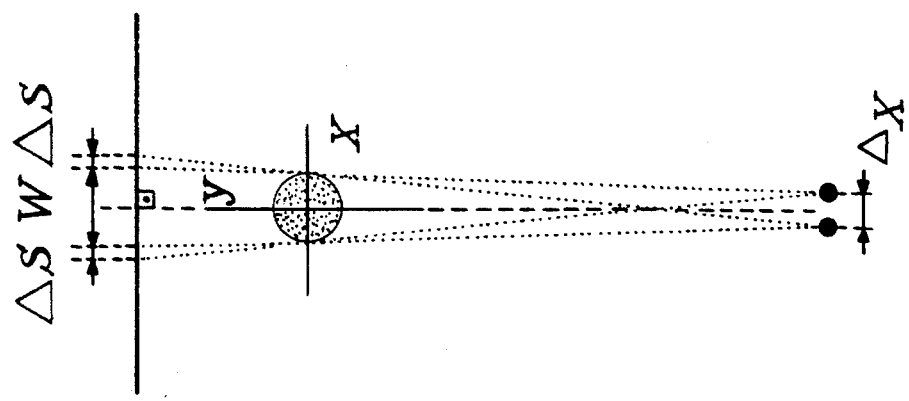
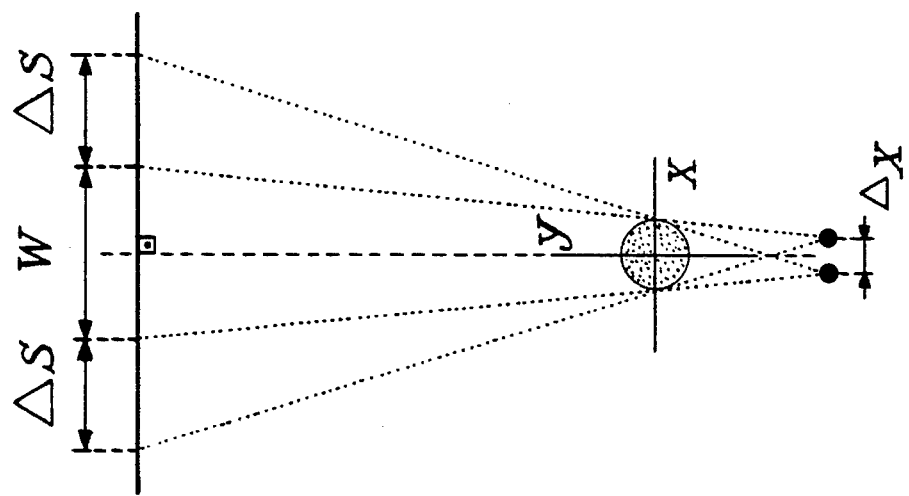
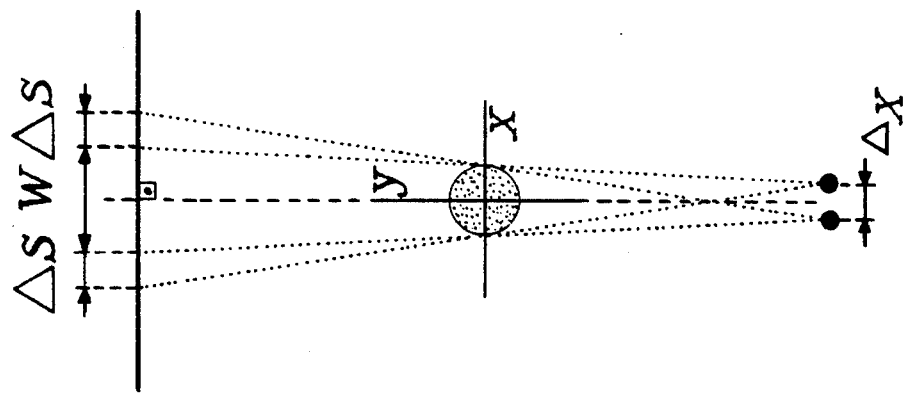

TILTED DETECTOR MICROSCOPY IN COMPUTERIZED TOMOGRAPHY

BRIEF DESCRIPTION OF THE INVENTION

The present invention relates to a method and setup for providing high resolution CT images at a low cost. The method utilizes a modified version of the standard CT setup wherein the radiation receiver (e.g., a detector(s)) is tilted with respect to an axis perpendicular to the plane of fan beam projection (e.g., when a fan shaped radiation beam is used). Moreover, to maximize the utilization of the radiation receiver and obtain the highest resolution in the final image, the radiation receiver is also shifted horizontally within the radiation beam.

BACKGROUND OF THE INVENTION

Computerized tomography (CT) is an advanced method of nondestructive evaluation (NDE) employed in medical imaging, material science, quality assurance etc. An image is recovered from projection data obtained with the CT scanner through a reconstruction algorithm. The CT scanner consists of a source (usually emitting X-rays), a detector, and a turntable positioned between the source and the detector. The object to be investigated is placed onto the turntable and is rotated 360° while the projection data (i.e., the X-ray shadow) is recorded. FIGS. 1a and 1b illustrate the scanner setup for 2D and 3D CT. While in medical imaging the scanner revolves around the patient, in industrial imaging the investigated object is rotated on the turntable. The projection data is recorded with the resolution made available by the employed detector.

The resolution of the detector is limited due to technical reasons, where the cost of the detector grows with increasing resolution. However, investigation of tiny objects requires projections with a high resolution, since projections of low resolution result in blurred images. Besides using high resolution detectors, existing methods of CT microscopy further increase the effective beam spread by moving the object/turntable closer to the point source as depicted in FIG. 2 where the detector is perpendicular to the center X-ray beam. The reconstruction algorithms become inherently instable for reconstruction close to the source, and tend to greatly magnify noise and other artifacts (see FIG. 5a and 5b).

The image of the object is recovered from its projections with a reconstruction algorithm. The standard fan (2D) and cone (3D) beam convolution backprojection algorithms most commonly used in practice require the central ray emitted by the source which intersects with the axis of object rotation to be perpendicularly incident on the detector center. Any deviation from this required geometry results in images that are at least degraded and sometimes completely useless.

Some methods of high resolution CT have been developed to date. These methods are either based on the use of expensive high resolution detectors or close proximity CT (moving the object close to the source) using standard reconstruction algorithms, or sole software solutions preprocessing the projection data to better utilize the inherent resolution information. A hybrid method combining a modified projection geometry (hardware) with a reconstruction algorithm adapted to the new geometry (software) has the potential to outperform any of the previously found methods.

The method of the present invention has many uses. For example, the method can be used in related techniques such as ultrasonic inspection, diffractive tomography, impedance tomography, MRI scans, medical imaging, etc. One of the most desirable uses for computerized tomography is in the field of material science. For example, it is very difficult to perform non-destructive microstructural analysis and quality review on composite materials. These materials are being used in an increasing number of applications and have already become the preferred material for high-performance structural components in the aerospace industry. A similar development can now be observed in the automotive industry, where composite materials are expected to replace any traditional materials due to superior strength-to-weight ratio, stress behavior, life-expectation, manufacturability, etc. For the further development of composites and their successful integration in the manufacturing process, the availability of high-quality methods for testing, evaluation, and verification of these materials, especially their microstructure, is imperative. CT is an investigative tool providing an advanced method of material testing and evaluation. However, the presently available techniques for performing CT are time consuming and, to achieve the necessary high resolution, expensive detectors are required. Therefore, to provide an economical procedure for high resolution microtomographic investigation of materials, a new method of performing CT had to be developed. Moreover, due to the high cost of high resolution detectors, it was clear that standard detectors would have to be employed.

SUMMARY OF THE INVENTION

An object of the present invention was to provide high resolution CT systems at a low cost. This object was achieved by the method of the present invention wherein the detector is tilted with respect to an axis perpendicular to the plane of fan beam projection. Moreover, to maximize the utilization of the detector and obtain the highest resolution, the detector is also shifted horizontally within the radiation beam.

The method of the present invention utilizes a tilted detector to spread the projection of a tiny object over a large portion of the detector. The full resolution of the detector may be utilized by magnifying/stretching the projection horizontally (see FIG. 3). Note that tilting the detector results in an asymmetric effective range of the detector on the left and right side of the tilt axis. The projection of an object circumscribed by the circle depicting the field of view are delimited by the extreme rays being tangents of this circle (see FIG. 3). The optimal utilization of the detector is thus achieved by tilting ($\Psi_d$) and shifting ($\Delta_x$) the detector, as depicted in FIG. 3. It is important to note that the shift and tilt parameters $\Psi_d$ and $\Delta_x$ have to be carefully chosen so as to achieve the maximum resolution enhancement with the employed detector. Also, the projection geometry substantially differs from the previously described standard geometry, and thus requires appropriate reconstruction methods. FIG. 4 depicts the resolution enhancement with increasing detector tilt angle.

A straightforward method of reconstruction from projection data obtained with a tilted detector is the rebinning of the data to form virtual projection data which may be reconstructed with a standard algorithm. Any rebinning or resorting of projection data, however, involves interpolation between ray paths (i.e., a ray path somewhere "in-between" two measured ray paths may need to be synthesized to create a virtual projection simulating the desired standard projection geometry). The inevitable loss of resolution due to interpolation at least partially cancels the gain in resolution from tilting, and must be avoided.

It is possible to modify the reconstruction algorithm such that projection data recorded in non-standard geometries may be reconstructed. Provided the geometrical parameters are precisely known (e.g., detector tilt and shift) such an algorithm may be used to reconstruct from data obtained with a tilted detector without the unwanted loss of resolution due to data preprocessing.

Should the precise geometrical parameters be unobtainable, such an algorithm could be used as a means of "refocusing" the reconstructed image by software. In a process of successive approximation the reconstruction resolution may be continually improved by perturbating the geometrical parameters driving the algorithm. Once the reconstructed image is free of blurring and other related artifacts, the precise parameters have been determined.

The inventors have developed a hybrid method combining the above described modifications in the projection geometry and the image reconstruction with a "generalized" algorithm capable of processing data obtained in arbitrary projection geometries. While the reconstruction from tilted detector projections is clearly the main applications the "focusing-by-software" feature of the algorithm due to the added degrees of freedom in general reduces costs on the hardware side by allowing a certain "sloppiness" in the mechanical setups.

It is important to note that only the combination of tilting/shifting the detector and application of the generalized algorithm result in the desired resolution enhancement. The generalized reconstruction algorithm is an integral component of the method of the present invention.

For the purposes of the present application, a CT scanner is defined as a device which consists of a source (usually emitting X-rays), a detector, and a mechanical turntable positioned in-between the source and detector, on which the object to be investigated is placed. A standard scanner setup would include all of these components.

The method of the present invention requires the use of a device which tilts the detector. A low precision tilting device may be used if the focus-by-software feature of the generalized algorithm is employed. The generalized reconstruction algorithm must be implemented on the computer performing the image processing. The algorithm has been implemented and speed optimized by the inventors. The runtime of the generalized algorithm amounts to approx. 120% of that of a standard algorithm.

As discussed earlier, the methods that are currently being used in CT microscopy either employ detectors with sufficiently high resolution, or move the object very close to the point source so as to achieve a sufficient increase in the beam spread, or a combination of both. In addition, methods optimizing the utilization of the resolution inherent in the projection data have been proposed (these methods, however, have limited impact and do not improve the resolution in the projection data). The currently available methods usually involve expensive equipment, and the recovered images are often degraded due to reconstruction artifacts. The present invention utilizes existing equipment with a minor addition in hardware while reducing reconstruction artifacts.

A method similar in hardware to the above-described method is discussed in U.S. Pat. No. 4,417,354 (M. Pfeiler, Siemens AG, Germany). The patent teaches that the resolution of an X-ray image may be increased by recording it with a tilted detector. A number of variations of tilted detectors are presented. A horizontal shift is used in the method (column 3, lines 21–22), but no clear statement is made for what purpose ("... permits additional influencing of the image resolution...", column 3, lines 23–34). The patent teaches that the radius of the scanned subject circle shrinks due to the detector tilt (column 3, lines 11–13), but does not mention the asymmetries and the substantial loss of detector range if the tilted detector is not horizontally displaced so as to reinstate a symmetric effective detector range. No statement is made as to how an image is formed from the recorded data The patent teaches "... a computer which...", "... computes the attenuation values of specific image points...", and the "... image is reproduced on a video display unit..." (column 2, lines 40–48). It appears that this patent concerns recording resolution enhanced projection data with tilted detectors in a number of variations and with a number of added degrees of freedom (shifts). It also appears that a method as to how to process the data and utilize the gained resolution was not known at the time, since no clear statement is made on the image formation. Thus, this patent is clearly directed to a method of increasing the resolution in radiograms, which are the X-ray shadows of the investigated object. A description of how to obtain a tomogram from the stretched projection data is not given.

Standard X-ray detectors are composed of an intensifying (phosphor) screen converting the incident X-rays into visible light, and an array of sensors recording the visible image produced by the intensifying screen. Due to quantum-optical interaction between phosphor elements, the resolution of the intensifying screen is limited. When the intensifying screen is tilted, X-ray photons hit the screen at approx. the tilt angle, which results in increased blurring and partially cancels the gain in resolution due to the projection stretching.

However, new developments in intensifying screens have resulted in the application of phosphor arrays, which are a honeycombed grid of optically isolated phosphor microtubes. This approach avoids quantum-optical interactions and achieves resolution in the lower micrometer ranges. Since phosphor arrays consist of isolated phosphor elements, their performance with X-rays which hit the screen at an angle is superior to standard X-ray intensifying screens. Therefore, in a preferred embodiment of the present invention, the X-ray intensifying screens contain phosphor arrays.

BRIEF DESCRIPTION OF THE DRAWINGS

FIG. 1 shows the scanner setup for 2D and 3D CT. The object is placed on the turntable, which is positioned between the source and the detector. The projection data is recorded while the object is rotated 360°. FIG. 1(a) shows 2D CT. The detector has the form of a straight line, recording the fan beam projection of a two-dimensional slice of the object. FIG. 1(b) shows 3D CT. The detector has the form of a plane, recording the cone beam projection of the entire object.

FIG. 2 is a diagram (view from above) of a 2D CT system wherein resolution enhancement is obtained by moving the object close to the source. The object inside the desired artifact-free zone of radius R is projected.

FIG. 6 shows two diagrams (view from above) illustrating the fan beam geometry of standard and universal scanners. The global system (x,y) represents the center of rotation. A ray is completely described by its ray displacement $\tau$ and ray angle $\phi$ measured with respect to the global system. In (a), the standard fan beam scanner geometry is shown. The global system is identical with the scanner system. The detector system is horizontally aligned. In (b), the Universal fan beam scanner geometry is shown. The scanner system is displaced by vector $\Delta_s$ relative to the global system. The detector system is displaced by vector $\Delta_d$ relative to the scanner system and tilted by angle $\psi_d$.

FIG. 12 shows two diagrams (view from above) which illustrate the geometry of standard and partially redundant fan beam projections. Parameter $\Delta_x$ denotes the horizontal scanner displacement. The dashed circles of radii $r_o$ and $\tilde{r}_o$ delimit the artifact-free zones of the standard and partially redundant scanners respectively. In (a), a standard projection is shown. In (b), a partially redundant projection is shown. The inner dashed circle of radius $\tilde{r}'_o$ delimits the zone of redundant reconstruction.

FIG. 19 shows three diagrams (view from above) illustrating penumbral broadening in tomographic projections. Parameter $\Delta_s$ denotes the penumbral broadening measure. 19(a) shows the object centered between the source and detector. 19(b) shows the object close to the source. The penumbral blur grows overproportionately. 19(c) shows the object close to the detector. The penumbral blur is reduced.

DETAILED DESCRIPTION OF THE INVENTION

Section 1 - Background

Figure 3:
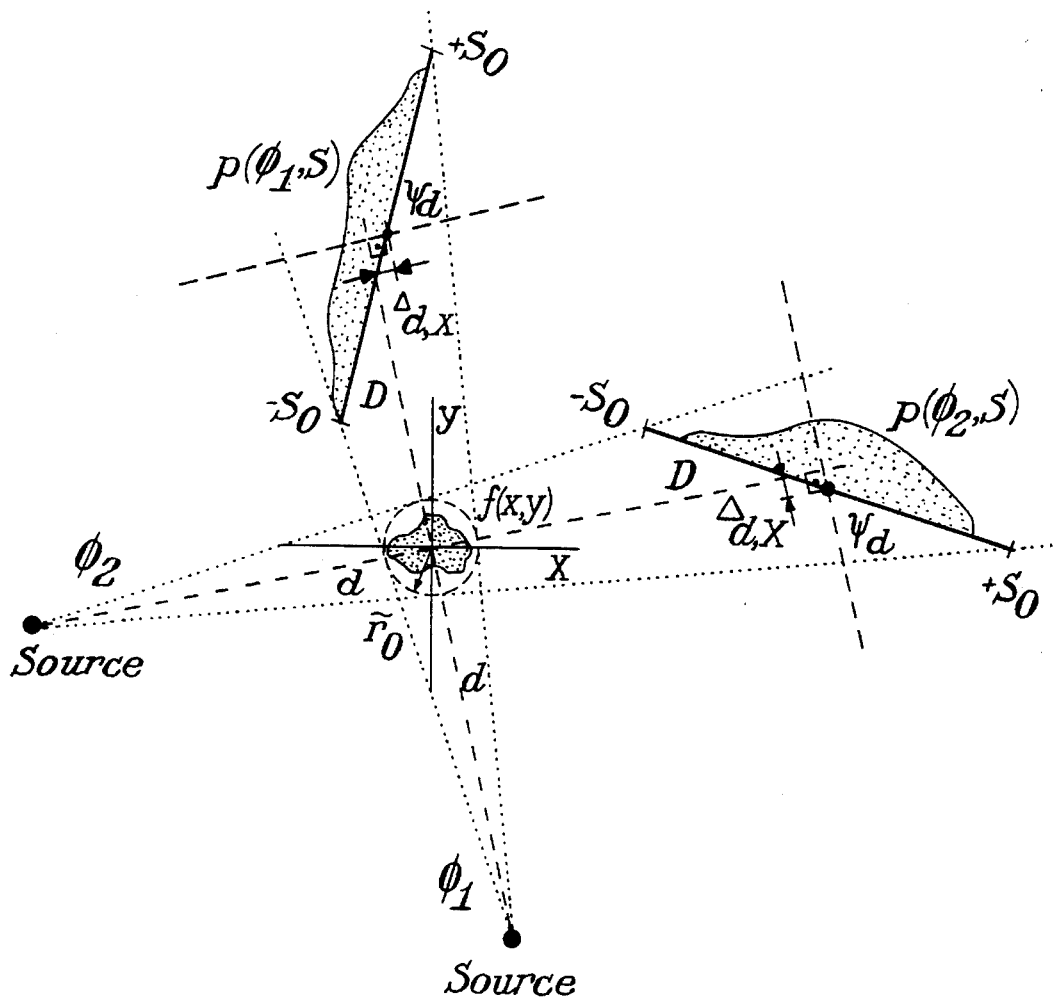
FIG. 3 is a diagram (view from above) of a 2D CT system wherein resolution enhancement is obtained by detector tilting. The object inside the desired artifact-free zone of radius R is projected. The detector of size $2s_o$ is tilted by angle $\psi$. To further optimize detector utilization, the detector tilt axis is shifted from the center ray by $\Delta_{d,x}$. Note that the detector shift can be substituted by an equivalent constant horizontal scanner shift.
Figure 4A:
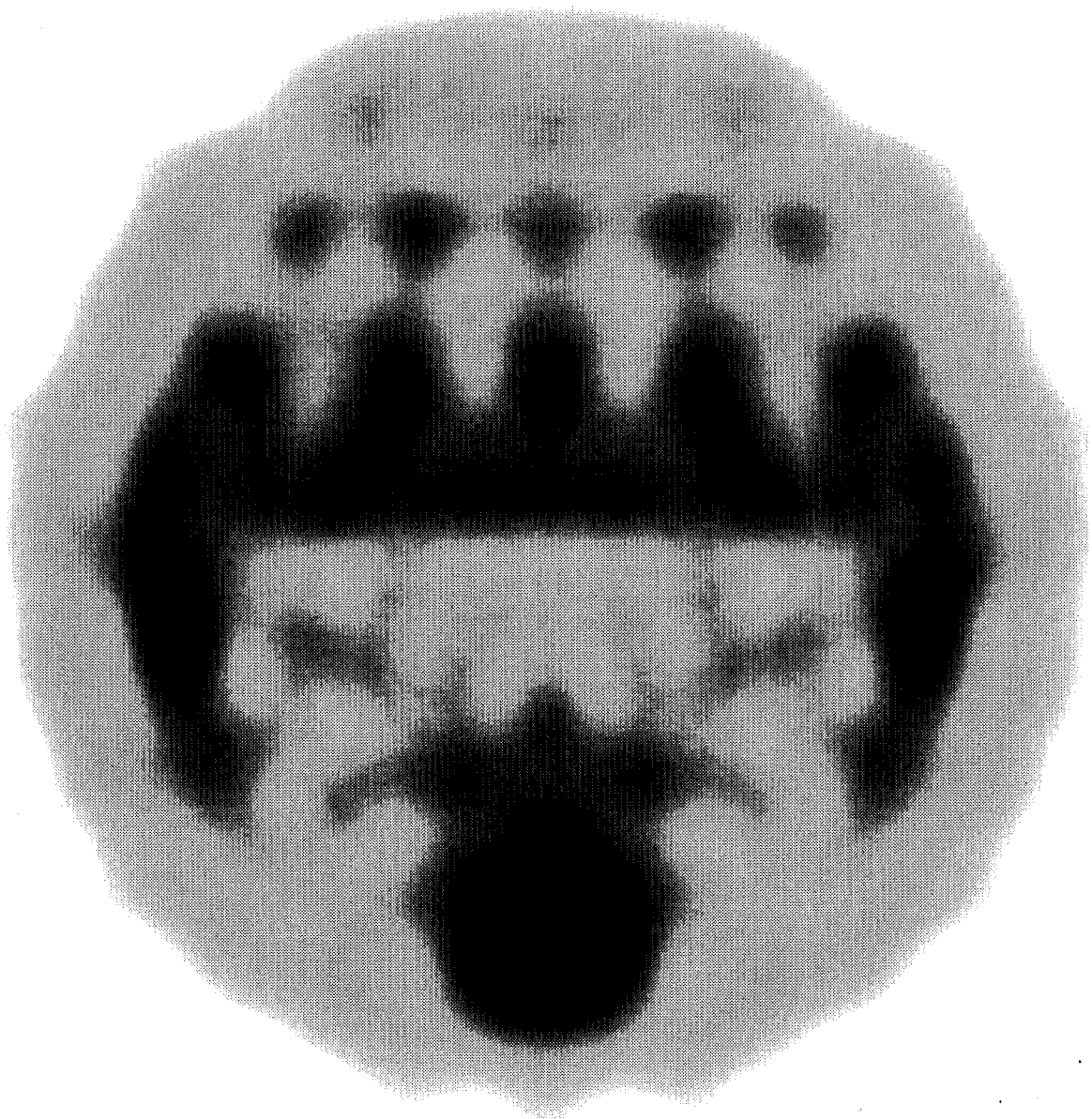
FIG. 4 shows reconstructions from tilted sets of projections. Projection parameters: source-to-detector distance D=1000 mm, collinear detector of size L=250 mm with $N_s$=601 equally spaced sensors, $N_\phi$=601 projection angles. Object diameter $\phi$=2 mm. In (a), the detector is not tilted (M=1). The reconstructed image does not allow any interpretation. In (b), the detector is tilted by 60° (M=2). The features of the object become more clearly outlined. In (c), the detector is tilted by 78° (M=5). The reconstructed image begins to reveal details of the internal structure of the object. In (d), the detector is tilted by 88° (M=32). The object is precisely reconstructed with high resolution and detail.
Figure 4B:
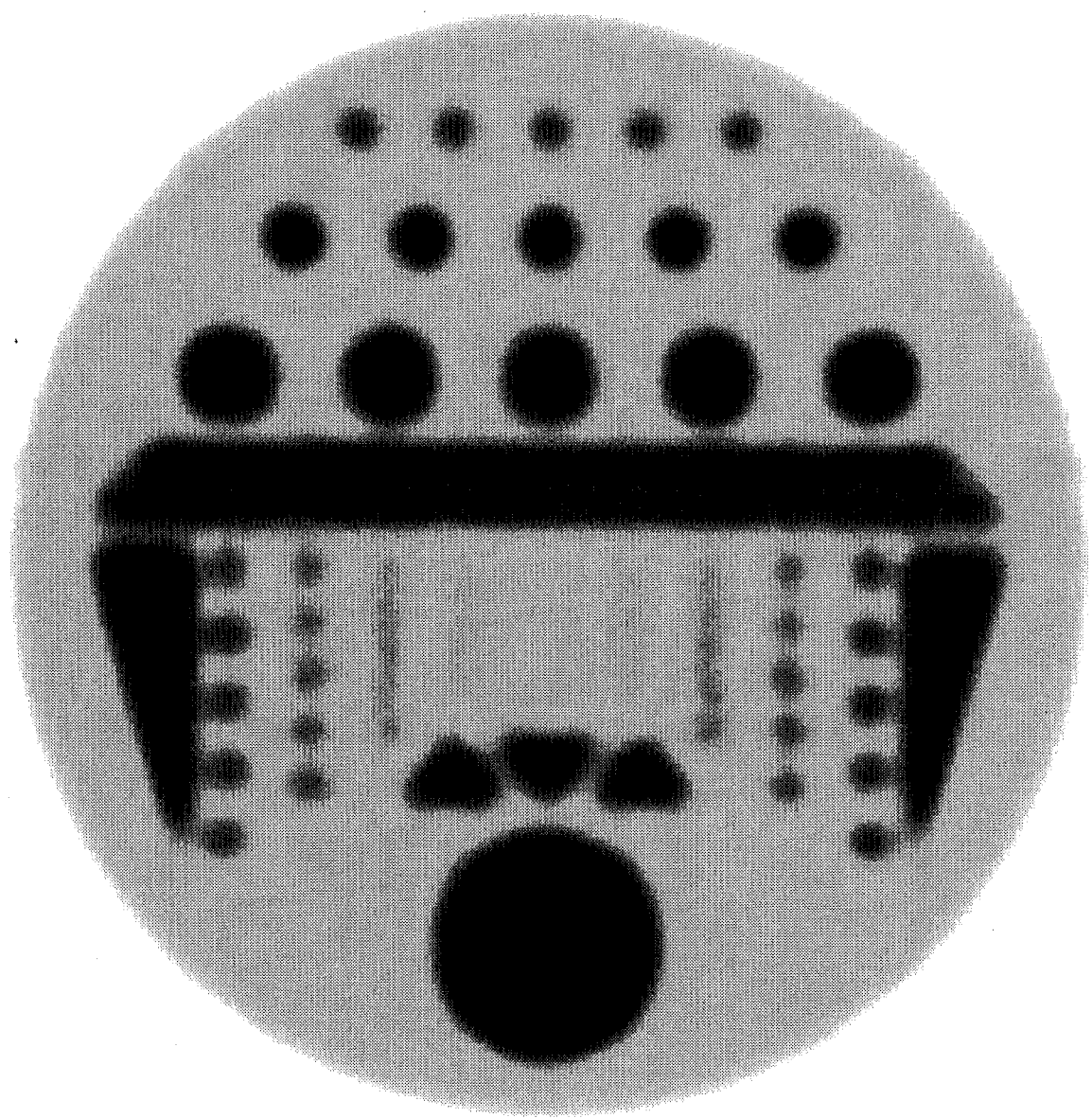
Figure 4C:
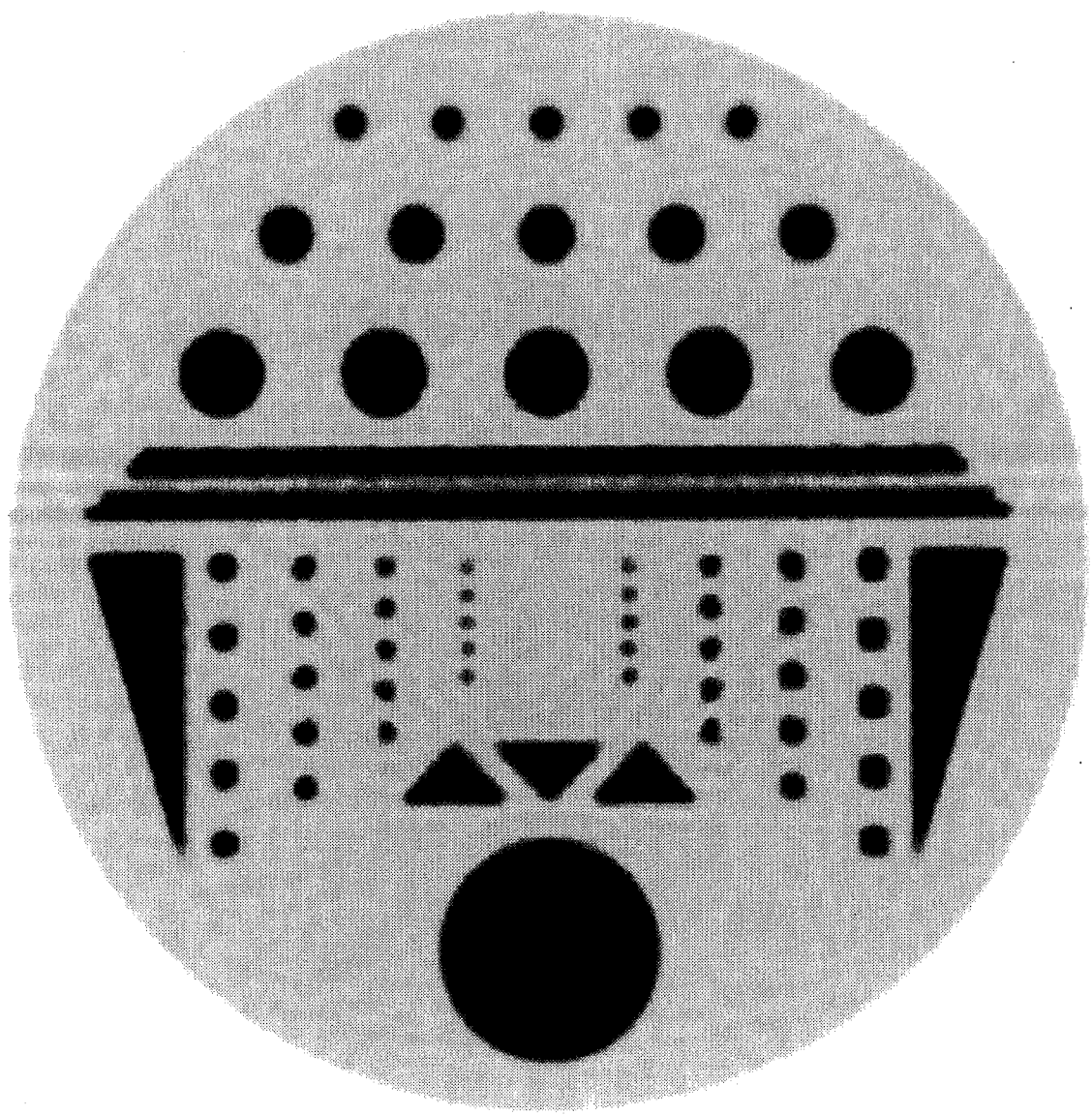
Figure 4D:
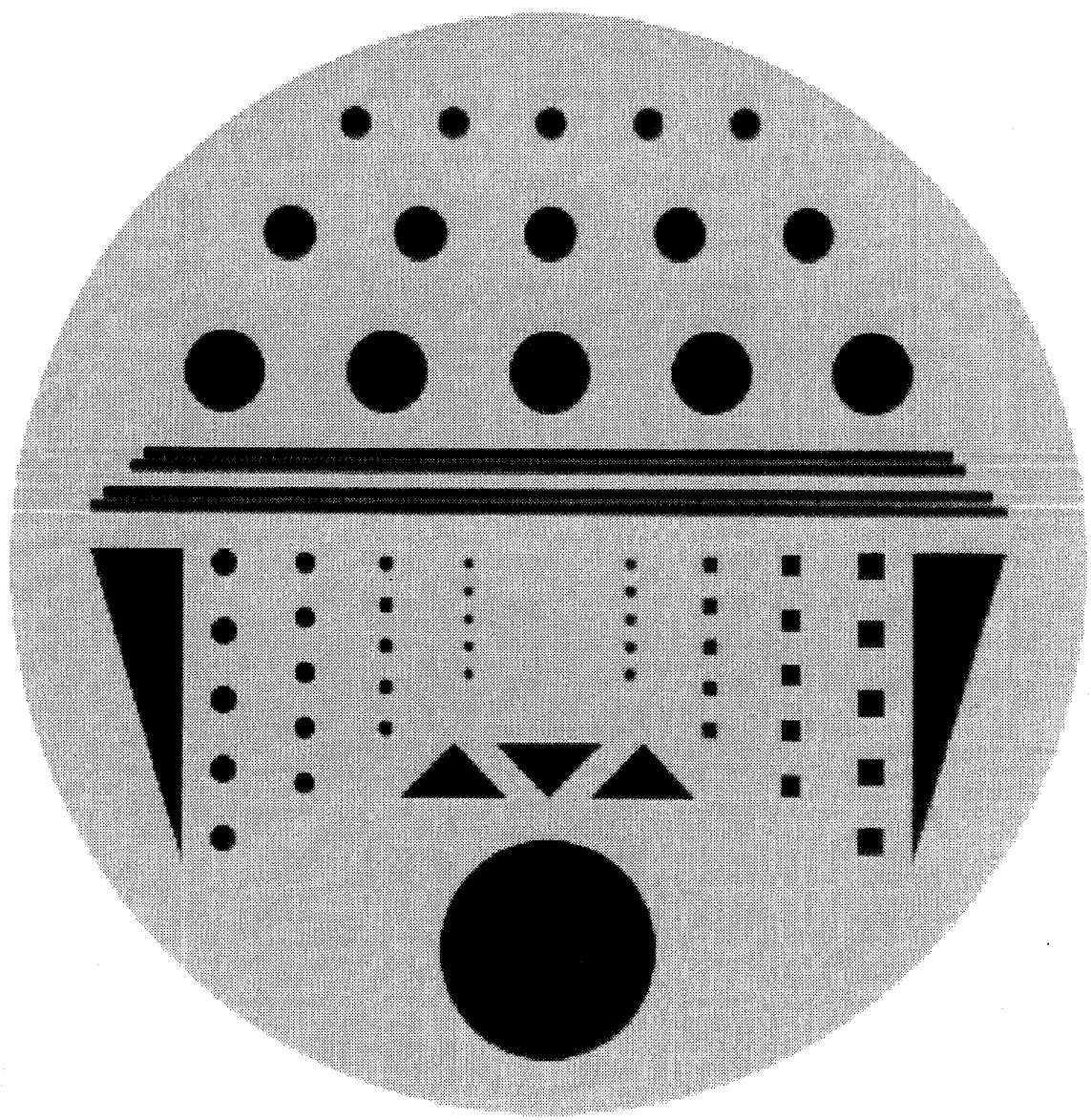

Tomography is the method of non-invasively investigating internal structures of objects with information obtained solely from the outside of the objects. The mathematical framework describing the determination of functions from their projections was first researched by Radon in 1917 [J. Radon; "Über the Bestimmung von Funktionen durch ihre Integralwerte längs gewisser Mannigfaltigkeiten", *Berlin, SächischeAkademie der Wissenschaften*, Vol. 29, 1917, pp. 262–279. Reprint in english language: "On the Determination of Functions From Their Integral Values Along Certain Manifolds", *IEEE Transactions on Medical Imaging*, Vol. 5, 1986, pp. 170–176.]. Although the tomographic principle was utilized in a number of early practical designs, the potential of tomography as an accurate imaging tool was not recognized until Hounsfield's invention of the computerized medical tomographic X-ray scanner in 1972 [G. N. Hounsfield; "A method of an apparatus for examination of a body by radiation such as x-ray or gamma radiation", U.K. Patent 1,283,915, 1972.]. With the advent of transistorized computers, computerized tomography (CT) became a subject of concentrated research activity, which in the past two decades with the development of projection schemes, data acquisition procedures, and reconstruction algorithms has made CT todays most powerful tool in non-destructive imaging.

The focus on practical issues of tomography in medicine and industry has resulted in a number of methods for reconstruction from non-ideal sets of projections such as limited angle [H. Stark; Image Recovery - Theory and Application, Academic Press, New York, 1987.], truncated [R. M. Lewitt and R. H. T. Bates; "Images Reconstruction from Projections" Parts I–IV, *Optik*, Wissenschaftliche Verlagsgesellschaft mbH Stuttgart, Vol. 50, 1978, pp. 19–33, 85–109, 189–204, 269–278., N. Srinivasa, V. Krishnan, K. R. Ramakrishnan, and K. Rajgopal; "Image Reconstruction from Truncated Projections: A Linear Prediction Approach", *IEEE Proceedings of the International Conference on Acoustics, Speech, and Signal Processing*, Tokyo, 1986., M. Müller, G. R. Arce, and R. A. Blake Jr.; "Truncated Projection Artifacts and Reconstruction in Computerized Tomography", submitted to *IEEE Transactions on Image Processing*., M. Müller and G. R. Arce, "The Cone Beam Algorithm and Synthetic Scanner Arrays in Three-Dimensional Computerized Tomography", technical report in the Department of Electrical Engineering at the University of Delaware, 1993.], coarsely sampled [W. Wagner; "Reconstructions from Restricted Region Scan Data - New Means to Reduce the Patient Dose", *IEEE Transactions on Nuclear Science*, Vol. 26, 1979, pp. 2866–2869.], or diffracted [M. Kaveh, M. Soumekh, and J. F. Greenleaf; "Signal Processing for Diffraction Tomography", *IEEE Transactions on Sonics and Ultrasonics*, Vol 31, 1984, pp. 230–239.] data. Today, tomography is not only being employed for qualitative evaluation in medical imaging, but is increasingly being used in industry as a measurement tool for quantitative non-destructive evaluation in material science, quality assurance, process control, etc. [H. E. Martz, S. G. Azevedo, J. M. Brase, K. E. Waltjen, and D. J. Schneberg; "Computed Tomography Systems and their Industrial Applications", *International Journal of Radiation Applications and Instrumentation*, Vol. 41, 1990, pp. 943–961. J. L. Ackerman and W. A. Ellington (Editors); Advanced Tomographic Imaging Methods For The Analysis Of Materials, Materials Research Society, Pittsburgh, 1991.]. Here, a much higher resolution and reconstruction fidelity is required, while in industrial applications parameters such as X-ray exposure and scanning time are usually not as critical as in medical tomography.

The increasing number of applications of precision CT in industry has led to a need for accurate determination and correction of mechanical misalignment in CT scanners. A number of statistically based methods determining the parameters of various projection geometries immediately from the projection data [G. T. Gullberg, B. M. W. Tsui, C. R. Crawford, and E. R. Edgerton; "Estimation of geometrical parameters for fan beam tomography", *Physics in Medicine & Biology*, Vol. 32, 1987, pp. 1581–1594., G. T. Gullberg, B. M. W. Tsui, C. R. Crawford, J. G. Ballard, and J. T. Hagius; "Estimation of geometrical parameters and collimator evaluation for cone beam tomography", *Medical Physics*, Vol. 17, 1990, pp. 264–272., S. G. Azevedo; "Calculation of the Rotational Centers in Computed Tomography Sinograms", *IEEE Transactions on Nuclear Science*, Vol. 37, 1990, pp. 1525–1540., H. P. Engel; "ZFOCUS: A Computer Algorithm for Optimizing Computed Tomography Pictures and Artifact Reduction", Materials Evalua [208ztion, Vol. 51, 1993, pp. 274–279.] have been proposed. Displacement of the source, object, or detector from their ideal position, for instance, result in blurred reconstructions, if not properly compensated. An ideal fan beam projection geometry requires the source, object, and detector center to be aligned, such that the center ray emitted by the source passing through the axis of object rotation is perpendicularly incident on the detector center. Non-ideal geometries deviate in one or more parameters from the ideal case. Algorithms efficiently accounting for simple mechanical misalignment have been developed [G. T. Gullberg, C. R. Crawford, and B. M. W. Tsui; "Reconstruction Algorithm for Fan Beam with a Displaced Center-of-rotation" *IEEE Transactions on medical Imaging*, Vol 5, 1986, pp. 23–29., C. R. Crawford and G. T. Gullberg; "Reconstruction for fan beam with an angular-dependent displaced center-of-rotation" *Medical Physics*, Vol. 15, 1985, pp. 67–71.]. For the development of a more general algorithm reconstructing in arbitrary projection geometries, the mathematics involved in modifying the standard fan beam algorithm have to be well understood. A series of two papers by Horn [B. K. P. Horn; "Denisty Reconstruction Using Arbitrary Ray-Sampling Schemes", *Proceedings of the IEEE*, Vol. 66, 1978, pp. 551–562., B. K. P. Horn; "Fan-Beam Reconstruction Methods", *Proceedings of the IEEE*, Vol. 67, 1979, pp. 1616–1623.] discuss the modification procedure and mathematical framework for reconstruction with arbitrary ray sampling schemes. In this application, we concentrate on the practically significant fan beam geometry with collinear detectors, where we obtain an universal reconstruction algorithm for arbitrary fan beam projection geometries.

Since the algorithm is designed to reconstruct from projections recorded in arbitrary scanner and detector translations and rotations, it allows artifact-free reconstruction in various non-ideal projection geometries such as reconstruction from projections with center-displaced sources, scanners, and detectors, if type and amount of the displacement are known. Statistical methods yielding the various geometrical fan beam parameters immediately from the projection data are available. A special case of center-displacement leads to the application of the new algorithm to single-sided tomography. Here, the projection data is non-redundant, and the radius of the artifact-free zone is doubled. Note that the artifact-free zone is delimited by the circle encompassing the object space resulting in complete and thus non-truncated projections (i.e., in a parallel beam scanner with a detector of width $2s_0$ we have an artifact-free zone of $r_o=s_o$). For single-sided projection, the scanner is shifted horizontally by a precise displacement, such that the fan illuminates only half the object (e.g., the leftmost beam crosses the axis of object rotation). Over the course of a full rotation the recorded data will be sufficient to reconstruct a precise image. An alternative method is to employ a center-displaced detector, such that we record only the right-hand side of the projection, for instance. As a mixed case we also introduce partially-redundant reconstruction, where through variable scanner displacement we provide geometries ranging from redundant projection data (i.e., standard fan beam geometry) to non-redundant single-sided projection data.

One of the most recent applications of computerized tomography is the non-invasive investigation of the internal micro-structure of objects with microtomography [B. P. Flannery, H. W. Deckman, W. G. Roberge, and K. L. D'Amico; "Three-Dimensional X-Ray Microtomography" *Science - American Association for the Advancement of Science*, Vol. 237, 1987, pp. 1439–1444., J. H. Kinney, Q. C. Johnson, R. A. Saroyan, M. C. Nichols, U. Bonse, R. Nusshardt, and R. Pahl; "Energy-modulated x-ray microtomography" *Review of Scientific Instruments*, Vol. 59, 1988, pp. 196–197.]. This technique is used to gain a better understanding of fabrication parameters of state-of-the-art ceramic composites and for investigation of geological samples, for instance, and in general provides a method of internal microscopy extending the range of applications of CT. The primary goal of microtomography is to obtain the projection data with a high inherent resolution, typically within the lower micrometer range. Various algorithms have been developed for software-based enhancement of the resolution in tomographic reconstructions [R. W. Gerchberg; "Super-resolution through error energy reduction" *Optica Acta*, Vol 21, 1974, pp. 709–720., R. A. Brooks and G. Di Chiro; "Statistical limitations in x-ray reconstructive tomography", *Medical Physics*, Vol. 3, 1976, pp. 237–240., P. M. Joseph and R. A. Schulz; "View sampling requirements in fan beam computed tomography" *Medical Physics*, Vol 7, 1980, pp 692–702., E. M. Haacke, Z. P. Liang, and S. H. Izen; "Superresolution Reconstruction Through Object Modeling and Parameter Estimation", *IEEE Transactions on Acoustics, Speech, and Signal Processing*, Vol. 37, 1989, pp, 592–595., S. Kuo and R. J. Mammone; "Resolution Enhancement of Tomographic Images Using the Row Action Projection Method" *IEEE Transactions on Medical Imaging*, Vol. 10, 1991, pp. 593–601.]. However, to achieve a substantial improvement in resolution, a number of modifications to the tomographic scanner hardware are necessary. While synchrotron sources provide X-ray beams of excellent collimation and monochromaticity, many small scale applications employ more practical laboratory fan or cone beam sources, which often result in blurred projection data due to penumbral broadening (i.e., finite size point sources) [J. H. Dunsmuir, S. R. Ferguson, K. L. D'Amico, and J. P. Stokes; "X-Ray Microtomography: A New Tool for the Characterization of Porous Media" (SPE 22860), *Proceedings of the Annual Technical Conference of the Society of Petroleum Engineers* - Part 2, Dallas, 1991, pp. 423–430.]. The quantum converter, or intensifying screen, transforming the attenuated X-rays into visible light is one of the "bottlenecks" in terms of resolution. Although phosphor layer based intensifying screens have been much improved [M. Ito, M. Yamaguchi, and K. Oba; "CsI(Na) Scintillation Plate with high spatial resolution", *IEEE Transactions on Nuclear Science*, Vol. 34, 1987, pp. 401–405., C. Carrier, C. Martel, D. Schmitt, and R. Lecomte; "Design of a high resolution positron emission tomograph using solid state scintillation detectors", *IEEE Transactions on Nuclear Science*, Vol. 35, 1988, pp. 685–690., R. Ning and R. A. Kruger; "Computer simulation of image intensifier-based computed tomography detector: Vascular application", *Medical Physics*, Vol. 15, 1988, pp. 188–192.], quantum interactions between grain cells within the converting phosphor-layer of the intensifying screen result in a substantial loss of resolution. Depending on the thickness of the phosphor layer, the resolution can be limited to the upper micrometer or even the millimeter range [G. U. V. Rao and P. Fatouros; "The relationship between resolution and speed of x-ray intensifying screens", *Medical Physics*, Vol. 5, 1978, pp. 205–208.]. However, recent microtomography scanners use cellular phosphor arrays which consist of optically isolated phosphor microcells and thus avoid quantum interactions between neighboring cells [H. W. Deckman, K. L. D'Amico, J. H. Dunsmuir, B. P. Flannery, and S. M. Gruner; "Microtomography detector design: it's not just resolution", *Advanced in X-Ray Analysis*, Vol. 32, 1989, pp, 641–650., H. W. Deckman, J. H. Dunsmuir, and S. M. Gruner; "Microfabrication of cellular phosphors", *Journal of Vacuum Science & Technology*, Vol. 7, 1989, pp. 1832–1835.]. This new technique has led to a substantial increase in the effective image resolution. In addition, the replacement of vidicon tubes by cooled CCD cameras for recording the projection image on the intensifying screen has further improved the noise statistics, linearity, and dynamic range of the scanners by more than an order of magnitude [K. N. Prettyjohns (Editor); State-of-the-Art Imaging Arrays and Their Applications, *Proceedings of SPIE - The International Society for Optical Engineering*, San Diego, Vol. 501, 1984., J. H. Kinney, Q. C. Johnson, U. Bonse, R. Nusshardt, and M. C. Nichols; "The performance of CCD array detectors for application in high-resolution tomography", *Proceedings of SPIE - the International Society for Optical Engineers*, Vol. 691, 1986, pp. 43–50.]. For modern systems combining the recent developments, effective resolutions of 10 μm and less are easily achieved.

None of the available methods, however, attempts to combine adjustments in the scanner hardware with modified preprocessing or reconstruction algorithms. The present invention provides a novel method of resolution enhancement, where we tilt the detector so as to spread the projection of a small object over a large portion of the detector. As will be shown, the detector is optimally utilized if we combine the detector tilt with a horizontal object shift so as to compensate for asymmetries in the projection magnification due to the fan beam geometry. Tilted Detector Microtomography (TDM) also efficiently reduces counter-effective blurring in resolution enhanced images due to penumbral broadening. Fan beam projection magnification by moving the investigated object closer to the source results in a substantial increase in penumbral blurring. With TDM, however, the object can in fact be moved closer to the detector to minimize penumbral blurring, while tilting the detector provides the necessary resolution enhancement.

Section 2 - Derivation of the Universal Fan Beam Algorithm

Before we develop the universal fan beam algorithm, let us briefly revisit the derivation of the standard fan beam convolution backprojection algorithm. From the Fourier Slice Theorem, we obtain through rearrangement of the direct Fourier reconstruction algorithm the parallel convolution backprojection as $$f(x,y) = \frac{1}{2} \int_0^{2\pi} \int_{-\infty}^{+\infty} p(\phi,s) h_w(x'-s) ds\, d\phi \qquad (1)$$

with $x' = x\cos(\phi) + y\sin(\phi)$. Here, $p(\phi,s)$ denotes the set of parallel beam projections with $\phi$ and $s$ the projection angle and the coordinate on the collinear detector respectively. The filter function $h_w$ is in practice approximated by $h_{wo}(t) = w_0^2(\text{sinc}(2w_0 t) - \text{sinc}^2(w_0 t))$ through band-limited evaluation of the integral $h_w \int |w| \exp(j2\pi) wt\, dw$. The ideal or standard fan beam geometry as depicted in FIG. 6a assumes that the center ray of the fan beam intersects the axis of object rotation and is perpendicularly incident at the center of the collinear detector. From these assumptions we easily find the characteristic beam parameters $\zeta$ and $\tau$ denoting the absolute ray angle and the ray displacement (i.e., the distance of the ray from the axis of object rotation) as $\zeta = \phi - \arctan(s/D)$ and $\tau = sd/\sqrt{D^2 + s^2}$. An image is reconstructed from a set of fan beam projections either through rebinning the projection data into an equivalent set of parallel beam projections prior to reconstruction with a standard parallel beam reconstruction algorithm, or with a modified algorithm immediately operating on the fan beam data. Rebinning of projection data prior to reconstruction involves interpolation and sampling, which reduces the inherent resolution of the projection data by up to 50%, such that in most cases the immediate solution is preferred. The mathematical manipulations are straightforward, such that with the ray angle and ray displacement for fan beam geometry equation (1) becomes $$f(x,y) = \frac{dD^2}{2} \int_0^{2\pi} \frac{1}{(y'+d)^2} \int_{-\infty}^{+\infty} \frac{1}{\sqrt{D^2 + s^w}} (\phi s) h_w\left(\frac{Dx'}{y'+d}\right) ds\, d\phi \qquad (2)$$

where we set $x' = x\cos(\phi) + y\sin(\phi)$ and $y' = y\cos(\phi) - x\sin(\phi)$. Here, $p(\phi,s)$ denotes the set of fan beam projections. The above algorithm operates immediately on the fan beam data and thus avoids loss of resolution through rebinning prior to reconstruction. Equation (2) is efficiently implemented and the execution runtime is comparable with that of a parallel beam algorithm.

However, the fan beam algorithm revised above requires adherence to the ideal fan beam geometry, where displacements of the detector, source, or investigated object with respect to the center ray, or a detector tilt, result in blurred and distorted images. Preprocessing algorithms to combat the effects of non-ideal fan beam geometries can be devised, however, these methods again involve a loss of resolution due to the required interpolation and sampling operations. Thus, we relax the geometrical constraints imposed on the ideal fan beam geometry and arrive at the model depicted in FIG. 6b, with the object rotated in the global system. The scanner system with the source horizontally aligned at distance $d$, however, is arbitrarily displaced with respect to the global system by the scanner displacement vector $\underline{\Delta}_s$. Accordingly, the detector system is arbitrarily displaced with respect to the scanner system by the detector displacement vector $\underline{\Delta}_d$, and rotated by the detector rotation $\psi_d$. With parameters $\underline{\Delta}_s$, $\underline{\Delta}_d$, and $\psi_d$ almost any non-ideal fan beam geometry can be modeled. As will be shown later, by adding an arbitrary scanner rotation $\psi_s$ the model is easily extended to a completely arbitrary fan beam geometry. With $\Delta_x$ and $\Delta_y$ the x and y components of the displacement vector $\underline{\Delta}$, the ray depicted in FIG. 6b in vector notation is described as $$\underline{r} = \begin{pmatrix} \Delta_{s,x} \\ \Delta_{s,y} - d \end{pmatrix} + t \begin{pmatrix} \Delta_{d,x} + s\cos(\psi_d) \\ \Delta_{d,y} + d + s\sin(\psi_d) \end{pmatrix} \qquad (3)$$

with $t$ the advancement parameter of the ray from the source ($t=0$) towards the detector ($t=1$). Note that for the remainder of the derivations we substitute $d' = d - \Delta_{x,y}$ and $D' = d + \Delta_{d,y}$ as the equivalent source-to-object and source-to-detector distances respectively. With vector calculus the modified ray angle and ray displacement become $$\xi = \phi - \arctan\left(\frac{\Delta_{s,x} + s\cos(\psi_d)}{D' + s\sin(\psi_d)}\right) \qquad (4)$$

$$\tau = \frac{\Delta_{s,x} D' + \Delta_{d,x} d' + s(d'\cos(\psi_d) + \Delta_{s,x}\sin(\psi_d))}{\sqrt{(\Delta_{d,x} + s\cos(\psi_d))^2 + (D' + s\sin(\psi_d))^2}} \qquad (5)$$

The ray parameters in (4) and (5) define the mapping of a rebinning procedure $p_{f+}(\phi,s) \to p_p(\zeta,\tau)$ resorting the universal fan beam data in $p_{f+}$ into an equivalent set of parallel beam projections in $p_p$. However, as mentioned earlier we wish to avoid preprocessing of projection data since it reduces the inherent projection resolution, such that we aim at a modified fan beam reconstruction algorithm immediately operating on the new fan beam data. For the further derivation of the algorithm, let us return to the parallel beam equation in (1), where we now use the functions $\phi(\zeta,\tau)$ and $s(\zeta,\tau)$ as the inverse pair of equations (4) and (5), $$f(x,y) = \frac{1}{2} \int_0^{2\pi} \int_{-\infty}^{+\infty} p(\phi(\xi,\tau), s(\xi,\tau)) h_w(x'-\tau) d\tau\, d\xi \qquad (6)$$

defining $x'$ as before. Note that $p(\phi,s)$ is the new set of fan beam projections recorded in the non-ideal fan beam geometry with the scanner and detector displacements $\underline{\Delta}_s$, $\underline{\Delta}_d$, and the detector rotation $\psi_d$. To resolve the above equation we need to evaluate the Jacobian $J$ of the integral pair $$J = \begin{vmatrix} \frac{d\tau}{ds} & \frac{d\tau}{d\phi} \\ \frac{d\xi}{ds} & \frac{d\xi}{d\phi} \end{vmatrix} = \frac{d\tau}{ds} \qquad (7)$$

where we have used the fact that the ray angle $\zeta$ is linearly dependent on $\phi$, i.e., $d\zeta/d\phi = 1$, and the ray displacement $\tau$ is not a function of $\phi$, i.e., $d\tau/d\phi = 0$. Through a tedious mathematical derivation, the Jacobian is eventually resolved as $$J = \frac{(d'D' - \Delta_{s,x}\Delta_{d,x})(D'\cos(\psi_d) - \Delta_{d,x}\sin(\psi_d))}{\sqrt{(\Delta_{d,x} + s\cos(\psi_d))^2 + (D' + s\sin(\psi_d))^2}} +$$

$$s\frac{(d'\cos(\psi_d) + \Delta_{s,x}\sin(\psi_d))(\Delta_{d,x}\cos(\psi_d) + D'\sin(\psi_d)) - (\Delta_{s,x}D' + \Delta_{d,x}d')}{\sqrt{(\Delta_{d,x} + s\cos(\psi_d))^2 + (D' + s\sin(\psi_d))^2}} \qquad (8)$$

We substitute $d\tau d\phi = J ds\, d\phi$ and equations (4) and (5) in (6) and arrive after a number of tedious manipulations at the final modified fan beam reconstruction algorithm $$f(x,y) = \frac{1}{2} \int_0^{2\pi} \frac{1}{(y\cos(\phi+\psi_d) - x\sin(\phi+\psi_d) + d'\cos(\psi_d) + \Delta_{s,x}\sin(\psi_d))^2} \int_{-\infty}^{+\infty} J(s) p(\phi,s) \times \qquad (9)$$

$$h_w\left(\frac{x(D'\cos(\phi) + \Delta_{d,x}\sin(\phi)) + y(D'\sin(\phi) - \Delta_{d,x}\cos(\phi)) - (\Delta_{s,x}D' + \Delta_{d,x}d')}{y\cos(\phi+\psi_d) - x\sin(\phi+\psi_d) + d'\cos(\psi_d) + \Delta_{s,x}\sin(\psi_d)} - s\right) ds\, d\phi$$

where we use the Jacobian J as defined in equation (8). Note that J(s) is a simple function of s, where the terms independent of s can be evaluated prior to reconstruction. In fact, implementation of equation (9) has shown that the execution runtimes of the universal fan beam algorithm are comparable with those of a standard fan beam convolution backprojection. Many of the terms in (9) are either constants or semi-constants, and the complex backprojection term inside the filter function $h_w$ is particularly well suited for rapid implementation with a vectorized backprojection scheme.

Note that equations (8) and (9) collapse to the standard fan beam algorithm in (2), if we set $\Delta_s=0$, $\Delta_d=(D-d, 0)^T$ and $\psi_d=0$. Here the equivalent source-to-object and source-to-detector distances d' and D' are identical to the metric distances d and D. In sections 3.1 through 3.4 we will apply the new algorithm to various practical problems in computerized tomography, where through the study of isolated cases the structural differences between the modified and the standard fan beam reconstruction algorithm will be emphasized.

Section 2.1 - - - Extension to Arbitrary Geometries

We have derived a fan beam algorithm for reconstruction from projections recorded in a geometry with arbitrary scanner displacement $\underline{\Delta}_s$, detector displacement $\underline{\Delta}_d$, and detector tilt $\psi_d$. By adding an arbitrary scanner tilt, we extend the algorithm to a universal fan beam algorithm capable of reconstructing from arbitrary geometries defined now by the scanner and detector systems $S_s$ and $S_d$. We define a system as the set of translation and rotation parameters $S=\{t_x, t_y, \alpha\}$, and we obtain the displacement and rotation parameters for equations (8) and (9) as $$d' = (d - t_{s,y}) \cos(\alpha_s) - t_{s,x} \sin(\alpha_s) \qquad (10)$$

$$D' = (d + t_{d,y}) \cos(\alpha_s) + t_{d,x} \sin(\alpha_s) \qquad (11)$$

$$\Delta_{s,x} = t_{s,x} + d \sin(\alpha_s) \qquad (12)$$

$$\Delta_{d,x} = t_{d,x} \cos(\alpha_s) - t_{d,y} \sin(\alpha_s) \qquad (13)$$

$$\psi_d = \alpha_s + \alpha_d \qquad (14)$$

In operator notation an image is now recovered as $f(x,y) = \text{REC}[S_s, S_d]\{p(\phi,s)\}$, where REC is the reconstruction operator for equations (9) and (8), while $p(\phi,s)$ denotes the set of projections recorded in the fan beam geometry described by the scanner and detector systems $S_s$ and $S_d$ respectively. With the universal fan beam algorithm, we do no longer have to concentrate on adhering to the ideal standard fan beam geometry as depicted in FIG. 6a. Instead, we are able to modify the scanner geometry arbitrarily to our advantage, and choose displacements and tilt angles so as to achieve a desired effect on the projections.

Section 3 - - - Applications of the Universal Fan Beam Algorithm

Figure 7A:
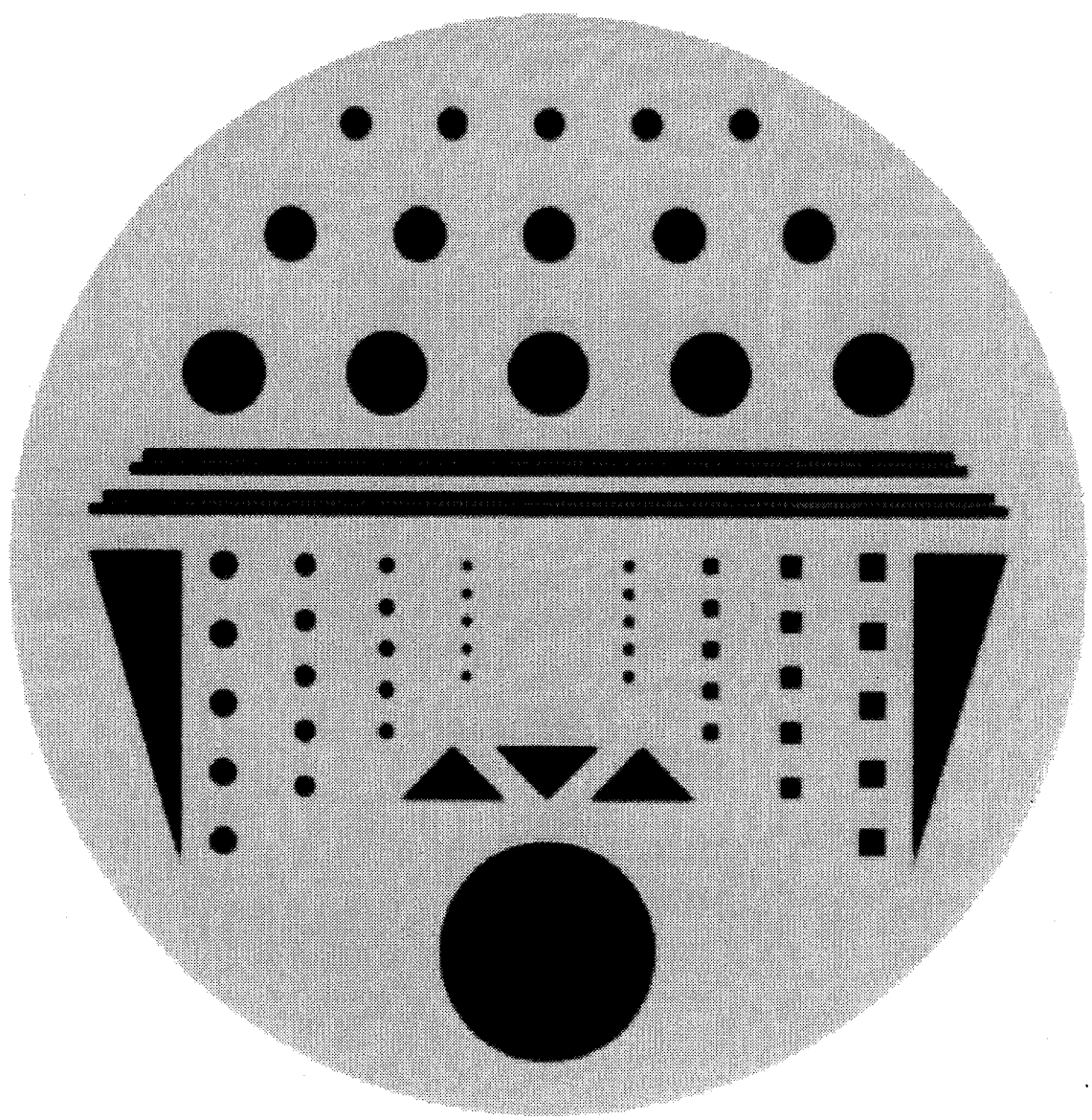
FIG. 7 shows the simulated object. In (a), the image of the object is shown. The white, grey, and black portions of the image correspond to densities of 0.0, 0.3, and 1.0 respectively. In (b), the standard convolution backprojection reconstruction from ideal fan beam projection data is shown.
Figure 7B:
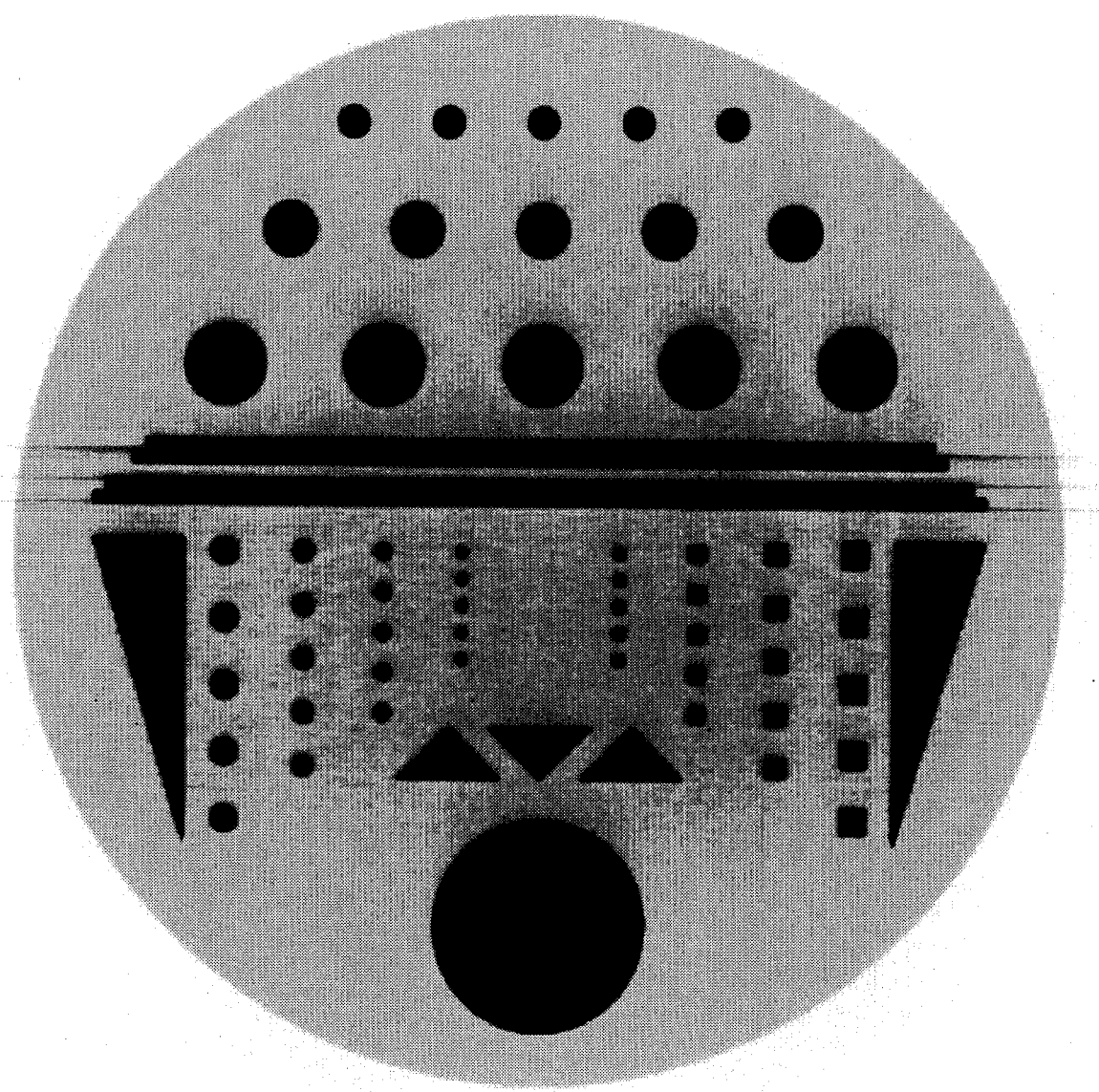

In this section, we apply the universal fan beam algorithm to various non-ideal geometries. We evaluate the performance of the algorithm and its advantages over the standard fan beam convolution backprojection by reconstructing the object shown in FIG. 7a from its simulated projections. A standard reconstruction from ideal fan beam projection data is shown in FIG. 7b.

Note that all reconstructions are computed without smoothing to emphasize the raw image performance of the studied algorithms. Smoothing (e.g., application of a raised-cosine filter or Hamming/Hanning window in the frequency domain) substantially reduces the presence of aliasing artifacts and thus improves the image quality.

Unless otherwise noted, the projections are of resolution $N_\phi \times N_s = 601 \times 601$. As a quantitative measure of the distance between a reconstructed image and the ideal reconstruction in FIG. 7b, we provide rms-error values. In addition, we provide correlation coefficients as a qualitative measure of the visual similarity between a reconstructed image and the ideal reconstruction Note that the rms-error is computed as $e = (N^{-1}\Sigma_N(x_i - y_i)^2)^{1/2}$, while the correlation coefficient is defined as $r = \text{cov}(X,Y)/(\text{var}(X)\text{var}(Y))^{1/2}$ with $\text{cov}(X,Y) = N^{-1}\Sigma_N(x_i - \mu_x)(y_i - \mu_y)$ and $\text{var}(X) = N^{-1}\Sigma_N(x_i - \mu_x)^2$ where $\mu_x = N^{-1}\Sigma_N x_i$.

Section 3.1 - - - Center-Displaced Reconstruction

Since the projection geometry leading to the new reconstruction algorithm in equations (8) and (9) accounts for arbitrary scanner and detector displacements, we apply the solution found in the previous chapter to the displacement problem commonly encountered in tomography. Due to mechanical misalignment and inaccuracies in the scanner setup, we are almost always dealing with a non-ideal scanner geometry with either a detector, source, or scanner displacement, or a combination of these. FIG. 8 illustrates the three types of misalignment in tomographic fan beam scanners.

Figure 8C:
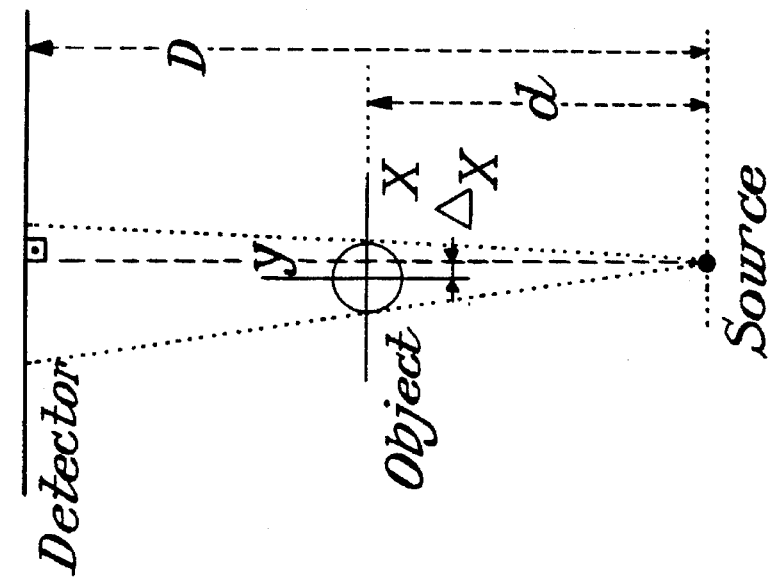
FIG. 8 shows three diagrams (view from above) which illustrate the geometry of center-displaced projections. Parameter $\Delta_x$ denotes the horizontal displacement. In (a), detector displacement is shown. In (b), source displacement is shown. In (c), scanner displacement is shown.
Figure 8B:
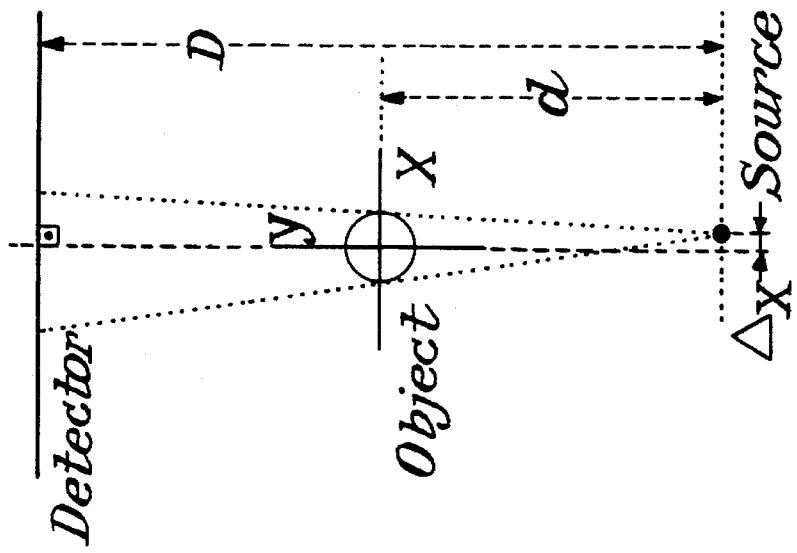
Figure 8A:
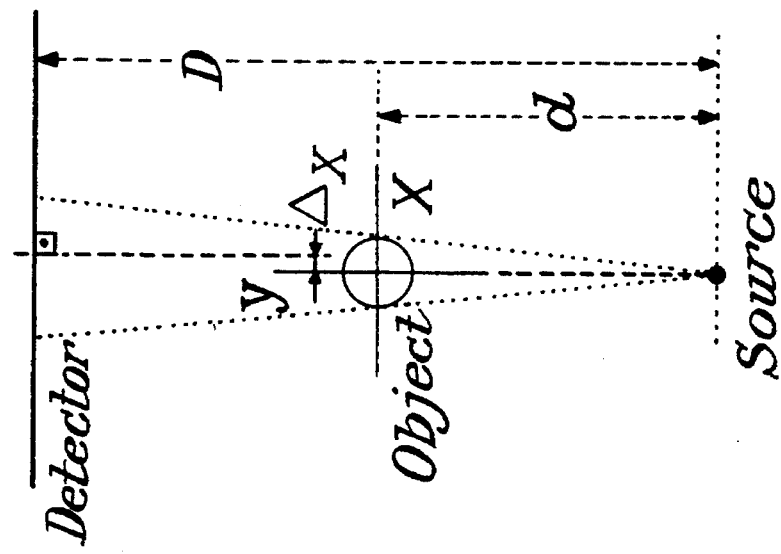

Note that a scanner displacement, as illustrated in FIG. 8c, is equivalent to an identical object shift in the opposite direction. Treating the misalignment cases isolatedly will emphasize the adjustments necessary to the standard fan beam algorithm. Thus, considering only the displacement components $\Delta_{d,x} \neq 0$, $\Delta_{s,x} = -\Delta_{d,x} \neq 0$, and $\Delta_{s,x} \neq 0$ according to the three cases depicted in FIG. 8a, 8b, and 8c respectively, we obtain $$f(x,y) = \frac{dD^2}{2} \int_0^{2\pi} \frac{1}{(y'+d)^2} \int_{-\infty}^{+\infty} \frac{1}{\sqrt{D^2 + (s+\Delta_x)^2}} p(\phi,s) h_w\left(\frac{Dx' - \Delta_x(y'+d)}{y'+d} - s\right) ds\, d\phi \qquad (15)$$

$$f(x,y) = \frac{D}{2} \int_0^{2\pi} \frac{1}{(y'+d)^2} \int_{-\infty}^{+\infty} \frac{dD + \Delta_x^2 - s\Delta_x}{\sqrt{D^2 + (s-\Delta_x)^2}} p(\phi,s) h_w\left(\frac{D(x' - \Delta_x) + \Delta_x(y'+d)}{y'+d} - s\right) ds\, d\phi \qquad (16)$$

$$f(x,y) = \frac{D}{2} \int_0^{2\pi} \frac{1}{(y'+d)^2} \int_{-\infty}^{+\infty} \frac{dD - s\Delta_x}{\sqrt{D^2 + s^2}} p(\phi,s) h_w \left( \frac{D(x' - \Delta_x)}{y' + d} - s \right) ds\, d\phi \quad (17)$$

where we set x'=xcos (φ)+ysin (φ) and y'=ycos (φ)−xsin (φ). Note that equation (16) is obtained from (9) by setting the scanner and detector displacements $\Delta_{s,x} = -\Delta_{d,x} = \Delta_x$ to model the source displacement depicted in FIG. 8b. Equations (15), (16), and (17), reconstruct artifact-free from sets of fan beam projections subjected to detector, source, and scanner displacements respectively. Table 1 lists the rms-error and correlation in reconstructions from displaced projections, with and without displacement compensation, compared with a standard reconstruction from ideal fan beam projection data.

TABLE 1

Rms-error and correlation in reconstructions from different types of center-displaced projections.

| Displacement | Detector (FIG. 3a) | | Source (FIG. 3b) | | Scanner (FIG. 3c) | |
| --- | --- | --- | --- | --- | --- | --- |
| Reconstruction | Standard | Universal | Standard | Universal | Standard | Universal |
| RMS-Error | 0.14995 | 0.00098 | 0.15093 | 0.01484 | 0.20772 | 0.01500 |
| Correlation | 0.85185 | 0.99999 | 0.84979 | 0.99865 | 0.70550 | 0.99862 |

Figure 9A:
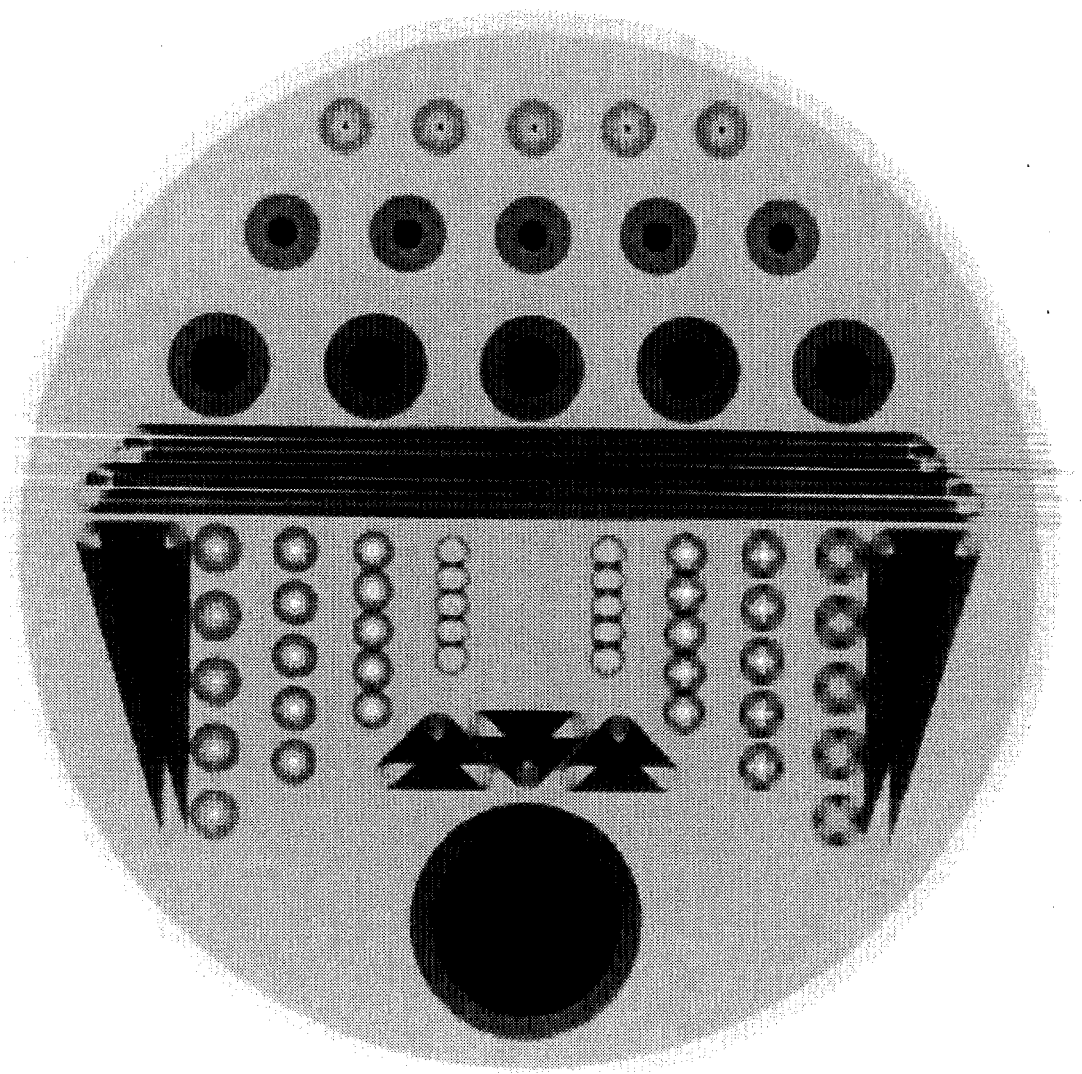
FIG. 9 shows reconstruction from detector center-displaced projection data. In (a), reconstruction with standard fan beam algorithm is shown. In (b), reconstruction with universal fan beam algorithm accounting for arbitrary detector displacement is shown.
Figure 9B:
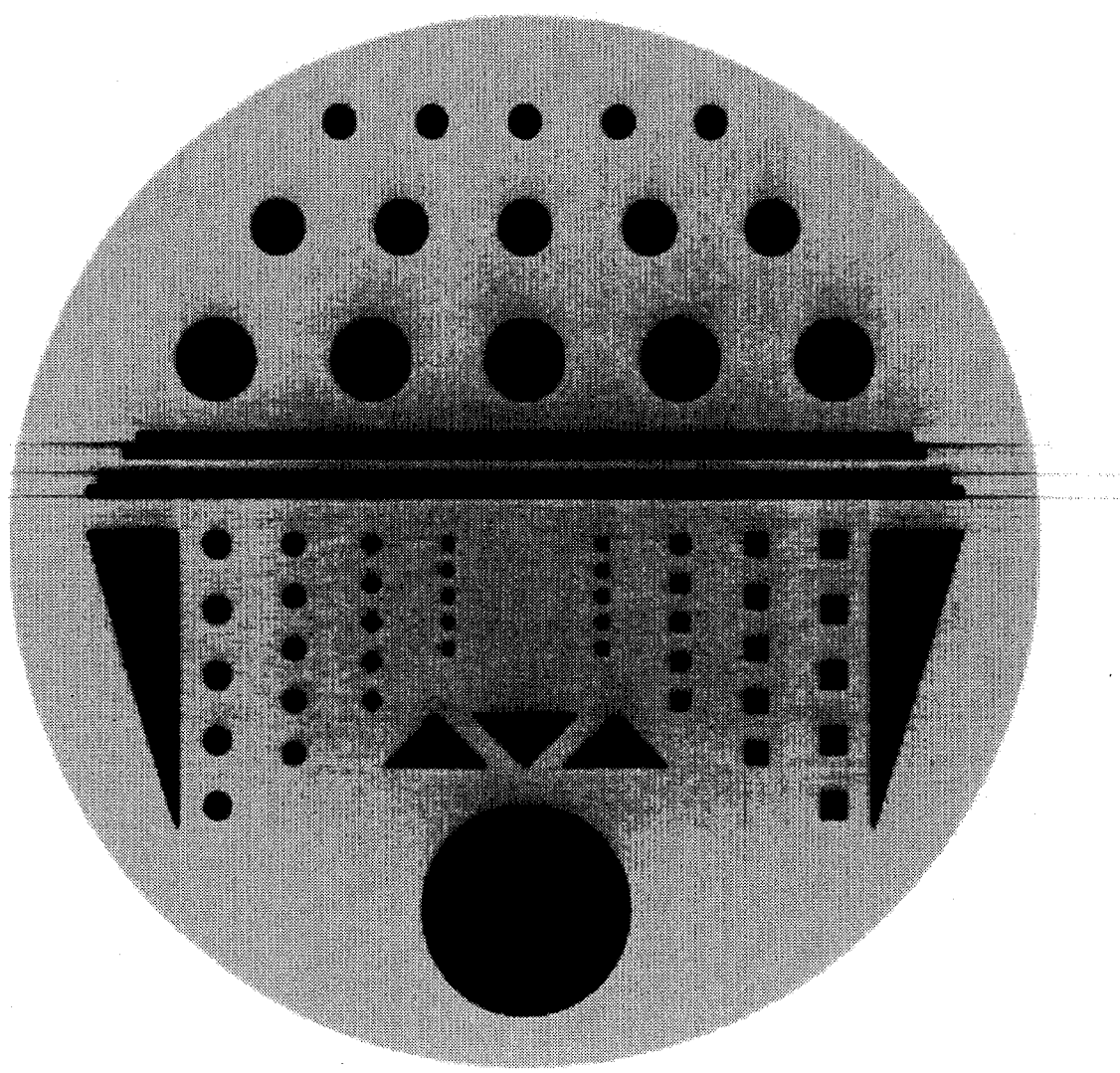

Reconstruction from center-displaced projection data of any of the above displacement types results in image blurring, with little difference between images recovered from projections subjected to detector, source, or scanner displacement. The blurred image obtained with a standard fan beam convolution backprojection without shift compensation from detector center-displaced projection data is shown in FIG. 9a, while the blur-free reconstruction with the applied universal fan beam algorithm in equation (15) is illustrated in FIG. 9b.

Section 3.2 - - - Non-Redundant Single-Sided Reconstruction

Figure 10C:
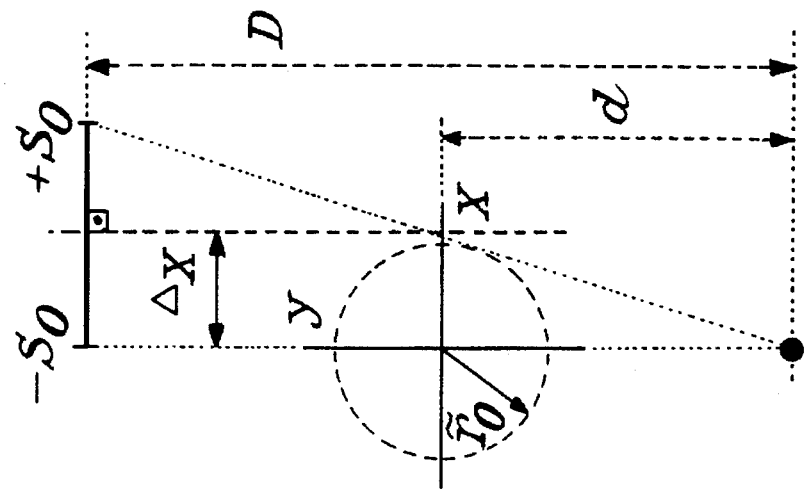
FIG. 10 shows three diagrams (view from above) which illustrate the geometry of standard and non-redundant single-sided fan beam projections. Parameter $\Delta_x$ denotes the horizontal displacement. The dashed circles of radii $r_o$ and $\tilde{r}_o$ delimit the individual artifact-free zones of the standard and single-sided scanner respectively. In (a), a standard projection is shown. In (b), type-I single-sided projection is shown, equivalent to a scanner displacement. In (c), type-II single-sided projection is shown, equivalent to a detector displacement.
Figure 10B:
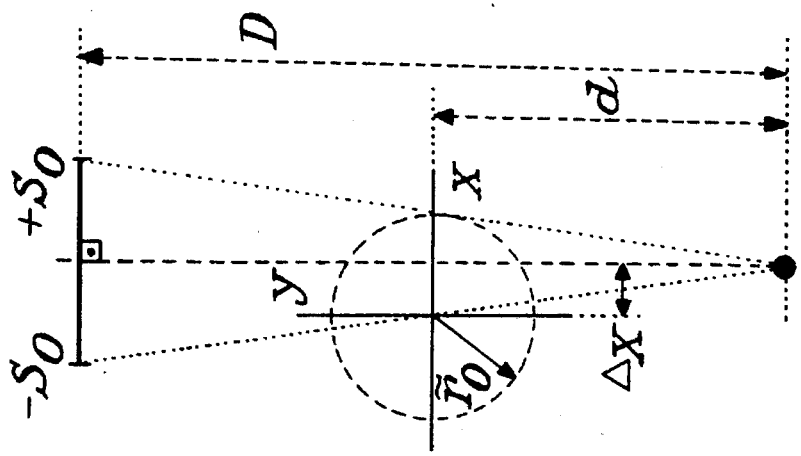
Figure 10A:
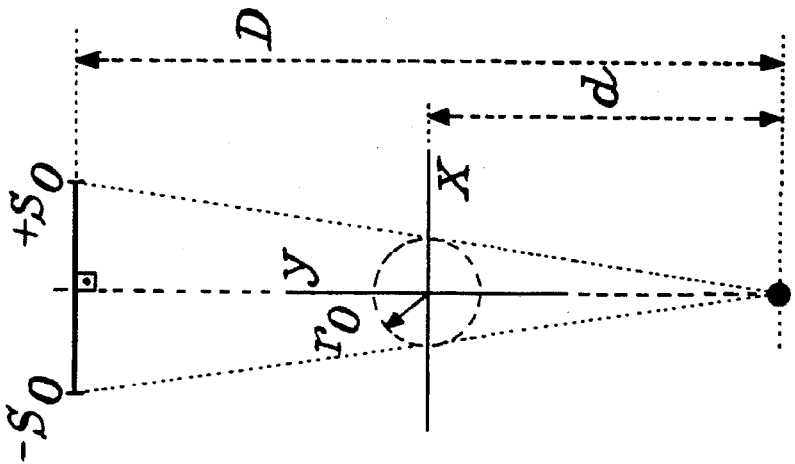

Another application of reconstruction from center-displaced projections is single-sided tomography. In fan beam tomography, the projections are usually recorded over a full circle. With equivalence of parallel and fan beam projections, this procedure results in redundant data, i.e. every ray will be contained twice in the set of fan beam projections, travelling through the projected object in opposite directions. While in the simpler parallel beam geometry this fact allows avoiding redundancy by limiting the data acquisition to a semi-circle as suggested by rewriting equation (1) to $$f(x,y) = \int_0^\pi \int_{-\infty}^{+\infty} p(\phi,s) h_w(x' - s)\, ds\, d\phi,$$

we cannot equally easily apply this method to fan beam geometry. Here, integration over the full circle is an inherent necessity in the derivation of the standard fan beam algorithm, where the excellent image quality of fan beam reconstructions can be attributed to desirable symmetry properties in the fan beam data due to redundancy. However, reconstruction from non-redundant single-sided fan beam projections, as depicted in FIG. 10, fully utilizes the available detector and thus extends the radius of the artifact-free zone for investigation of larger objects. We therefore follow this concept and apply the universal fan beam algorithm to the new geometry. We distinguish between single-sided tomography with a detector-centered source (Type-I, see FIG. 10b) and an object-centered source (Type-II, see FIG. 10c).

By precisely choosing horizontal scanner and detector displacements, we achieve zero redundancy without loss of completeness in the projection data. Also, we extend the radius of the artifact-free zone, which for the standard fan beam scanner amounts to $r_o = s_0 d / \sqrt{D^2 + s_0^2}$. Table 2 gives the necessary displacements $\Delta_x$ and the radii $\tilde{r}_0$ of the resulting artifact-free zones,

TABLE 2

Displacements $\Delta_x$ and radii $\tilde{r}_0$ of the artifact-free zones for Type-I and Type-II single-sided scanners.

Figure 5A:
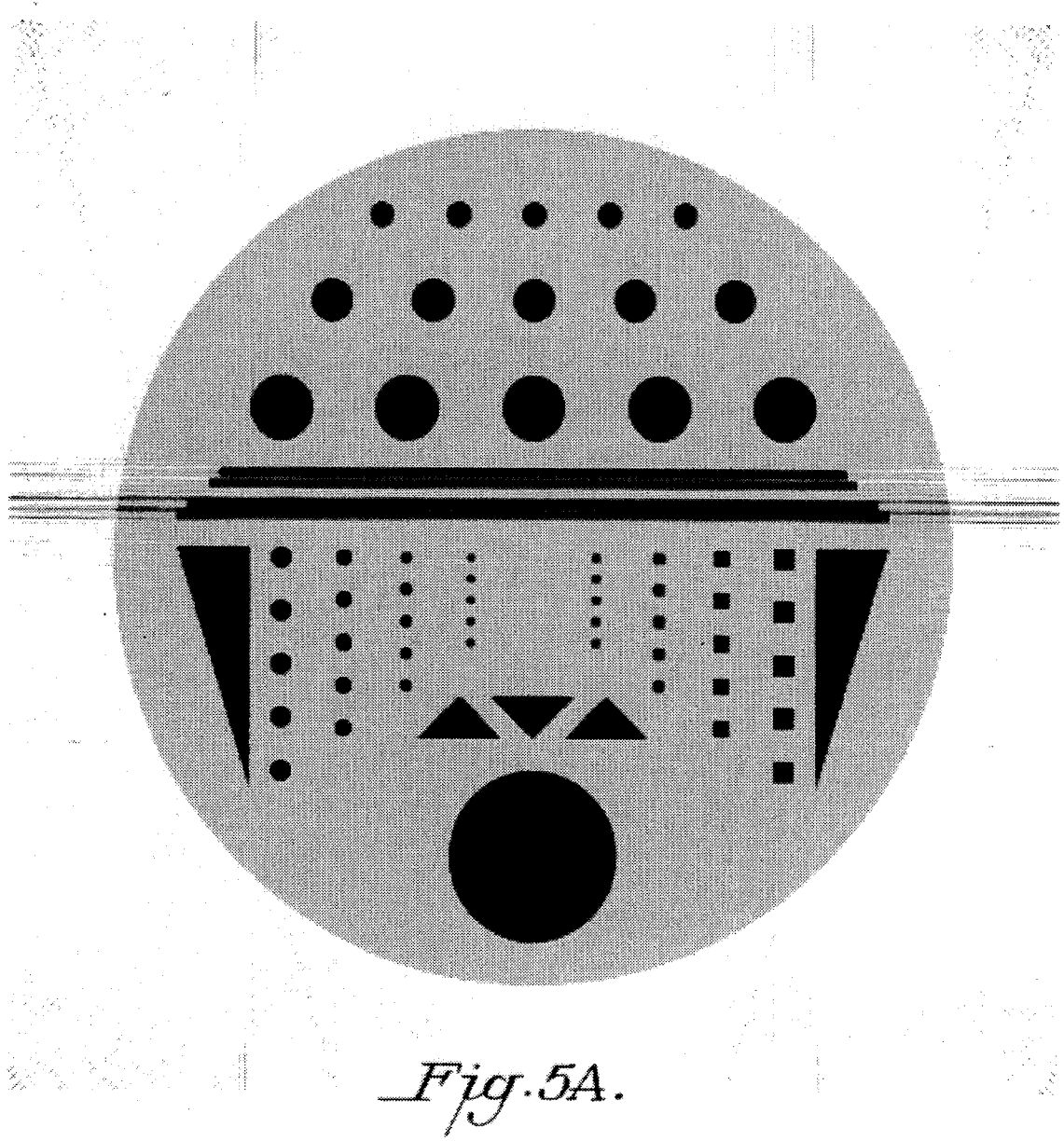
FIG. 5 shows a comparison of reconstructions from resolution enhanced sets of projections. Both images were subjected to the same degree of resolution enhancement. The images in the second row are the residual artifacts after subtraction of an ideal reconstruction. In (a), the resolution enhancement is obtained by moving the object close to the point-source. In (b), the resolution enhancement is obtained by detector tilting. In (c), residual artifacts in the reconstruction in (a) are shown. In (d), residual artifacts in the reconstruction in (b) are shown.
Figure 5B:
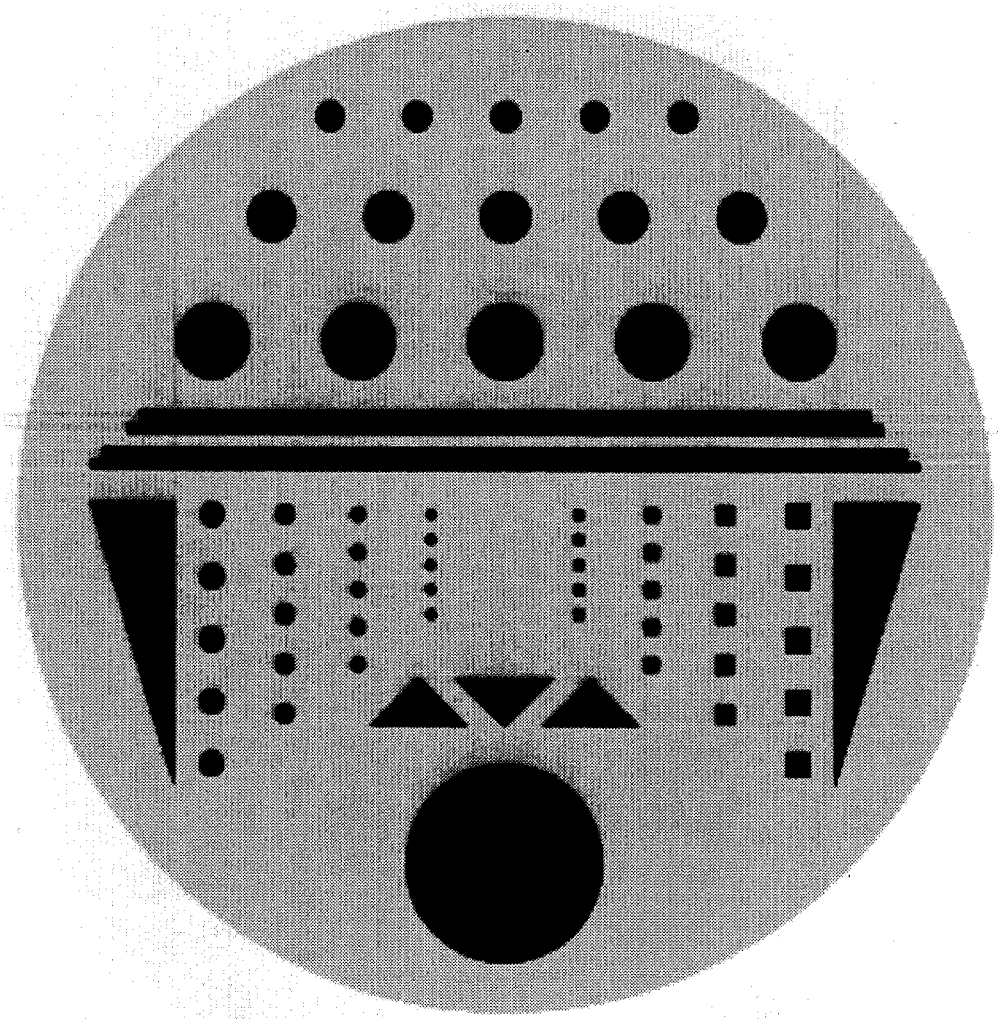
Figure 5C:
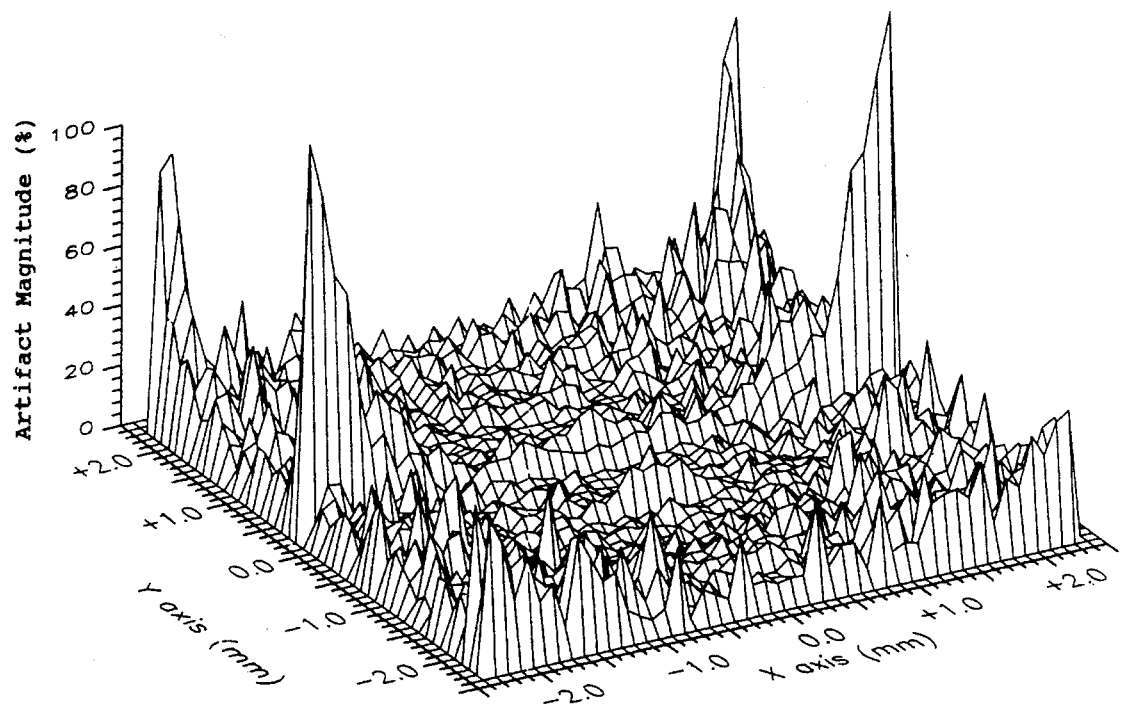
Figure 5D:
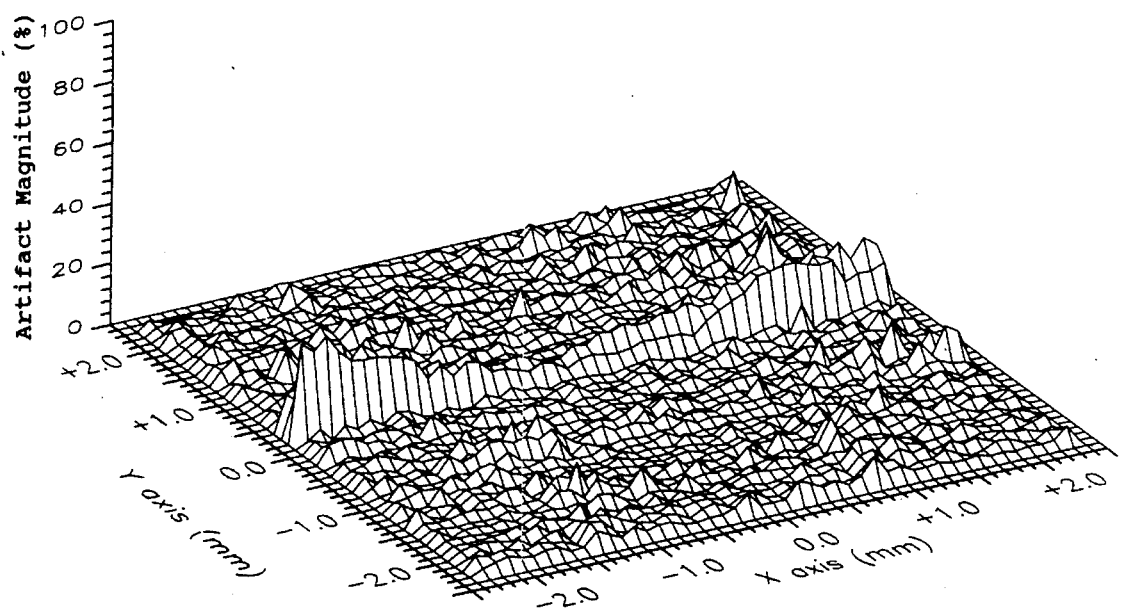

| Scanner Type | Type-I (FIG. 5b) | Type-II (FIG. 5c) |
| --- | --- | --- |
| $\Delta_x$ | $s_0 \dfrac{d}{D}$ | $2 s_0 \dfrac{d}{D}$ |
| $\tilde{r}_0$ | $\dfrac{2 s_0 d}{\sqrt{D^2 + s_0^2}}$ | $\dfrac{2 s_0 d}{\sqrt{D^2 + s_0^2}}$ | which are easily obtained from the geometry in FIG. 10. Note that for a Type-I scanner the displacement $\Delta_x$ is applied as a scanner displacement $\Delta_{s,x}$, while for the Type-II scanner the displacement is a detector shift $\Delta_{d,x}$. As shown in Table 2, a type-I single-sided scanner achieves a slightly larger extension of the artifact-free zone than a type-II scanner, while requiring only half the displacement of a type-II single-sided scanner. Both types approximately double the radius of the artifact-free zone. The universal fan beam algorithm in equations (8) and (9) reduces thus to special cases of the displacement reconstruction algorithms presented in (15) and (17), such that $$f(x,y) = \frac{D}{2} \int_0^{2\pi} \frac{1}{(y'+d)^2} \int_{-\infty}^{+\infty} \frac{dD - s s_0 \frac{d}{D}}{\sqrt{D^2 + s^2}} p(\phi,s) h_w \left( \frac{D\left(x' - s_0 \frac{d}{D}\right)}{y' + d} - s \right) ds\, d\phi \quad (18)$$

$$f(x,y) = \frac{dD^2}{2} \int_0^{2\pi} \frac{1}{(y'+d)^2} \int_{-\infty}^{+\infty} \frac{1}{\sqrt{D^2 + \left(s + 2s_0\frac{d}{D}\right)^2}} \, p(\phi,s) h_w\left(\frac{D_x' - 2s_0\frac{d}{D}(y'+d)}{y'+d} - s\right) ds \, d\phi \quad (19)$$

where the algorithm in equation (18) reconstructs from single-sided projection data with a detector-centered source, while (19) reconstructs from single-sided projection data with an object-centered source. Note that if we do not change the global scaling of the algorithms in (18) and (19) (i.e., cancel the ½ terms in front of the first integral in each equation) we have to scale the projection data x2 in order to account for the reduced number of measurements.

Table 3 lists the rms-error and correlation in reconstructions from non-redundant single-sided projections of type-I and type-II, compared with a reconstruction from ideal fan beam projection data.

TABLE 3

Rms error and correlation in reconstructions from single-sided projections for low and high projection resolution.

| Scanner Type | Type-I (FIG. 5b) | | Type-II (FIG. 5c) | |
|---|---|---|---|---|
| Resolution $N_\phi \times N_3$ | $301^2$ | $601^2$ | $301^2$ | $601^2$ |
| RMS-Error | 0.16364 | 0.15929 | 0.15926 | 0.15123 |
| Correlation | 0.86269 | 0.87006 | 0.86814 | 0.88282 |

Figure 11A:
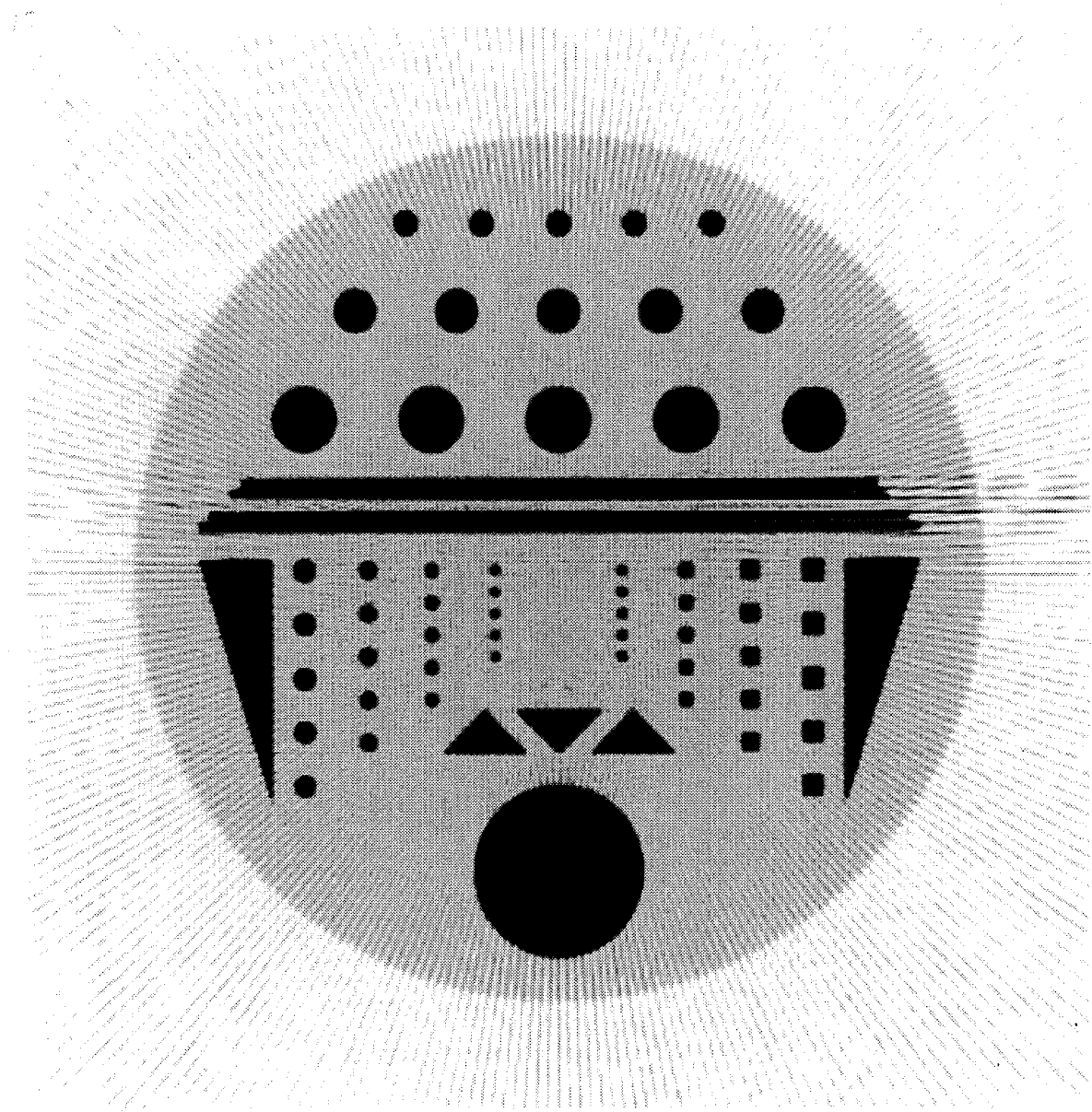
FIG. 11 shows reconstruction from non-redundant single-sided projection data. In (a), the reconstruction is from type-I projection data with $N_\phi \times N_x = 301^2$. In (b), the reconstruction is from type-I projection data with $N_\phi \times N_x = 601^2$.
Figure 11B:
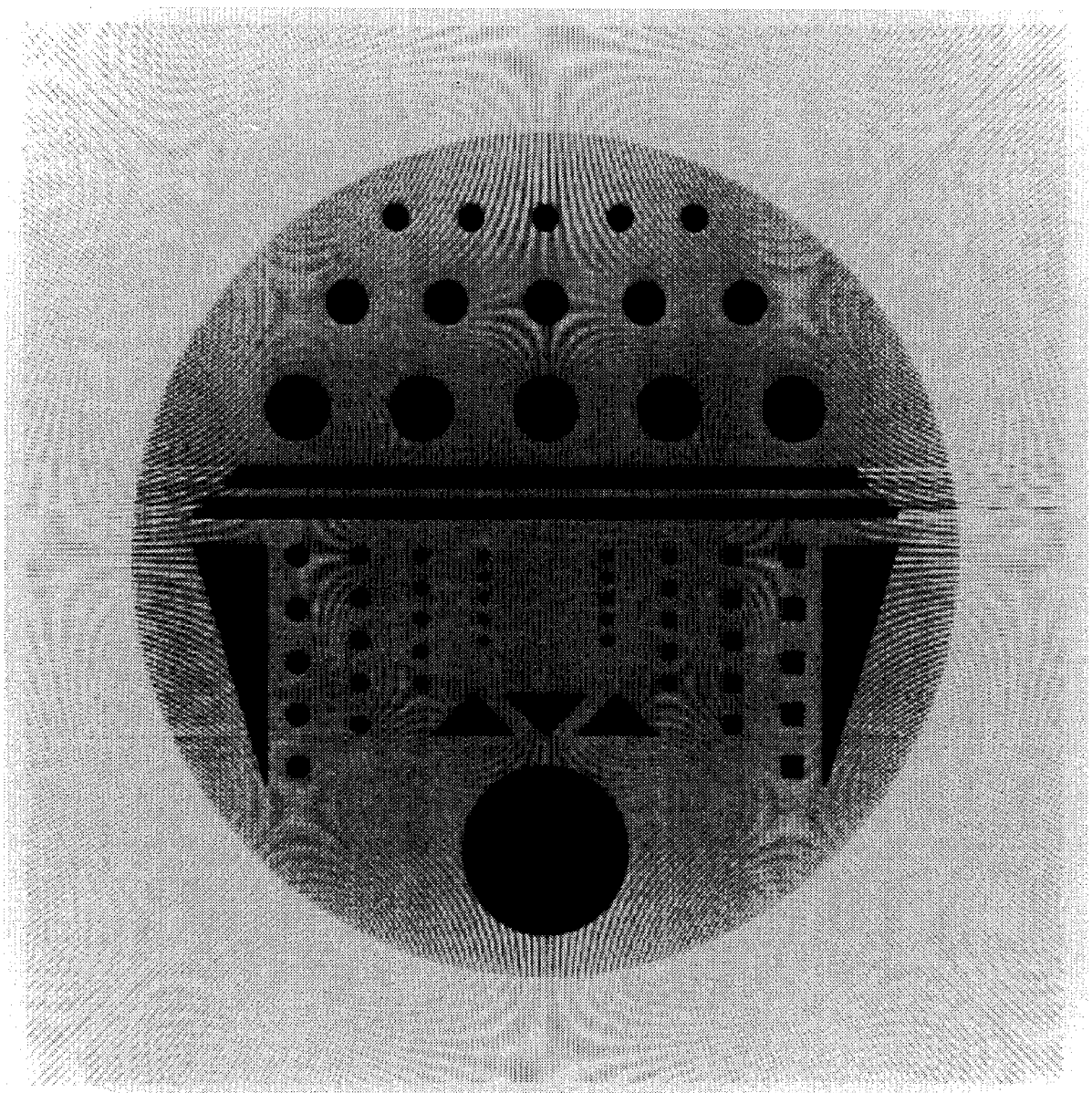

Reconstructed images obtained with the algorithm in equation (18) are illustrated in FIG. 11. The poor quality of the images results from the lack of symmetry in non-redundant fan beam projections. This deficiency, however, can be lessened by increasing the spatial resolution of the detector, as shown in FIG. 11b, or through application of smoothing during the reconstruction, as suggested by Table 11 in the Appendix.

Section 3.3 - - - Partially Redundant Reconstruction

Let us now consider a mixed case, where we reconstruct the center portion of the investigated object from redundant projections for high image quality, while the outer portion of the object may be reconstructed with lesser quality and contrast using non-redundant projections. We therefore aim at combining the geometry of single-sided reconstruction discussed in Section 3.2 extending the radius of the artifact-free zone with the excellent image quality of reconstruction from redundant standard fan beam projection data. Here, we concentrate on applying the type-I scanner principle to partially redundant reconstructions, due to its more symmetric setup. However, partially redundant reconstruction can also be applied using the type-II scanner principle. FIG. 12 illustrates the geometry of partially redundant projections.

With the scanner displacement now ranging in $0<\Delta_x<s_0d/D$, we evaluate the radius $\tilde{r}_0$ of the artifact-free zone and the radius $\tilde{r}_0'$ of the zone of redundant reconstruction. Introducing the redundancy coefficient $0 \leq \eta \leq 1$ where $\eta=0$ denotes a fully redundant (i.e. standard) projection while $\eta=1$ indicates a non-redundant (i.e. single-sided) projection, we write $$\tilde{r}_0 = (1+\eta) \frac{s_0 d}{\sqrt{D^2 + s_0^2}} \quad (20)$$

$$\tilde{r}_0' = (1-\eta) \frac{s_0 d}{\sqrt{D^2 + s_0^2}} \quad (21)$$

where $\tilde{r}_0 > \tilde{r}_0'$ for $0 < \eta < 1$ and thus the associated scanner displacement $\Delta_x = \eta s_0 d/D$. From equations (20) and (21) we also obtain $\eta = (\tilde{r}_0 - \tilde{r}_0')/(\tilde{r}_0 + \tilde{r}_0')$. Note that for $\eta=0$ we have zero scanner displacement $\Delta_x=0$ and thus completely redundant standard fan beam projections, while for $\eta=1$ we have the non-redundant single-sided case discussed in the previous section. Note that for energy balance, the non-redundant projections are scaled x2 before reconstruction, while the redundant portion of the scan data is left unchanged.

Figure 13A:
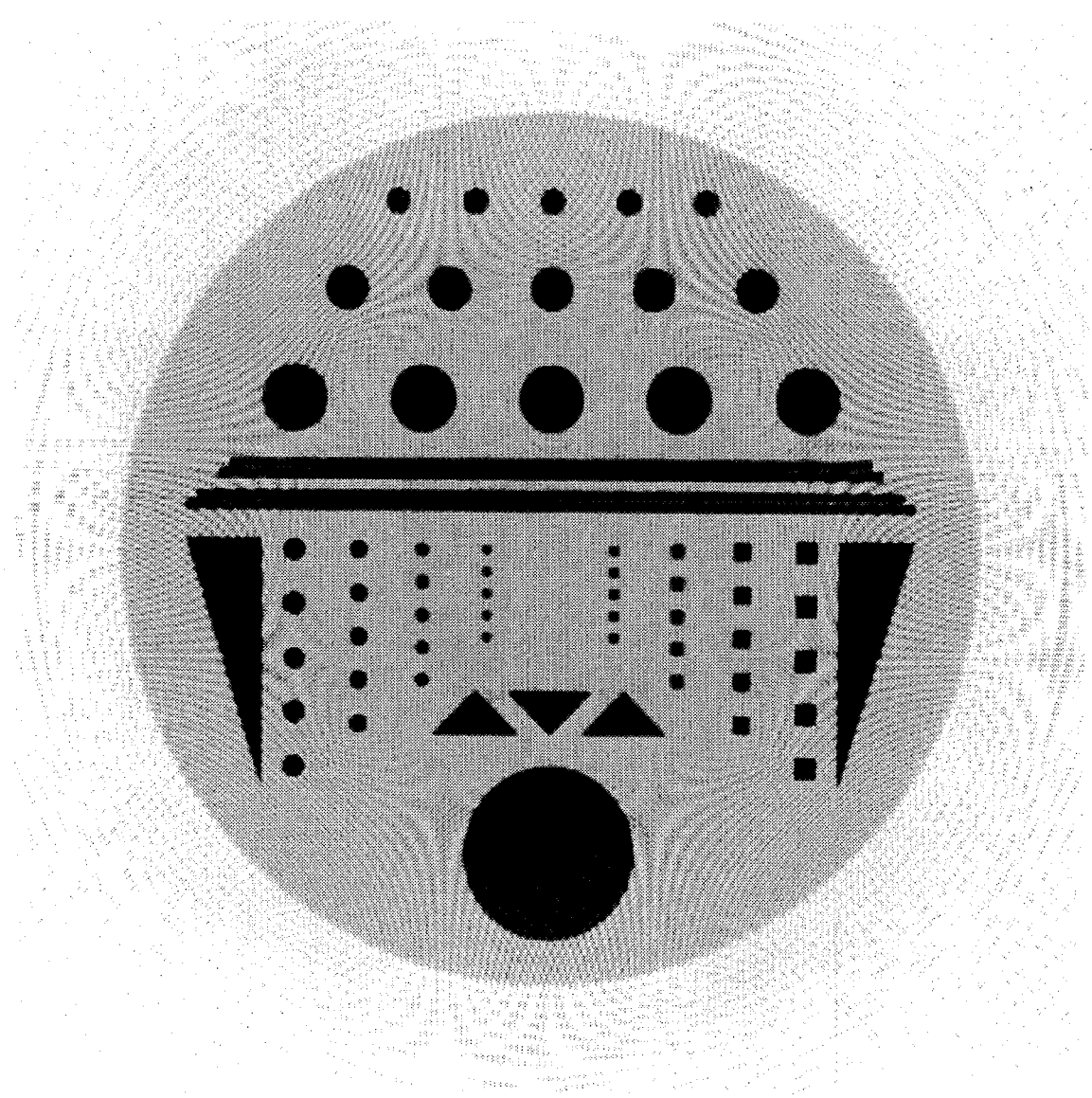
FIG. 13 shows reconstruction from partially redundant projection data for different redundancy coefficients $\eta$. In (a), $\eta$=0.8. In (b), $\eta$=0.6. In (c), $\eta$=0.4.
Figure 13B:
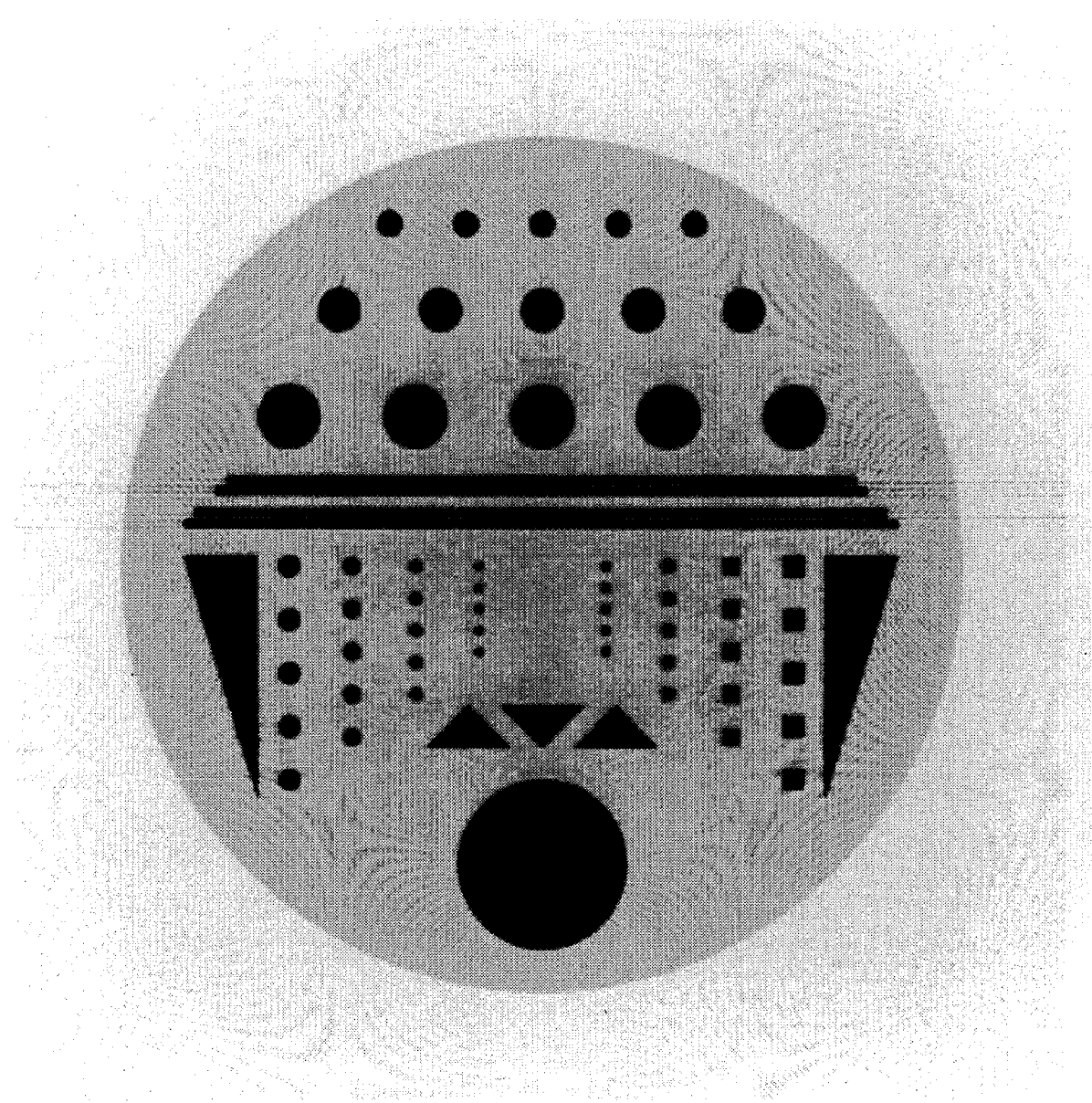
Figure 13C:
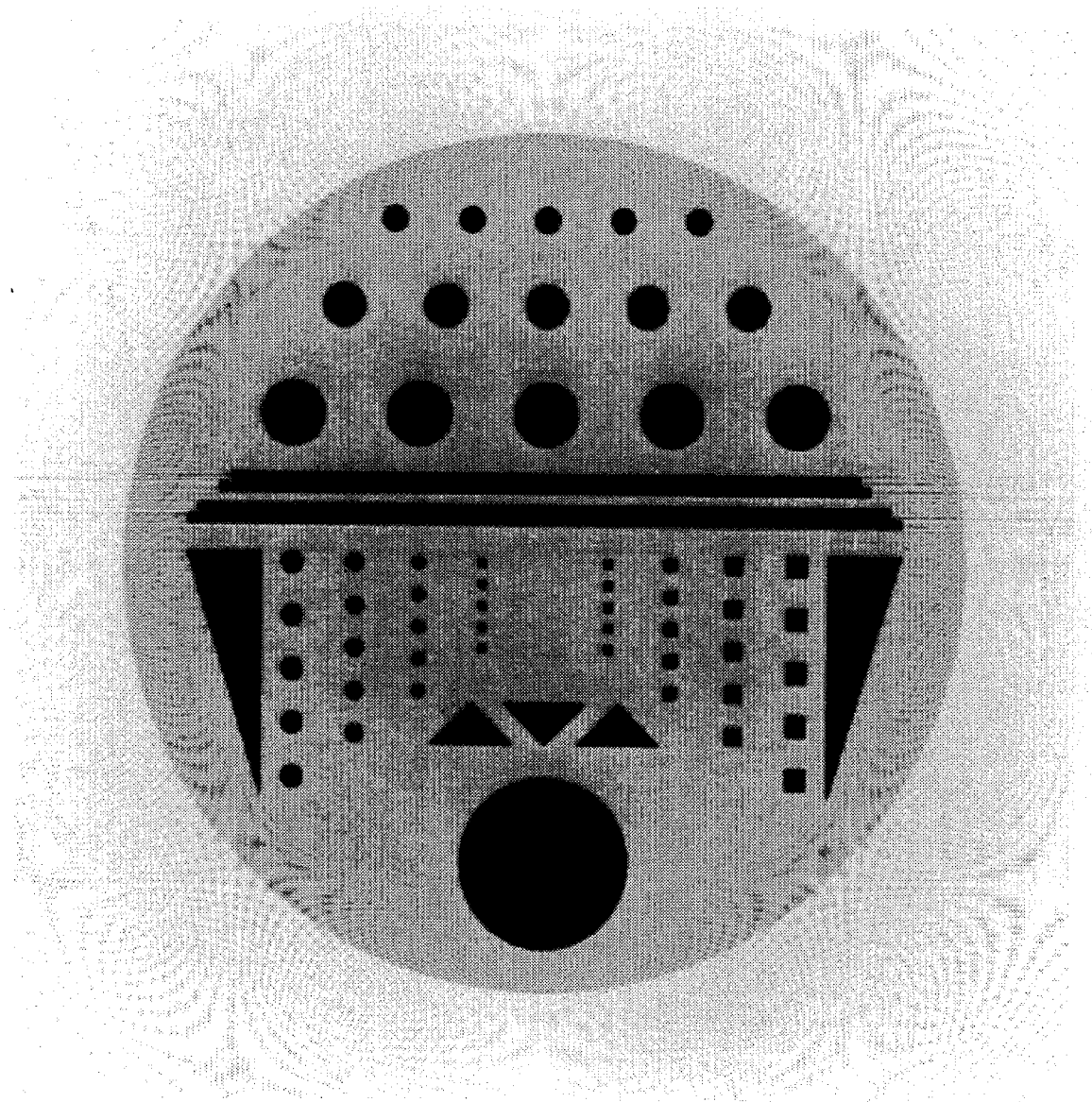

FIG. 13 depicts reconstructions from partially redundant projection data. The boundaries between the inner and outer portions of the reconstructed image (i.e., the regions associated with redundant and non-redundant projection data) are clearly visible in FIG. 13a, 13b, and 13c. Table 4 gives the rms-error and correlation for various redundancy coefficients in reconstructions from partially redundant projections, compared with a reconstruction from ideal fan beam projection data. The relatively poor image quality for a redundancy coefficient $\eta=0.8$ is caused by the introduction of the discontinuity between the redundant and non-redundant portions in the projection data, and is attributed to the discrete implementation of the reconstruction algorithm.

TABLE 4

Rms-error and correlation in reconstructions from partially redundant projection data

| Redundancy | $\eta = 1.0$ | $\eta = 0.8$ | $\eta = 0.6$ | $\eta = 0.4$ | $\eta = 0.2$ | $\eta = 0.0$ |
|---|---|---|---|---|---|---|
| $\tilde{r}_0/\tau_0$ | 2.0 | 1.8 | 1.6 | 1.4 | 1.2 | 1.0 |
| $\tilde{r}_0'/\tau_0$ | 0.0 | 0.2 | 0.4 | 0.6 | 0.8 | 1.0 |
| RMS-Error | 0.15929 | 0.17908 | 0.09024 | 0.08990 | 0.04186 | 0.00000 |
| Correlation | 0.87006 | 0.84404 | 0.95235 | 0.95267 | 0.98922 | 1.00000 |

Section 3.4 - - - Synthetic Scanner Arrays

Figures 14A, 14B:
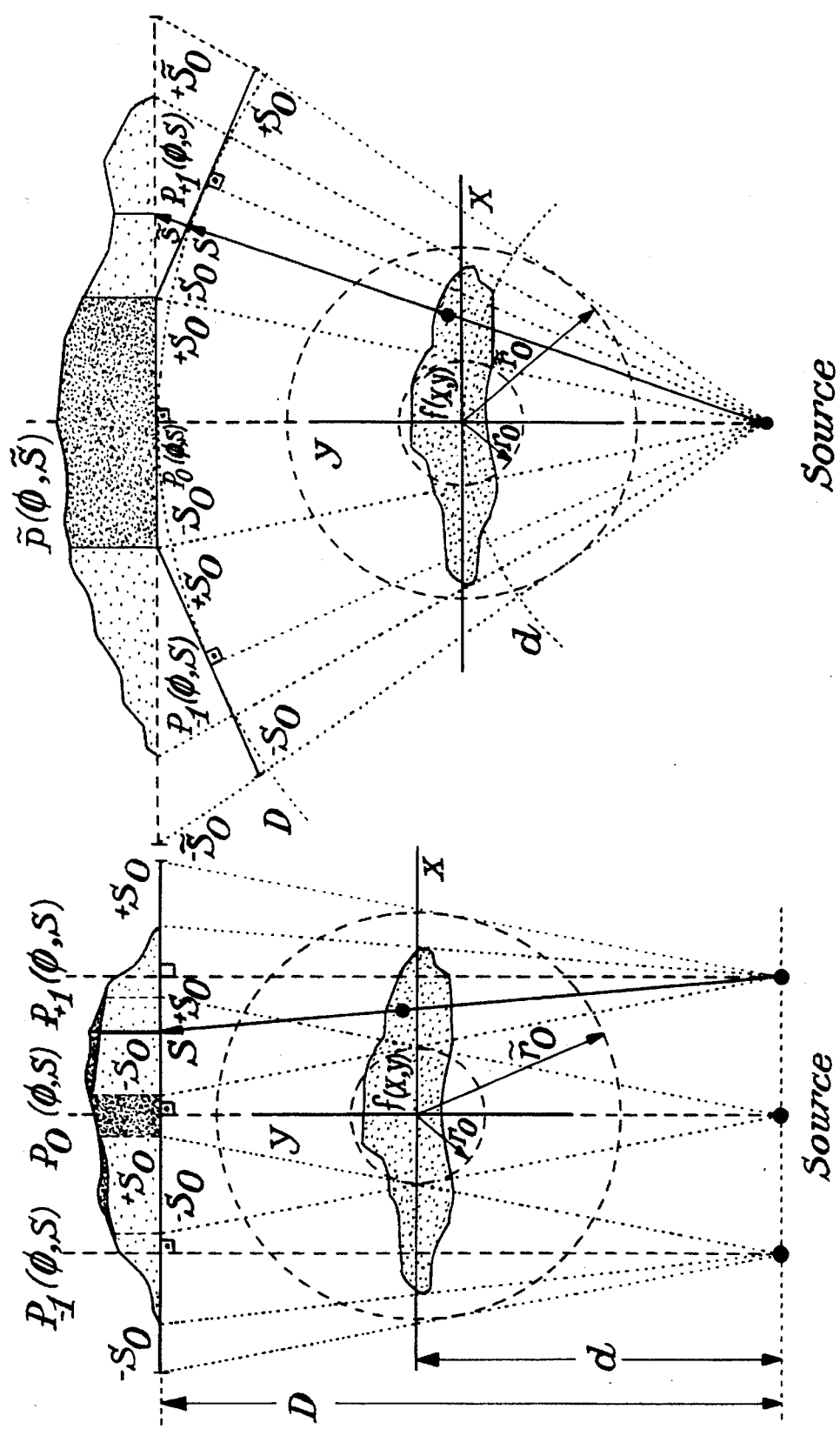
FIG. 14 shows two diagrams (view from above) which illustrate the geometry of synthetic scanner arrays. The three partial projections cover the projection space and result in an extension of the artifact-free zone from $r_o$ to $\tilde{r}_o$. In (a), a linear synthetic scanner array is shown. In (b), a circular synthetic scanner array is shown.

An important limitation in tomography, in particular in industrial applications, is the limited size of the detector. We have shown elsewhere [M. Müller, G. R. Arce, and R. A. Blake Jr.; "Truncated Projection Artifacts and Reconstruction in Computerized Tomography", submitted to *IEEE Transactions on Image Processing*.] that truncation artifacts in tomographic reconstructions due to projections horizontally extending over the detector boundaries are easily explained, and we have proposed an exact deterministic method of accurate and truncation artifact-free reconstruction of objects arbitrarily larger than the available detector screen. The method of the present invention collects partial projection data of concentric portions of the object, which is resorted into a complete virtual set of projections prior to reconstruction. Since the resorted virtual projection data is in theory indistinguishable from a set of projections recorded with a sufficiently large detector, depending on the rebinning mode we apply a standard parallel or fan beam reconstruction method to recover an image. In [M. Müller, G. R. Arce, and R. A. Blake Jr.; "Truncated Projection Artifacts and Reconstruction in Computerized Tomography", submitted to *IEEE Transactions on Image Processing.*] we have shown that both linear and circular synthetic scanner arrays are exact and easily implemented methods for arbitrary extension of the artifact-free zone, and we have applied both methods to three-dimensional cone beam geometry [M. Müller and G. R. Arce, "The Cone Beam Algorithm and Synthetic Scanner Arrays in Three-Dimensional Computerized Tomography", technical report in the Department of Electrical Engineering at the University of Delaware, 1993.]. FIGS. 14a and 14b depict the geometry of linear and circular synthetic fan beam scanner arrays.

We are first considering the application of the universal fan beam algorithm to linear synthetic fan beam scanner arrays, and subsequently treat the alternative method of circular scanner arrays. As shown in FIG. 14, for each of the three partial sets of projections the scanner is displaced by a precisely determined horizontal shift $\Delta_x = 2ks_0 d/D$ (note that an opposite object displacement is equivalent), where the partial projection data is then recorded while rotating the object over a full circle. After having acquired all three partial sets of projections, we resort the truncated partial sets of projections into a virtual set of projections, which will be complete. The geometry of linear scanner arrays suggests resorting into virtual parallel beam projection data, such that we subsequently reconstruct the virtual data with a standard parallel beam algorithm.

For completeness, we present the mathematics involved in linear scanner arrays without derivation. The mathematically interested reader is referred to [M. Müller, G. R. Arce, and R. A. Blake Jr.; "Truncated Projection Artifacts and Reconstruction in Computerized Tomography", submitted to *IEEE Transactions on Image Processing.*; M. Müller and G. R. Arce, "The Cone Beam Algorithm and Synthetic Scanner Arrays in Three-Dimensional Computerized Tomography", technical report in the Department of Electrical Engineering at the University of Delaware, 1993.]. Note that all new parameters are determined solely from the scanner geometry (i.e., the source-to-object and source-to-detector distances d and D respectively), the detector width $2s_o$, and from the desired radius $\tilde{r}_0$ of the virtual artifact-free zone. Recall that the radius of the physical artifact-free zone in fan beam scanners is $r_0 = s_0 d/\sqrt{D^2 + s_0^2}$. The number of partial sets of projections required to yield the desired virtual artifact-free zone is computed as $N = \lceil (\tilde{r}_0 \sqrt{D^2 + s_0^2}/(s_0 d) - 1)/2 \rceil$, and the horizontal displacements for the partial scans are thus $\Delta_{s,x} = 2ks_0 d/D$ for $k = -N \ldots 0 \ldots +N$. The symbol "⌈ ⌉" (hereinafter referred to as "half-brackets") means that the value of the number within the half-brackets is rounded up to the next largest integer (i.e., 2.2 would be rounded up to 3). The partial sets of fan beam projections $p_k$ are resorted into a complete virtual set of parallel beam projections $\tilde{p}_k$ as $\tilde{p}_k(\phi,\tilde{s}) = p_k(\phi + \arctan(s/D), s)$ where $s = (-2ks_0 d^2 + \tilde{s}\sqrt{4k^2 s_0^2 d^2 + D^2(d^2 - \tilde{s}^2)})/(d^2 - \tilde{s}^2)$ with $-\tilde{r}_0 \leq \tilde{s} \leq +\tilde{r}_0$ the virtual detector coordinate and $k = [\tilde{s}\sqrt{D^2 + s_0^2}/(2s_0 d)]$. Note that the symbol "[ ]" (hereinafter referred to as brackets) means that the value of the number within the brackets is rounded to the nearest integer (i.e., 2.4 would be rounded to 2 and 2.6 would be rounded to 3). With $\tilde{p}_k(\phi,\tilde{s})$ the $k^{th}$ patch of the virtual set of parallel beam projections as in $$\tilde{p}(\phi,\tilde{s}) = \sum_{k=-N}^{+N} \tilde{p}_k(\phi,\tilde{s}),$$

we finally have $\tilde{p}(\phi,\tilde{s})$ denoting the complete virtual set of parallel beam projections.

Figure 15A:
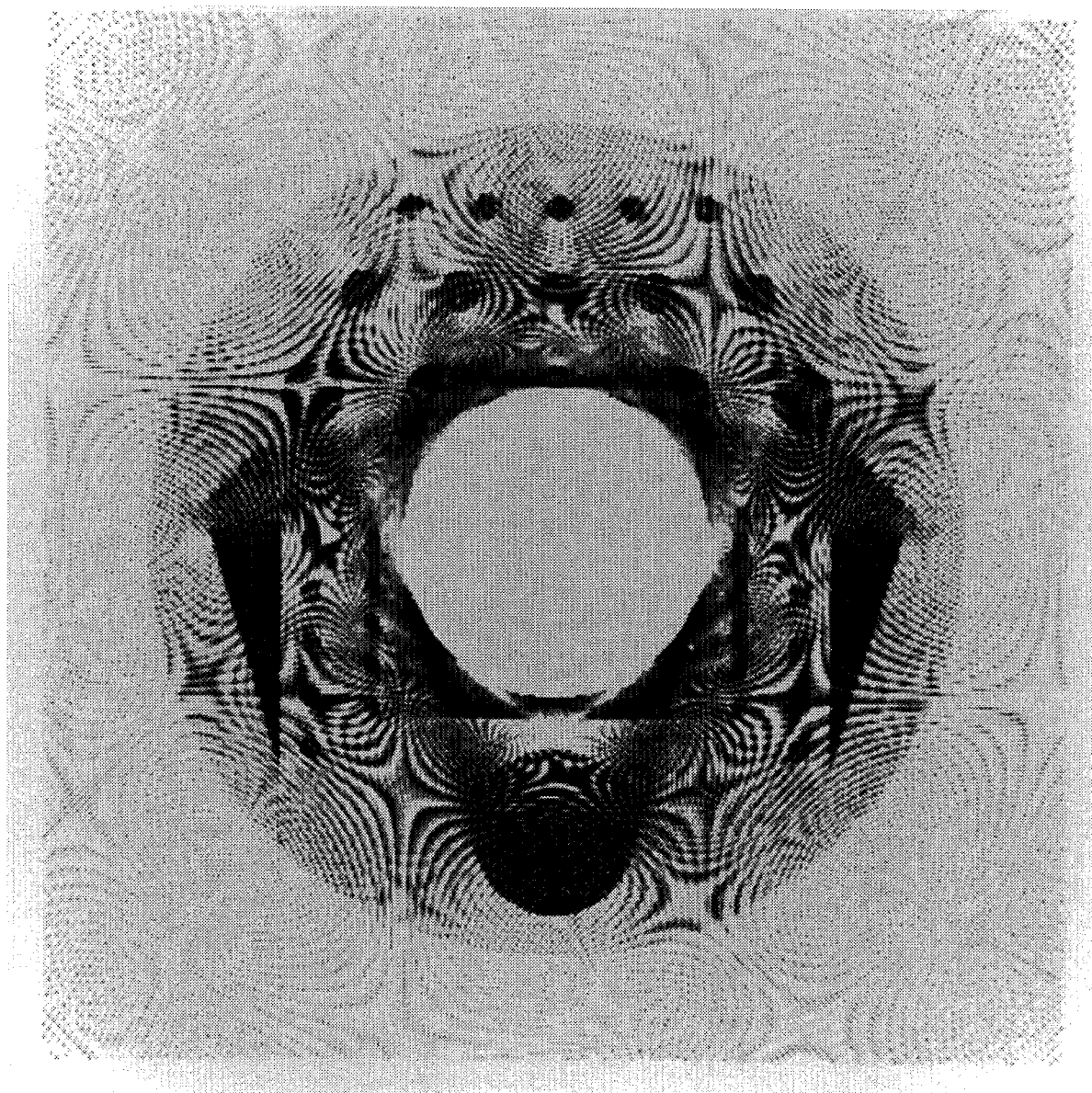
FIG. 15 shows synthetic scanner arrays and reconstruction of partial sets of projections. In (a), a partial reconstruction from the left-hand set of projections is shown. In (b), a partial reconstruction from the center set of projections is shown. In (c), a partial reconstruction from the right-hand set of projections is shown. In (d), a final image obtained through superposition of the partial reconstructions is shown. Fan spread angle 8.578°. In (e), a final image is shown with fan spread angle reduced to 2,864°. In (f), a final image is shown with fan spread angle reduced to 0.689°.
Figure 15B:
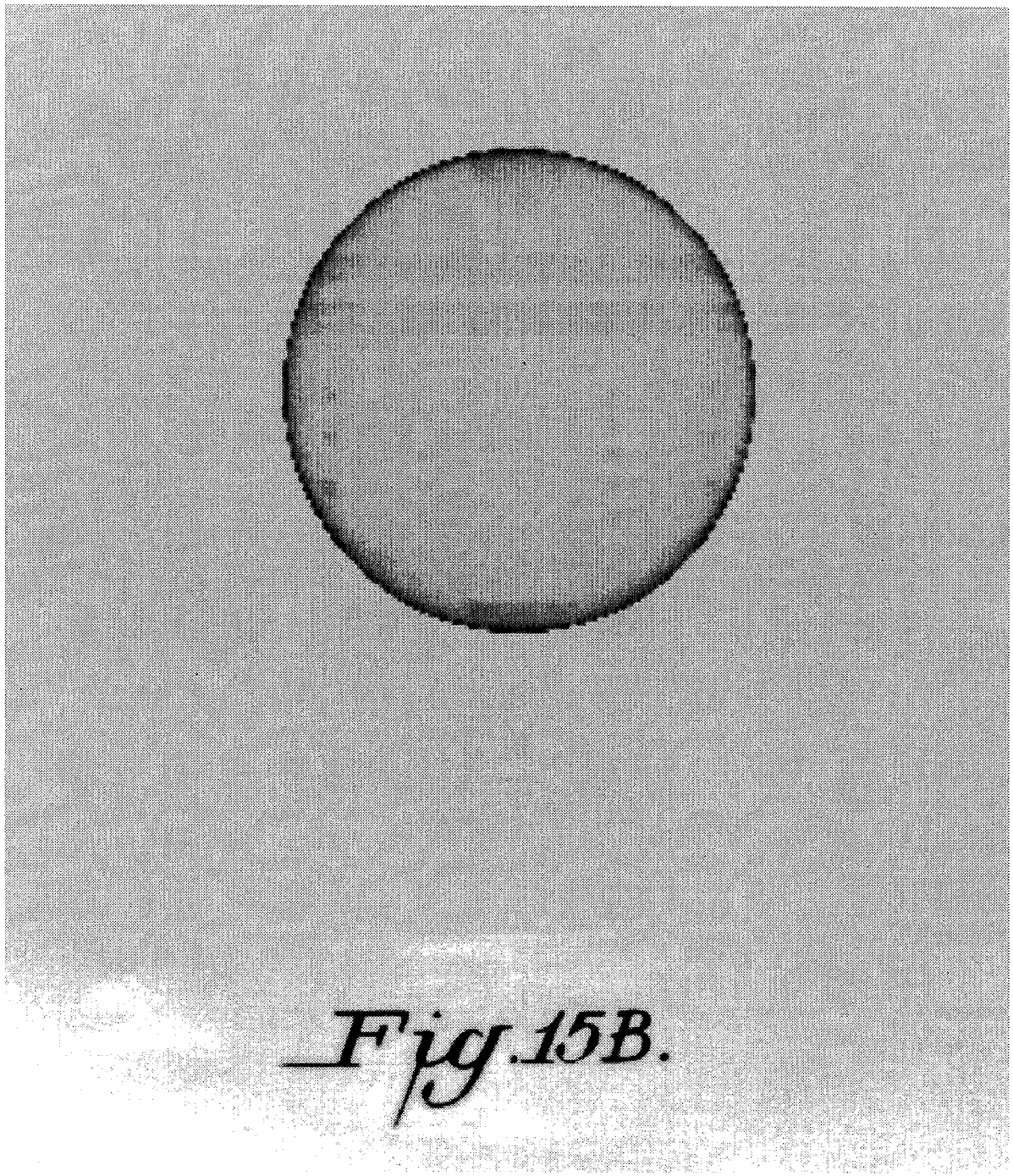
Figure 15C:
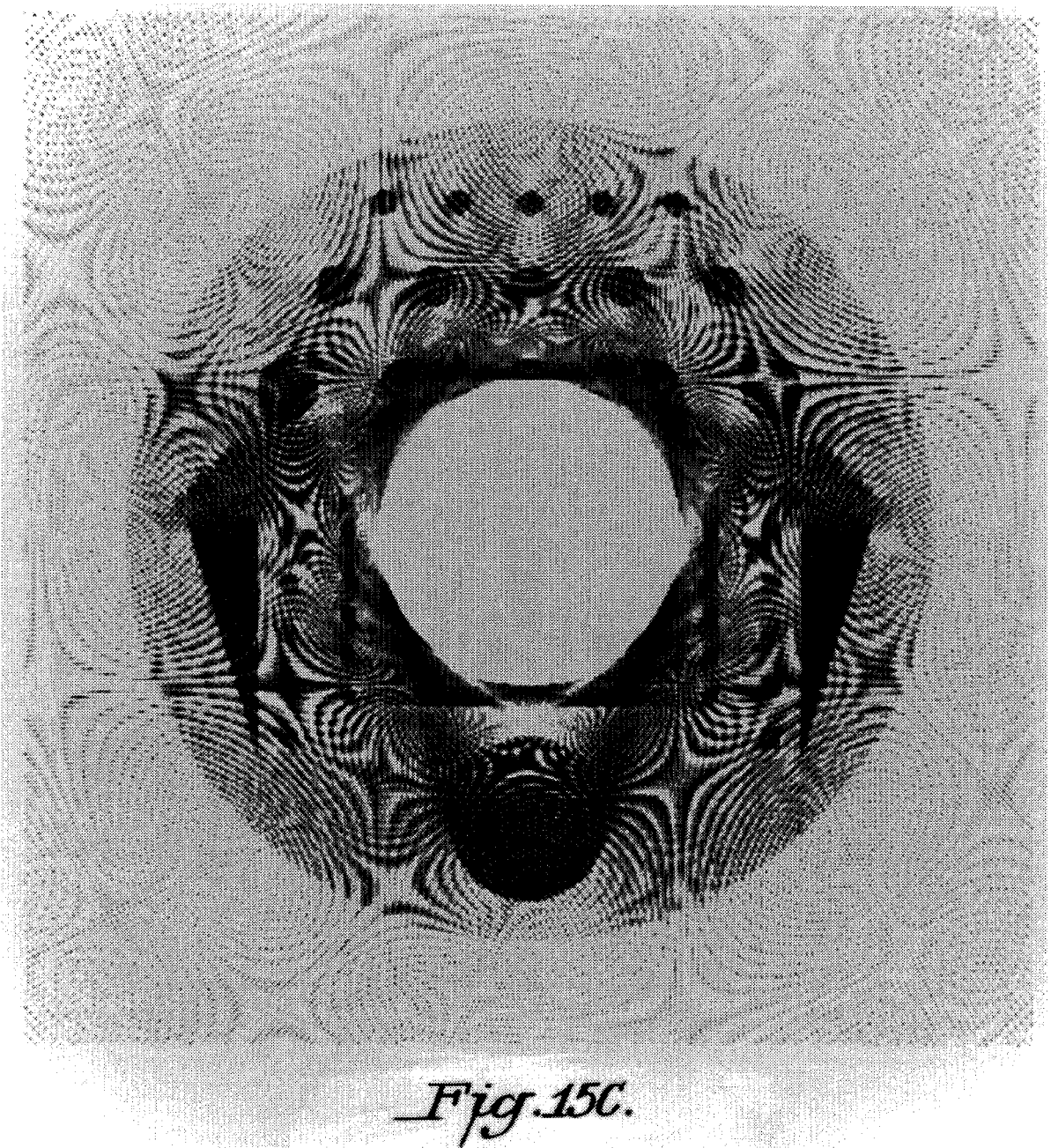
Figure 15D:
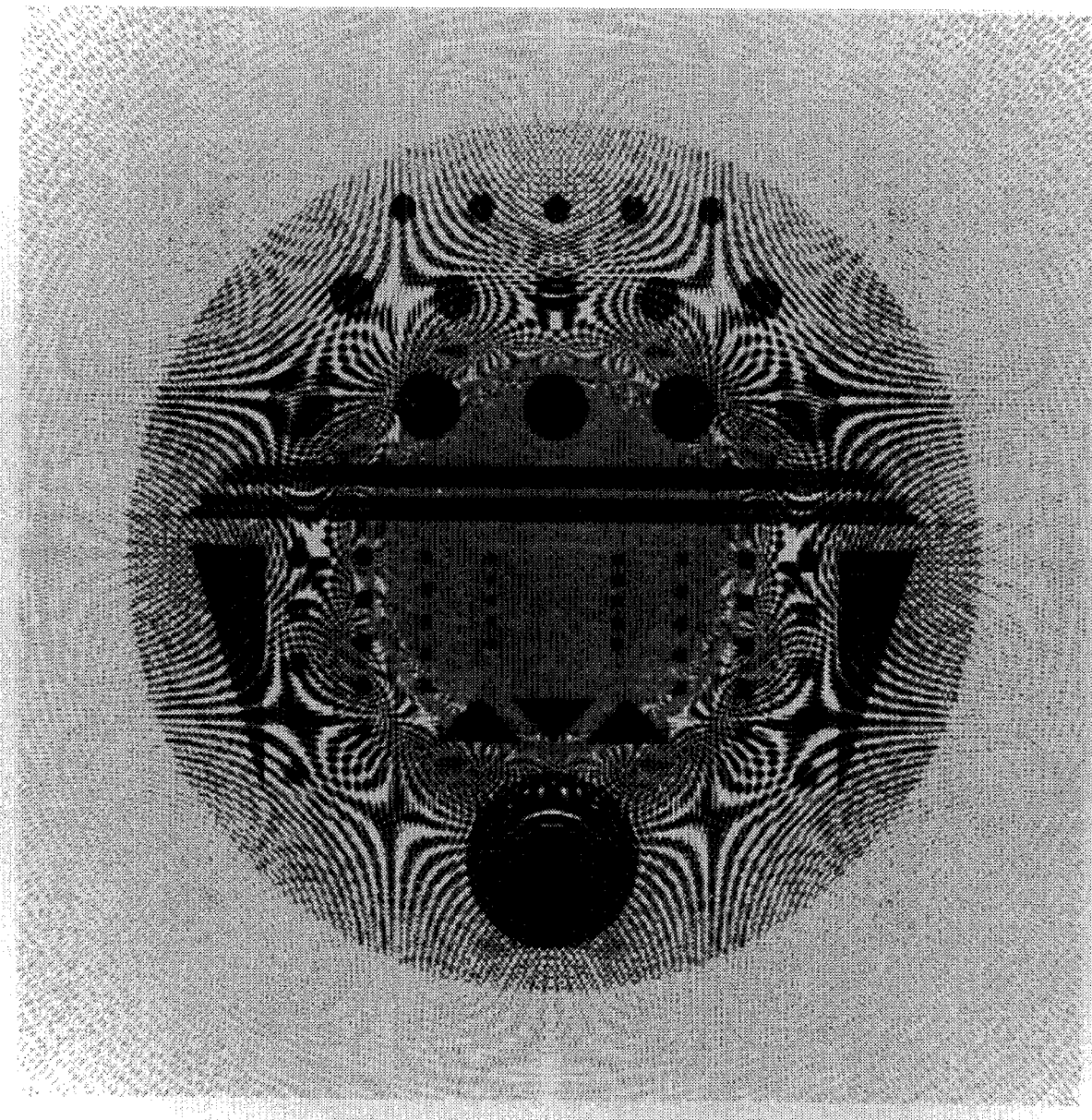

Although the preprocessing algorithm revisited above yields excellent results, it incorporates interpolation and sampling operations such that the virtual projection data retains only approx. 50% of the projection resolution originally inherent in the partial scans. However, in some applications of synthetic scanner arrays limited resolution may not be a problem since we already increase the total resolution through combination of partial scans. We next apply the new universal fan beam algorithm to linear synthetic fan beam scanner arrays. Here we immediately reconstruct partial images from the partial projection data, such that the final image is obtained by superposition of all partial reconstructions. Due to the linearity of the reconstruction operator, truncation artifacts in reconstructions from the incomplete partial scans will cancel out in the superposition. We apply the scanner shift for linear arrays to equation (17) and obtain an algorithm for immediate reconstruction of partial images from partial fan beam projection data $$f_k(x,y) = \frac{D}{2} \int_0^{2\pi} \frac{1}{(y'+d)^2} \int_{-\infty}^{+\infty} \frac{dD - 2kss_0 \frac{d}{D}}{\sqrt{D^2 + s^2}} p_k(\phi,s) h_w\left(\frac{D\left(x' - 2ks_0 \frac{d}{D}\right)}{y'+d} - s\right) ds\, d\phi \quad (22)$$

for $k = -N \ldots 0 \ldots +N$ with the number of partial scans N as defined earlier. Although the individual sets of partial projections are severely truncated (and thus incomplete) and center-displaced, the new algorithm utilizes the information contained in the partial data optimally and yields intelligible partial images, as illustrated in FIG. 15a. through 15c. As shown in FIG. 15d, the superposition of the partial images yield the final image free of truncation artifacts. Although the deviation from the ideal image is considerable and prohibits quantitative interpretation of the reconstruction, the results clearly display the features without obscuring the object by truncation artifacts. Table 5 gives the rms-error and correlation in images obtained through superposition of partial reconstructions, compared with a reconstruction from ideal fan beam projection data.

TABLE 5

Rms-error and correlation in images obtained through superposition of partial reconstructions from truncated projections for various fan spread angles.

| Fan Spread Angle | 8.578 deg | 5.725 deg | 2.864 deg | 1.719 deg | 0.689 deg |
|---|---|---|---|---|---|
| RMS-error | 0.46338 | 0.37108 | 0.18240 | 0.10689 | 0.10121 |
| Correlation | 0.52584 | 0.61022 | 0.84038 | 0.93563 | 0.94153 |

Figure 15E:
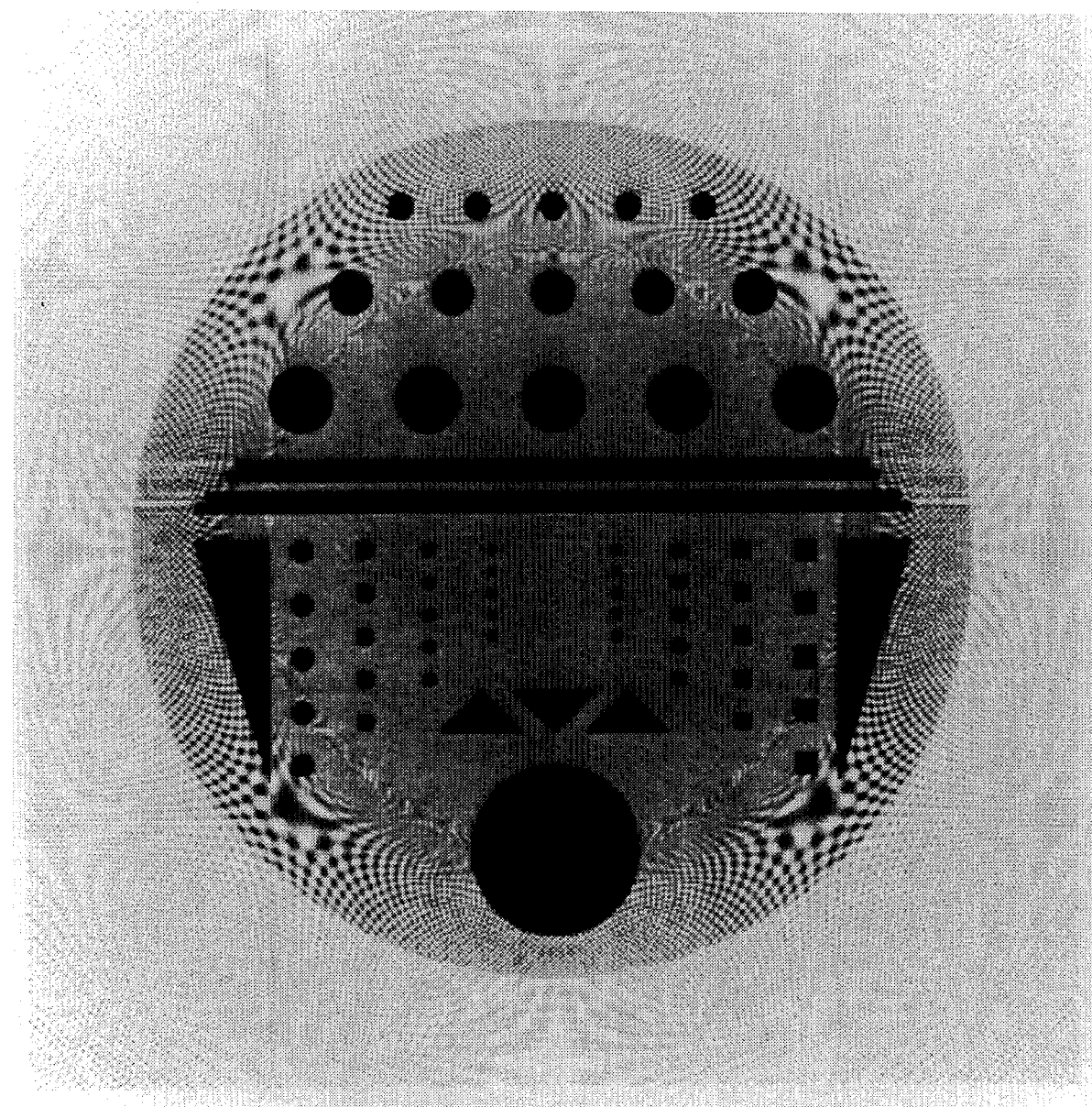
Figure 15F:
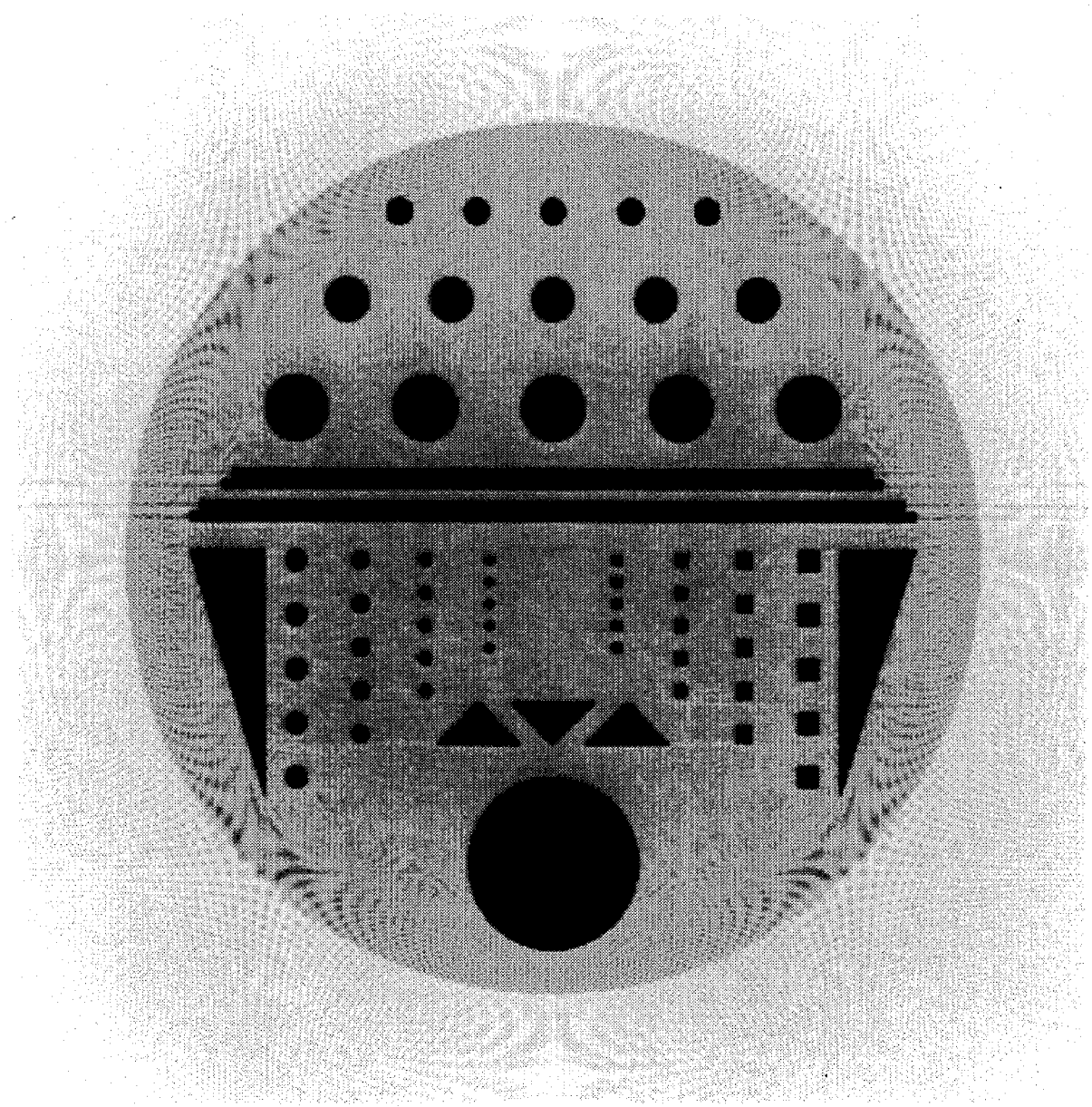
Figure 16A:
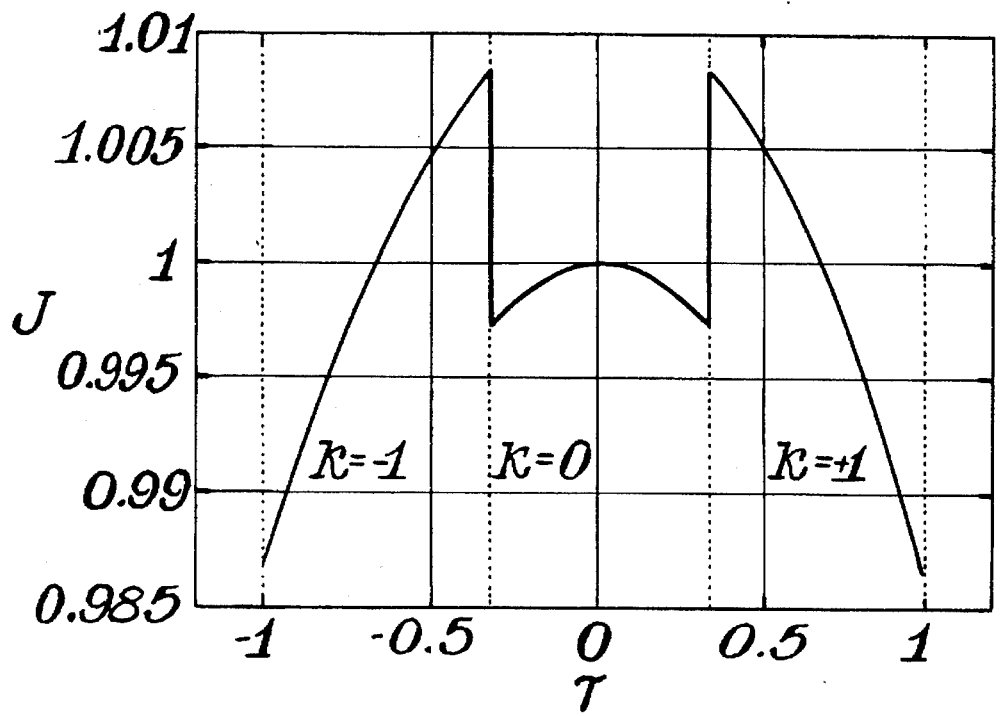
FIG. 16 shows plots of the Jacobian $J(\tau)$ as a function of the ray displacement $\tau$ for synthetic fan beam scanner arrays with three partial scans. The vertical dashed lines delimit the range of the individual partial scans. The horizontal dashed-dotted line depicts the Jacobian for parallel beam geometry. 16(a) shows a linear array. 16(b) shows a circular array.

The residual artifacts still visible in the final image are due to the discontinuous Jacobian J for linear synthetic scanner arrays. In equation (9) the Jacobian appears as a weighting factor for the projection data $p(\phi,s)$, which is assumed to be a smooth function. A discontinuous Jacobian results in a discontinuous weighted projection, which causes severe ringing artifacts due to the band limited convolution filter $h_w$. The discontinuities in the Jacobian and thus the residual ringing artifacts in the final image depend on the spread angle of the fan beam used for projection. The artifacts are reduced by placing the source further from the source/detector, such that the rays appear more and more parallel, as shown in FIG. 15e, 15f, and Table 5. In the limit, as the source is moved to a location infinitely far from the object, the rays become parallel and the aliasing artifacts in FIG. 15d, 15e, and 15f completely vanish. Improvements on the image quality are also achieved either by modifying the impulse response of the convolution filter, or by changing the projection geometry so as to obtain a smoother Jacobian J. FIG. 16 depicts the Jacobian J for linear and circular synthetic scanner arrays.

Figure 16B:
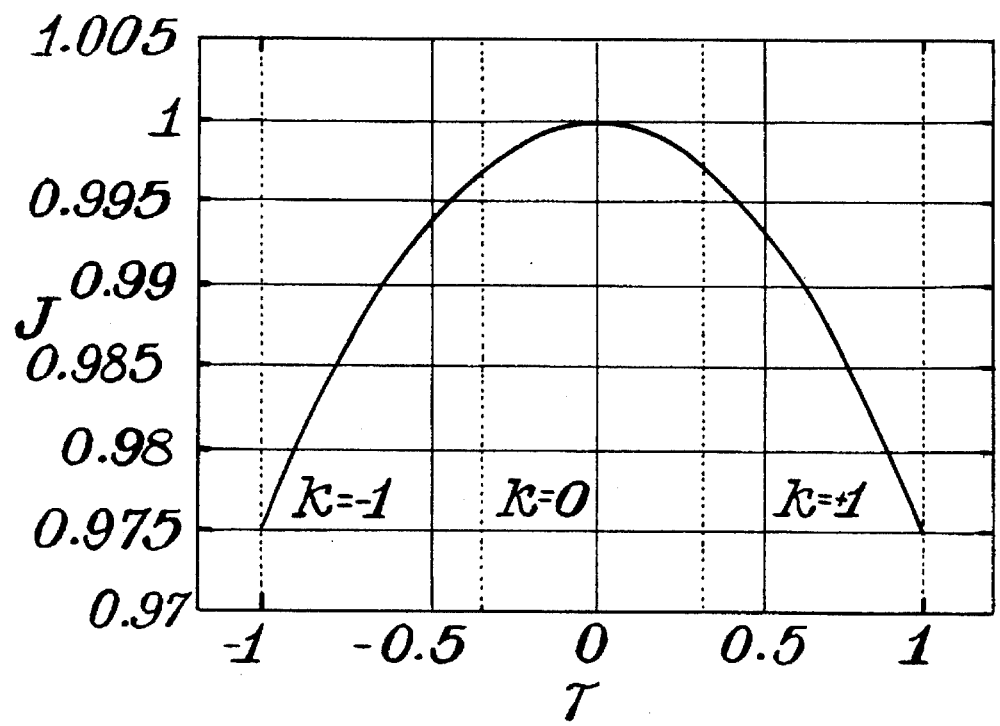

As shown in FIG. 16b, the geometry in circular arrays yields a continuous and smooth Jacobian, which is far better suited for application of the universal fan beam algorithm. Circular synthetic fan beam scanner arrays have been described in detail in [M. Müller, G. R. Arce, and R. A. Blake Jr.; "Truncated Projection Artifacts and Reconstruction in Computerized Tomography", submitted to *IEEE Transactions on Image Processing*.], where we propose a preprocessing algorithm to resort the set of truncated partial fan beam scans into a virtual set of fan beam projections, which is complete. Subsequently, an image is recovered from the virtual data with a standard fan beam reconstruction algorithm. We next briefly revisit the mathematics involved in circular fan beam scanner arrays.

Recall that the number of partial sets of projections required to yield the desired virtual artifact-free zone is computed as $N=\lceil(\arcsin(+e, otl_{0+ee}/d)/\gamma-1)/2\rceil$. The detector displacements for the partial scans are thus $\Delta_{s,d}=D\sin(2k\gamma)$ and $\Delta_{d,y}=D\cos(2k\gamma)$ with the detector rotations $\psi_d=2k\gamma$ for $k=-N \ldots 0 \ldots +N$. Here we have set $\gamma=\arctan(s_0/D)$. Note that the detector placement with $\Delta_{d,x}$, $\Delta_{d,y}$, and $\psi_d$ is equivalent to a more practical object placement as $\Delta_x=-d\sin(2k\gamma)$ and $\Delta_y=d(\cos(2k\gamma)-1)$ with an object rotation $\beta=2k\gamma$. The partial sets of fan beam projections $P_k$ are resorted into a complete virtual set of fan beam projections $\tilde{p}_k$ as $\tilde{p}_k(\phi,\tilde{s})=p_k(\phi, D(\tilde{s}-D\tan(2k\gamma))/(D+\tilde{s}\tan(2k\gamma)))$ with $|\tilde{s}| \leq D\tilde{r}_0/\sqrt{d^2-+e, otl_{0+ee}}$ the virtual detector coordinate and $k=[\arctan(\tilde{s}/D)/(2\gamma)]$. With $\tilde{p}_k(\phi,\tilde{s})$ the kth patch of the virtual set of fan beam projections as in $$\tilde{p}(\phi,\tilde{s}) = \sum_{k=-N}^{+N} \tilde{p}_k(\phi,\tilde{s}),$$

we finally have $\tilde{p}(\phi,\tilde{s})$ denoting the complete virtual set of fan beam projections.

Figure 17A:
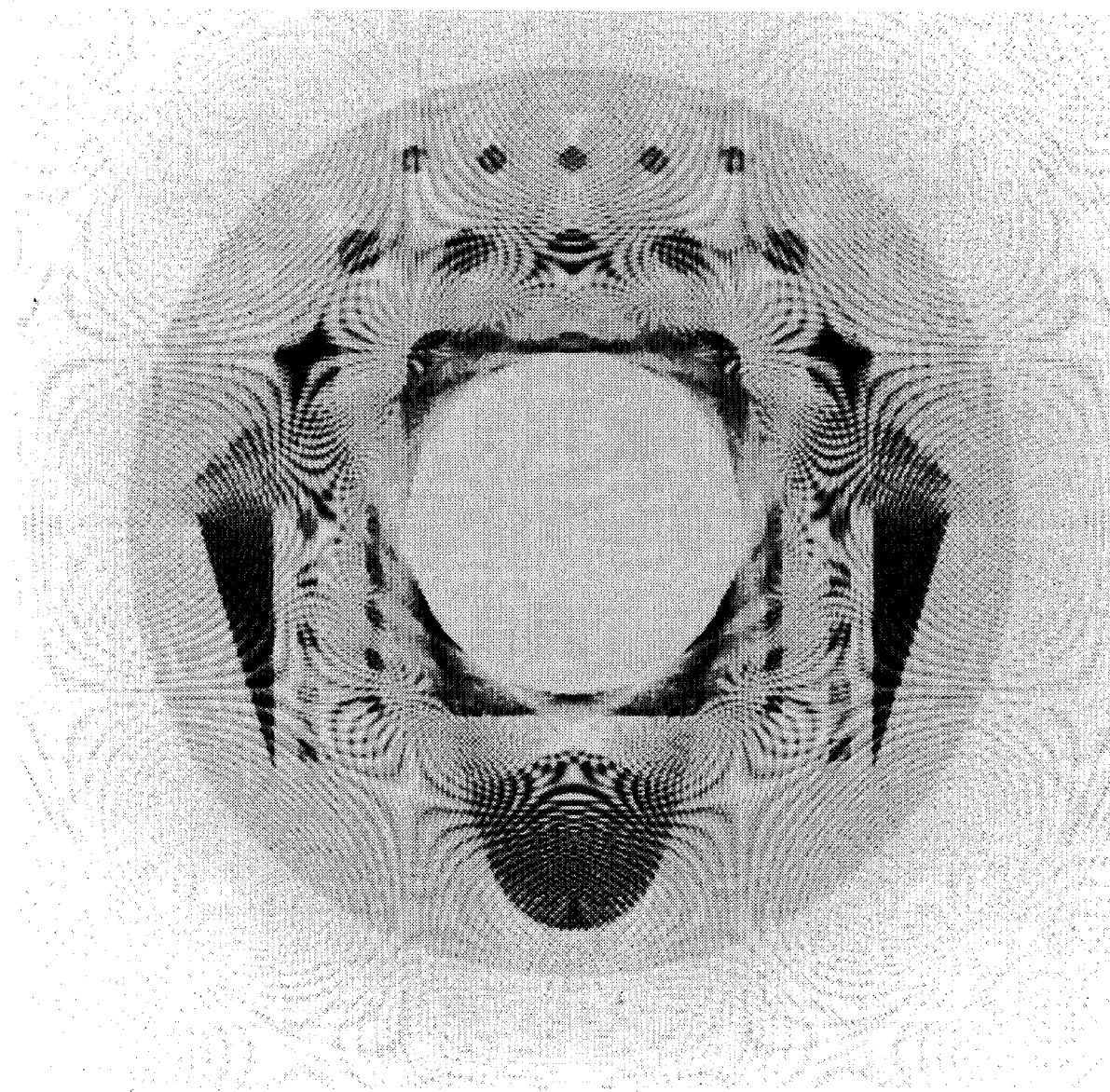
FIG. 17 shows reconstructions from partial projection data in a circular scanner array with three partial scans (N=1). 17(a) shows superposition of the left and right hand reconstructed partial projection data. 17(b) shows reconstruction of the center partial projection data. 17(c) shows the final image through superposition of the partial constructions.
Figure 17B:
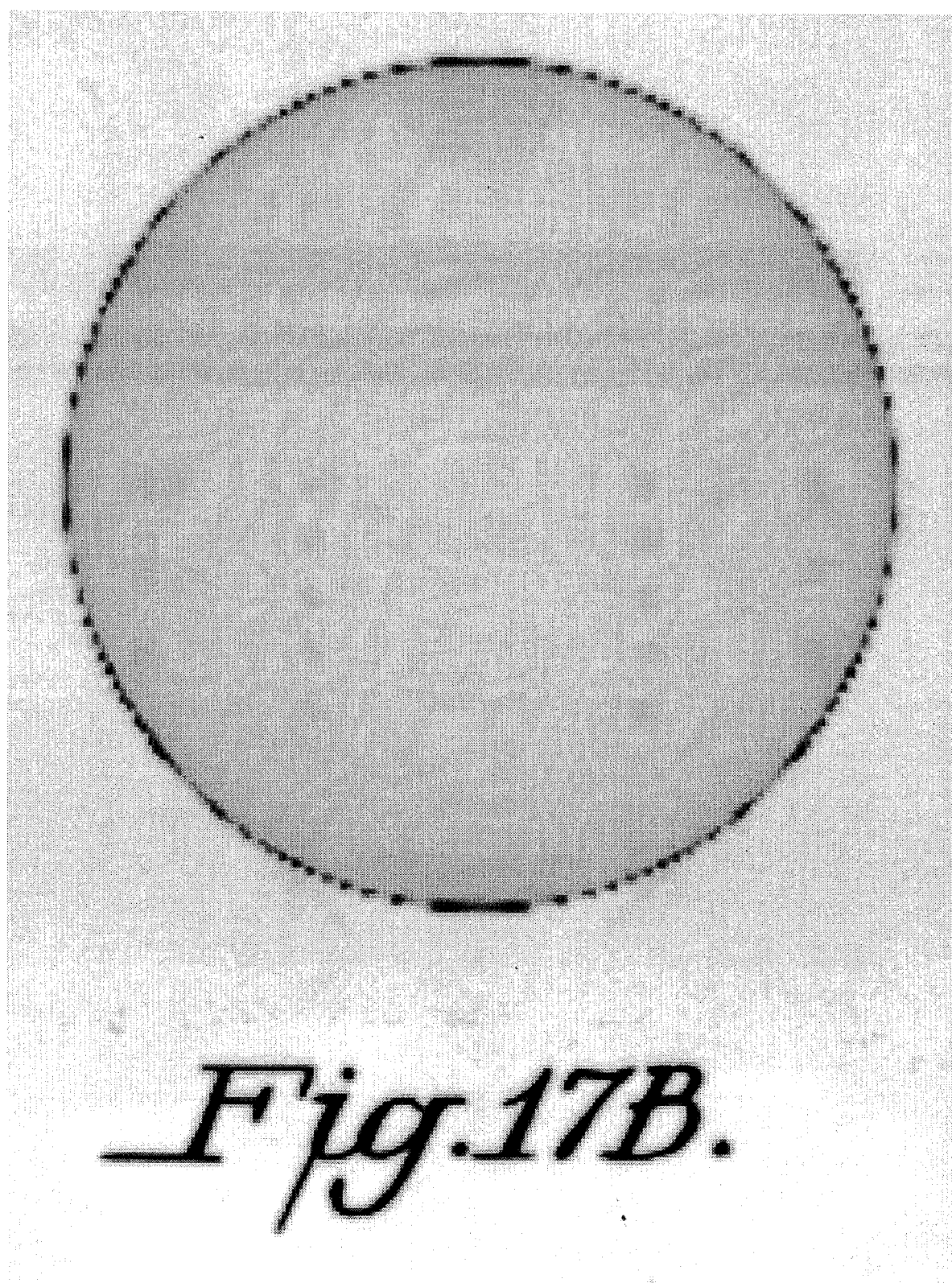
Figure 17C:
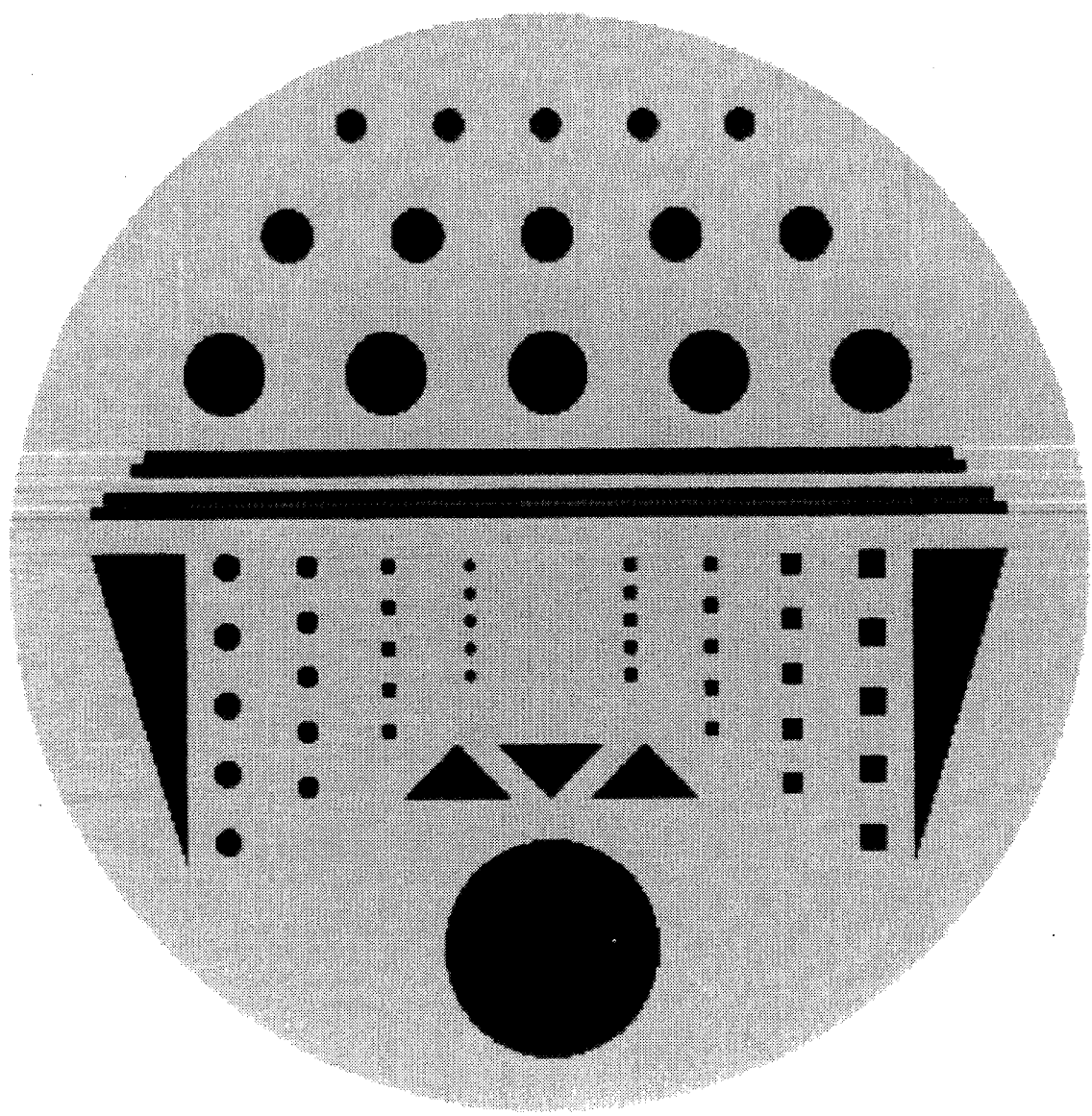
Figure 18A:
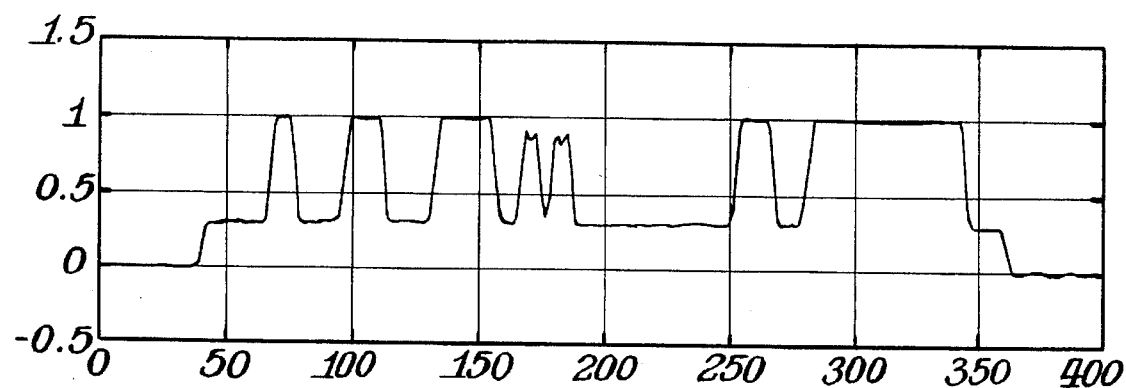
FIG. 18 shows resolution in images reconstructed from partial projection data due to circular synthetic fan beam scanner arrays. 18(a) shows a profile of the image through resorting method. 18(b) shows the image through resorting method. 18(c) shows a profile of the image through the method of partial reconstruction. 18(d) shows the image through the method of partial reconstruction.
Figure 18C:
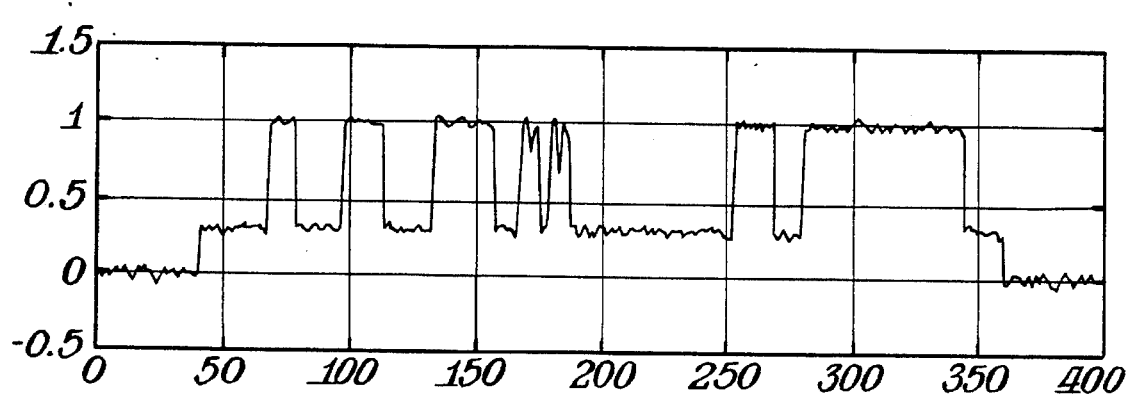
Figure 18B:
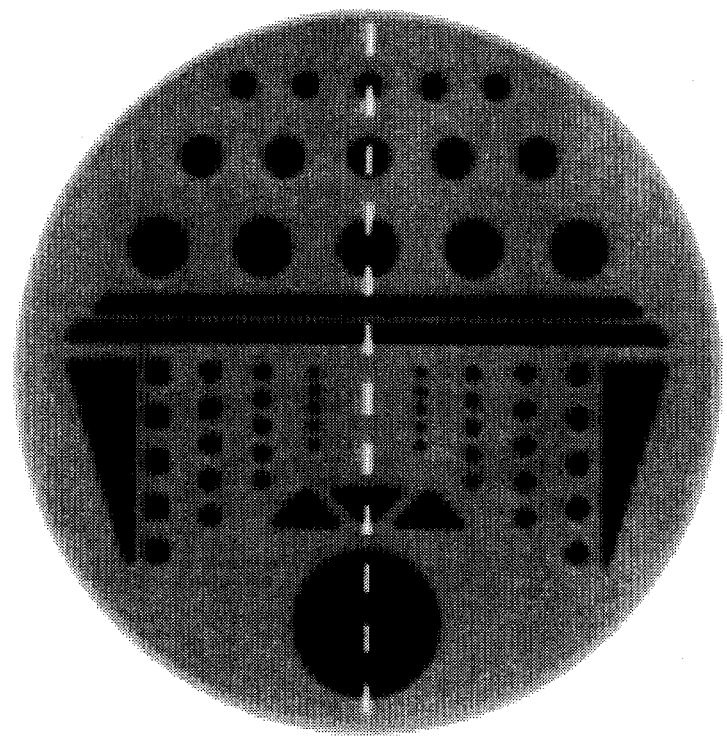
Figure 18D:
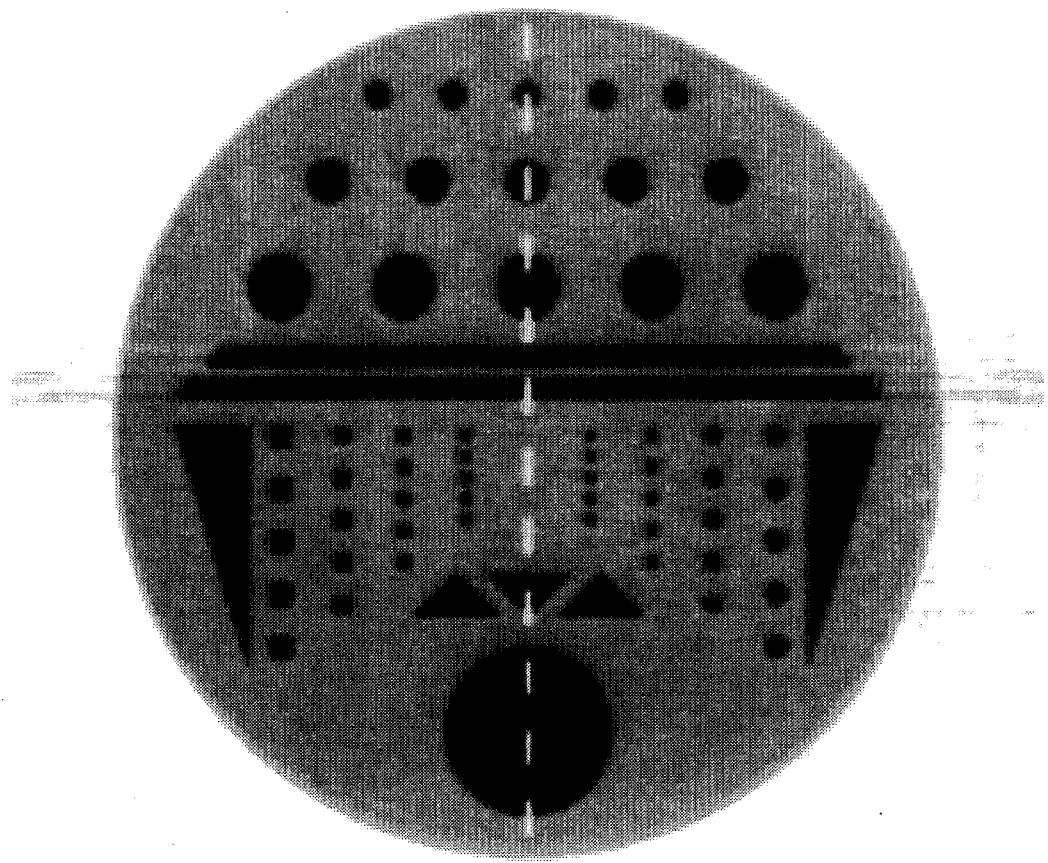

However, as mentioned before, the inherent interpolation and sampling operations in the preprocessing algorithm reduce the effective resolution of the virtual data by up to 50%. Thus, for employment of detectors with low resolution we recommend immediate reconstruction of partial scans and subsequent superposition, rather than resorting the partial data and reconstructing the resulting virtual scan. Applying the universal fan beam algorithm in equations (8) and (9) immediately to the partial projection data yielded by a circular scanner array, we obtain the final image through superposition of the partial reconstructions. FIG. 17 depicts the partial and final reconstructions due to a circular synthetic scanner array. Table 6 gives the rms-error and correlation of images obtained through superposition of partial reconstructions in a circular scanner array, compared with a reconstruction from ideal fan beam data. The differences in rms-error and correlation between the preprocessing approach and the method of partial reconstruction are minimal. Table 17 in the Appendix shows that application of smoothing during reconstruction of the partial scans in a circular scanner array substantially improves the quality of the resulting images in terms of rms-error and correlation.

TABLE 6

Rms-error and correlation in images obtained with a circular fan beam scanner array with a spread angle of 8.578 deg.

| Method | Preprocessing/ Resorting | | Partial Reconstruction | |
|---|---|---|---|---|
| Resolution $N_\phi \times N_3$ | $201^2$ | $601^2$ | $201^2$ | $601^2$ |
| RMS-Error | 0.04850 | 0.03532 | 0.08615 | 0.03623 |
| Correlation | 0.98557 | 0.99237 | 0.95712 | 0.99224 |

Table 6 suggests the preprocessing approach as the superior reconstruction method for circular scanner arrays. The profiles through the vertical center of the images in FIG. 18, however, reveal the higher resolution in images due to the method of partial reconstruction.

Section 4 - - - Resolution Enhancement and Microtomography

In the previous sections we have utilized the ability of the universal fan beam algorithm to account for displacements in the projection data. The application to circular synthetic scanner arrays in addition required the option of tilting the detector. Now, we will use the ability to reconstruct from projections onto a tilted detector to obtain a novel method of resolution enhancement in microtomography.

As illustrated in FIG. 3, tilting the detector spreads the projection of a small object over a larger portion of the detector, thus covering more sensors and providing more measurements than with a straight detector. We obtain an algorithm for the reconstruction from projections onto tilted detectors by considering only the detector tilt angle $\psi_d$ in equations (8) and (9), $$f(x,y) = \frac{dD\cos(\phi_d)}{2} \int_0^{2\pi} \frac{1}{((y'+d)\cos(\psi_d)+x'\sin(\psi_d))^2} \int_{-\infty}^{+\infty} \frac{D+s\sin(\psi_d)}{\sqrt{D^2+s^2+2Ds\sin(\psi_d)}} \times p(\phi,s)h_w\left(\frac{Dx'}{((y'+d)\cos(\psi_d)+x'\sin(\psi_d))^2}\right) ds\, d\phi \quad (23)$$

with x' and y' as defined before. Note that the projection tail on the side of the tilted detector pointing away from the source we have a larger stretch factor than on the opposite side, leading to an uneven illumination of the detector. We therefore shift either just the detector or the entire scanner until the magnified projection appears centered on the detector. This technique allows us to optimally magnify the projections of objects fitting inside an arbitrary artifact-free zone while avoiding truncations. The algorithm for optimal reconstruction from projections onto tilted detectors has to take into account the necessary horizontal scanner shift to center the stretched fan beam projections by augmenting equation (23) by the additional parameter $\Delta_{d,x}$ or $\Delta_{s,x}$. Defining the magnification M as the stretch factor associated with the ray in the center of the fan (or equivalently a parallel beam scanner with a tilted detector) we relate the detector tilt angle $\psi_d$ with the magnification M as $$M \cos(\psi_d) = 1 \qquad (24)$$

For a practical implementation, we choose to optimize utilization of the tilted detector by center-displacing the scanner, since a horizontal scanner shift is also required for single-sided and partially redundant tomography, and for synthetic scanner arrays. Thus, we simplify the ray displacement defined in (5) by only regarding the detector tilt $\psi_d$ and the horizontal scanner shift $\Delta_{s,x}$. We obtain an expression for the maximum ray displacements associated with the outermost rays in the fan by regarding the detector boundaries $\pm s_o$ $$\tau(\Delta_{s,x}, \psi_d) = \frac{\Delta_{s,x} D \pm s_0(d \cos(\psi_d) + \Delta_{s,x} \sin(\psi_d))}{\sqrt{D^2 + s_0^2 \pm 2 s_0 D \sin(\psi_d)}}. \qquad (25)$$

For resolution enhancement of projections of an object fitting into an artifact-free zone of radius $\tilde{r}_0$, we require $-\tilde{r}_0 \leq \tau(\Delta_{s,x}, \psi) \leq +\tilde{r}_0$, where for a given magnification M and thus tilt angle $\psi_d$ we center the projections by choosing $\Delta_{s,x}$ such that $\tilde{r}_0 - |\tau(\Delta_{s,x}, \psi_d)|$ for both detector limits $\pm s_o$ is an equal positive value. For maximum magnification, we set $|\tau(\Delta_{s,x}, \psi_d)| = \tilde{r}_0$ for both detector limits $\pm s_0$, which yields unique values for the detector tilt $\psi_d$ and the horizontal scanner displacement $\Delta_{s,x}$. Note that in tilted detector microtomography we always have $\tilde{r}_0 < r_0$ as opposed to the methods discussed in Section 3. FIG. 4 illustrates the impact of detector tilting on the resolution of the reconstructed images. Table 7 gives the rms-error and correlation of resolution enhanced images obtained through detector tilting, compared with a reconstruction from ideal fan beam projection data.

TABLE 7

Rms-error and correlation in reconstructions from resolution enhanced projection data using the method of tilted detectors.

| Magnification M | 1 | 2 | 5 | 10 | 32 |
|---|---|---|---|---|---|
| Tilt Angle $\psi$ | 0 deg | 60 deg | 78.5 deg | 84.3 deg | 88.2 deg |
| RMS Error | 0.14104 | 0.09995 | 0.06151 | 0.03935 | 0.03551 |
| Correlation | 0.86936 | 0.93746 | 0.97675 | 0.99050 | 0.99223 |

The trivial method of resolution enhancement in fan and cone beam geometry is close proximity microtomography, where by moving small objects closer to the point source the available fan spread is better utilized. However, there are some disadvantages to this approach. Close proximity microtomography reconstructs images with the standard fan beam algorithm as in (2). However, the standard fan beam convolution backprojection algorithm becomes increasingly sensitive to noise, aliasing, and other effects attributed to its discrete implementation as the region of reconstruction approaches the vicinity of the source location. This instability of the algorithm is due to the reciprocal weighting of the filtered projection data, i.e. the inversely to the source distance related ray energy in the backprojection. As shown in FIG. 3, with tilted detector microtomography the object may remain in its original position, where the resolution enhancement is achieved by stretching the projections over the tilted detector rather than by shifting the object towards the source. As shown in Table 8 and FIG. 5, with equivalent resolution enhancement tilted detector microscopy yields images of better contrast, signal-to-noise ratio, and shows less aliasing artifacts due to high-frequency pattern in the investigated object. Table 8 give the rms-error and correlation of resolution enhanced images obtained through tilting the detector, compared with a reconstruction from ideal fan beam data.

TABLE 8

Rms-error and correlation in reconstructions from resolution enhanced projection data using the method of close proximity and tilted detectors, compared with a reconstruction from ideal fan beam data. Projection magnification M = 32.

| Enhancement Method | Close Proximity | Tilted Detector |
|---|---|---|
| RMS Error | 0.07819 | 0.03551 |
| Correlation | 0.96393 | 0.99223 |

Another important aspect of microtomography is the performance in presence of penumbral broadening. Penumbral broadening is observed if a point source of finite size, or simplified and depicted in FIG. 19, if two horizontally displaced sources are used to generate fan beam projections. Penumbral broadening becomes a problem if low-quality point sources are employed for microtomography, such as low-cost laboratory sources. Here, the actual location of X-ray emission is an area of finite size, resulting in undesired penumbral blur in the projections. In fact, some application in microtomography achieve a reduction of penumbral broadening by placing the investigated object directly before the detector, and therefore altogether abandon the concept of close proximity tomography.

Figure 20A:
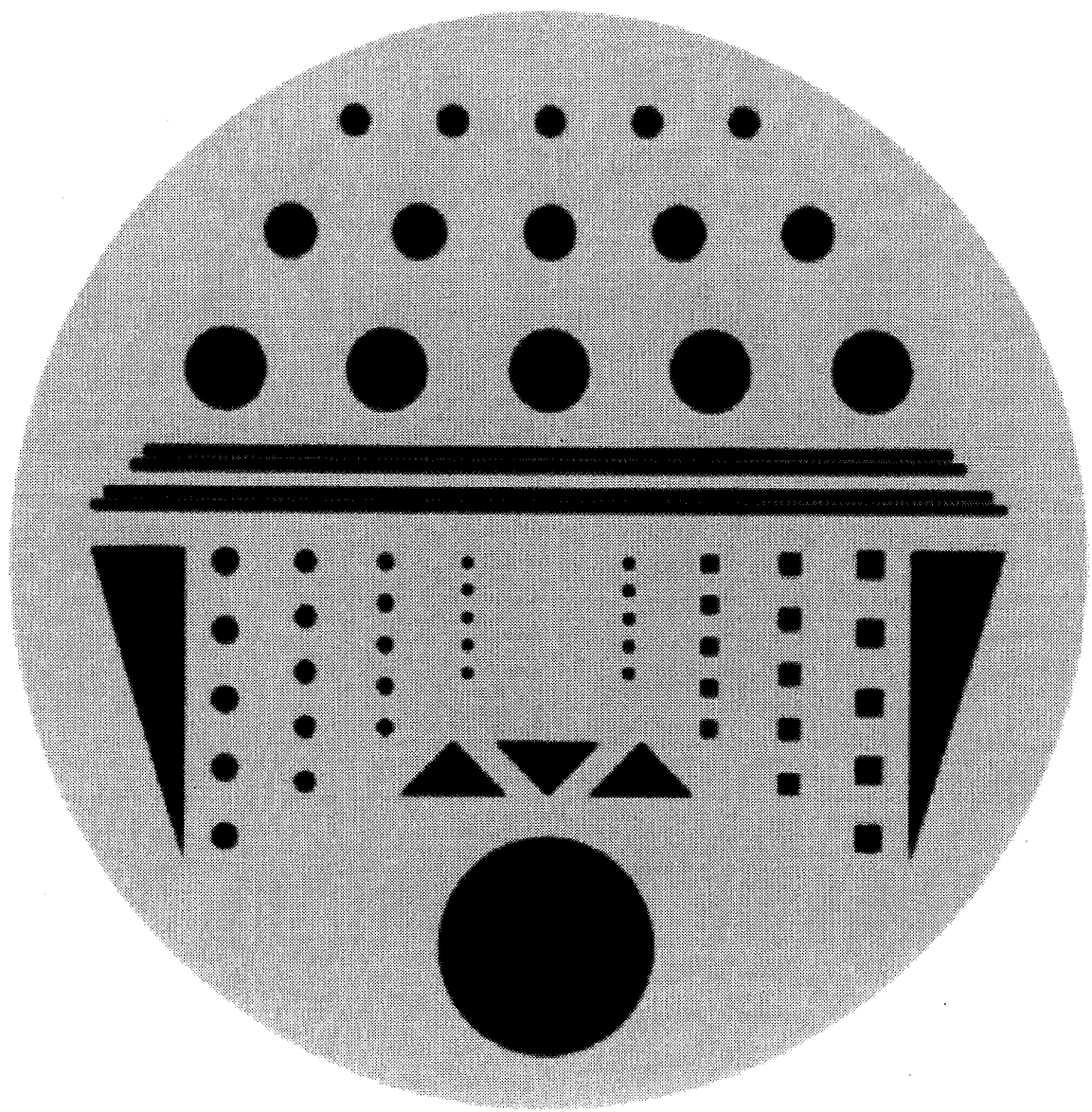
FIG. 20 shows penumbral broadening and blurring in close proximity and tilted detector microtomography. The amount of penumbral broadening is identical in all images. 20(a) shows a standard reconstructed image. 20(b) shows a standard reconstructed image with the object reduced 10 times. 20(c) shows a close proximity reconstructed image with the object reduced 10 times and the projections magnified 10 times. Here the object has been moved close to the source. 20(d) shows a tilted detector reconstructed image with the object reduced 10 times and the projections mag nified 10 times. Here the object has been moved close to the detector to reduce penumbral broadening.
Figure 20B:
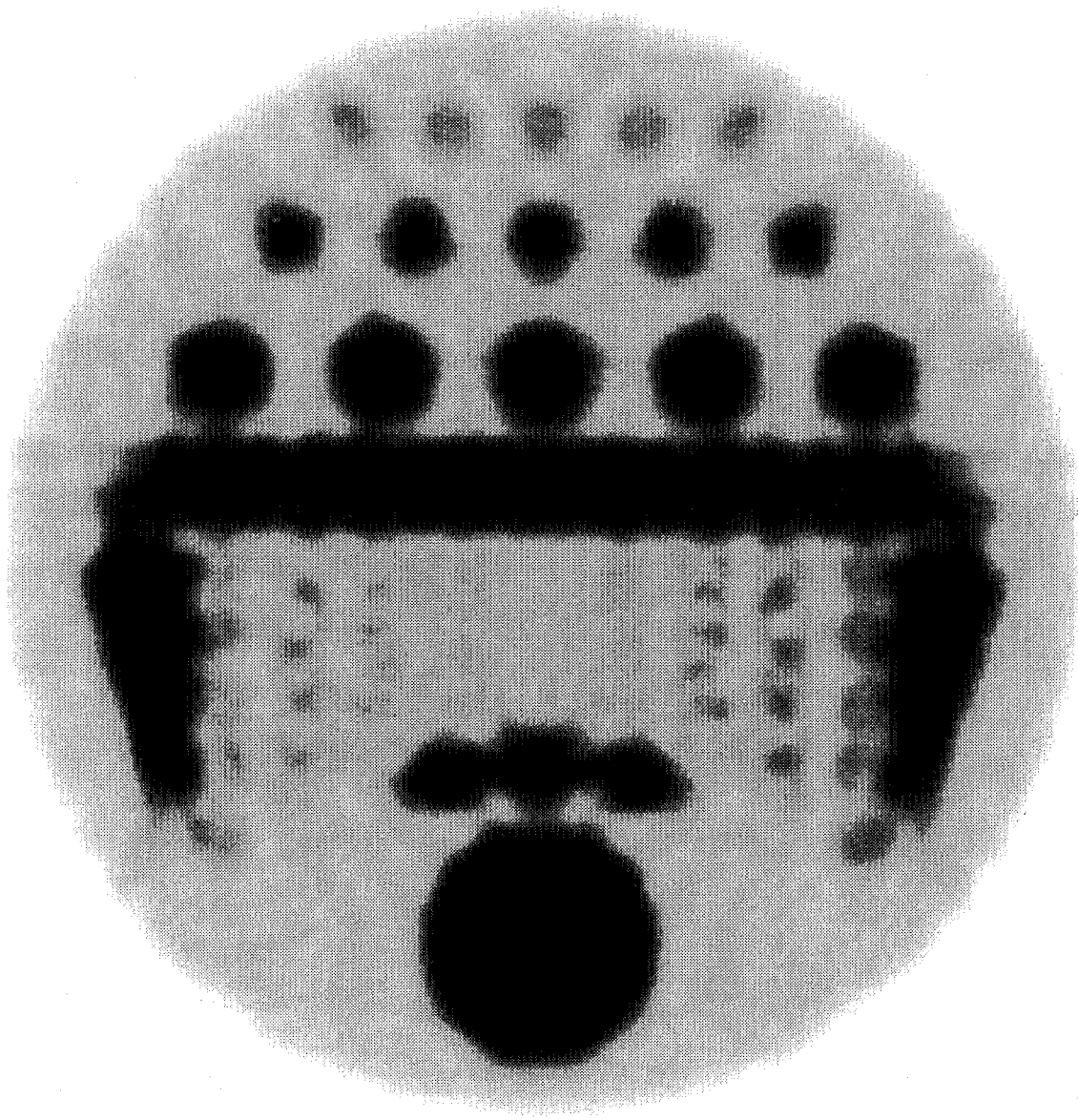
Figure 20C:
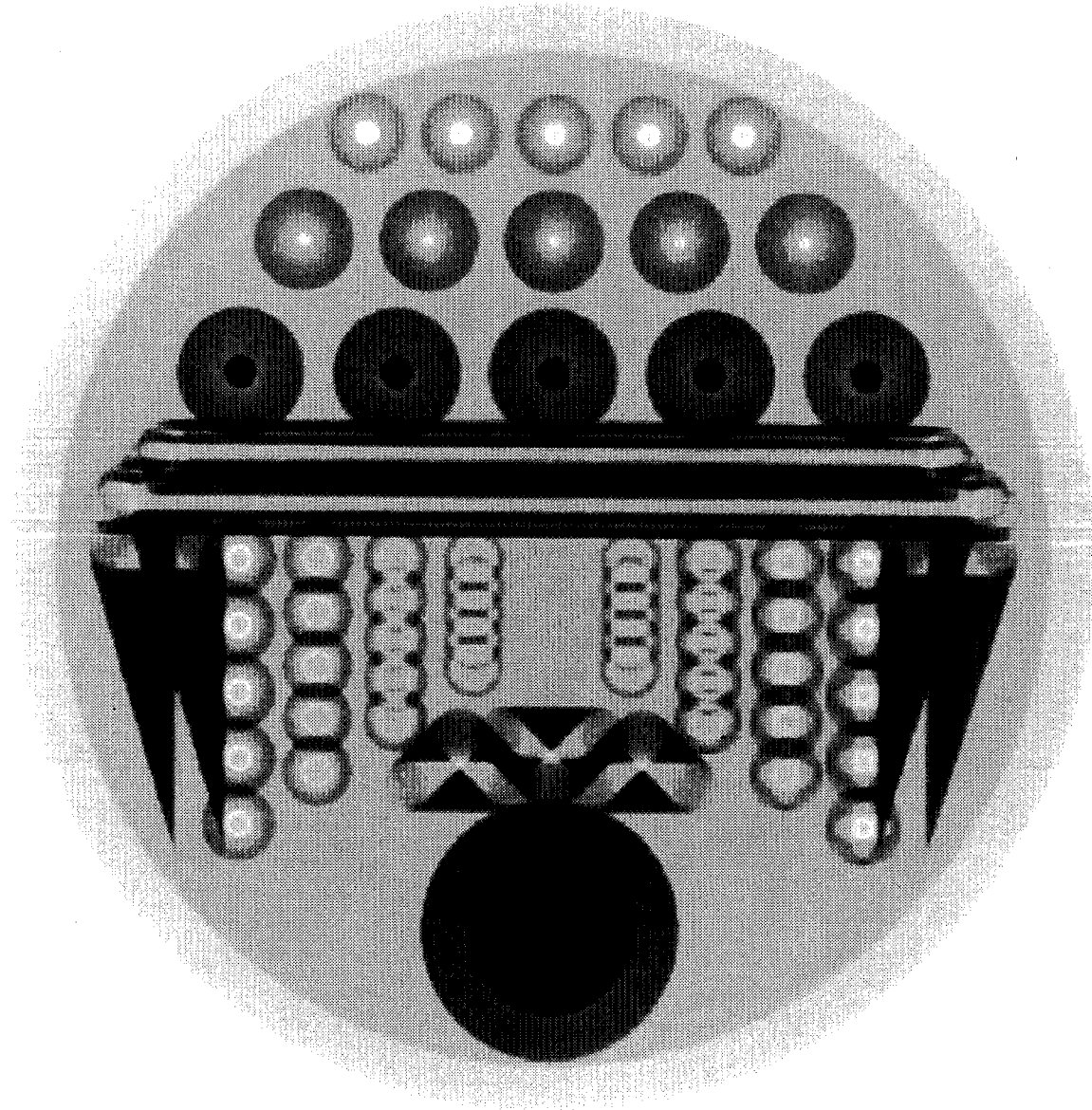
Figure 20D:
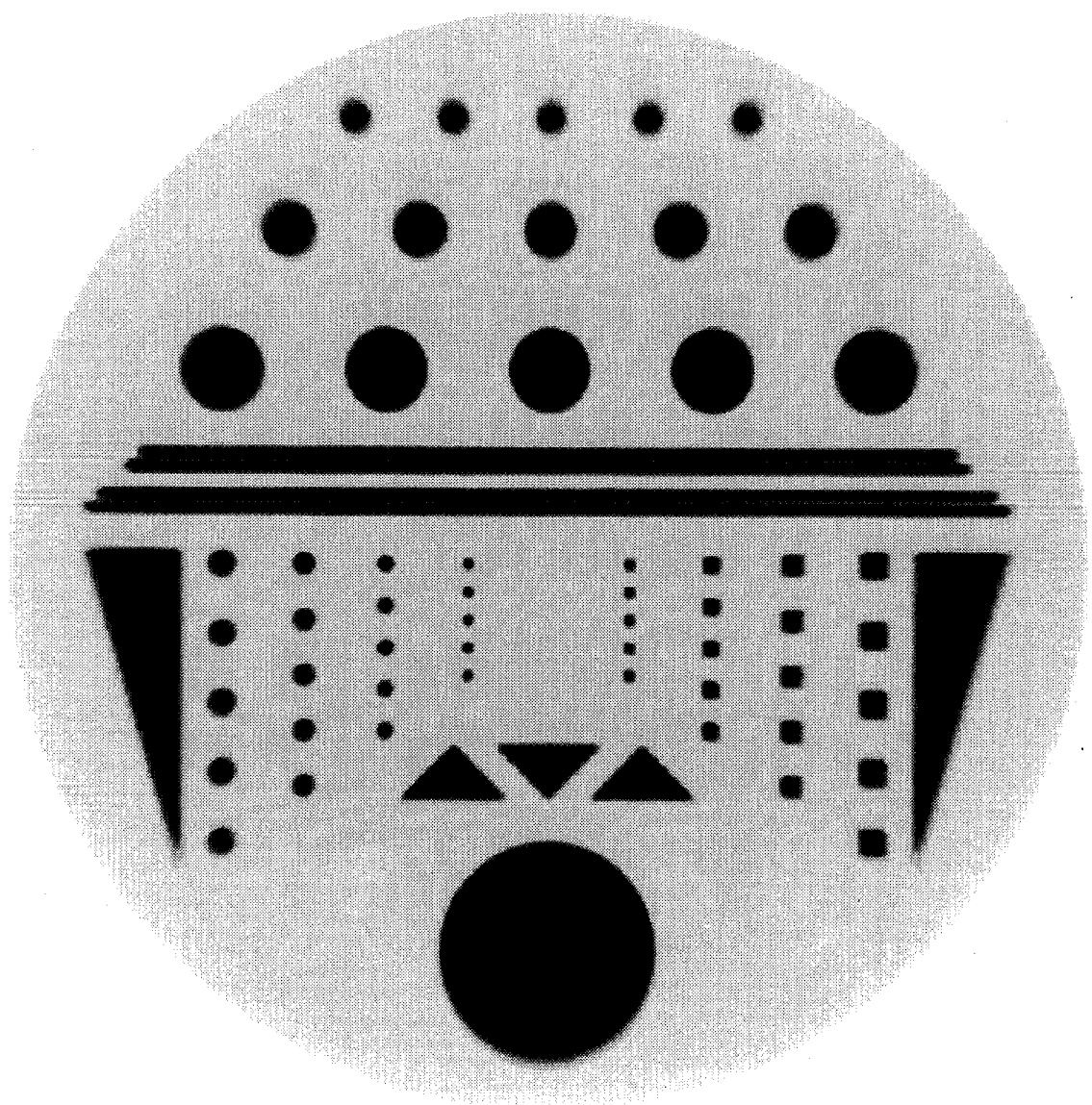

The blurring radius depends on the source width and the source-to-object distance d. Thus, moving the object closer to the source as suggested by close proximity microtomography cancels some of the enhancement in resolution due to the increasing penumbral blur. If the source width assumes the dimensions of the investigated object, then moving the object closer to the source does not have the desired effect and the projection resolution in fact decreases. However, here we assume that the source width is only a fraction of the object size. As illustrated in FIG. 19, tilted detector microtomography shows superior reconstruction performance in the presence of penumbral broadening, since it avoids an undesirable reduction of the source-to-object distance d. In fact, tilted detector microtomography in combination with positioning the investigated object close to the detector effectively enhances the resolution while reducing the blurring effect of the penumbral broadening due to finite size point sources. While close proximity microtomography provides the desired resolution enhancement, it also increases the penumbral broadening, as illustrated by FIG. 20c. The image in FIG. 20 obtained with tilted detector microtomography, on the other hand, is of high resolution while exhibiting only a minor blur. Table 9 gives the rms-error and correlation of images reconstructed with resolution enhancement due to close proximity and tilted detector microtomography in comparison to a reconstruction from ideal fan beam data.

TABLE 9

Rms-error and correlation in reconstructions from resolution enhanced projections in the presence of penumbral blurring, compared with a reconstruction from ideal fan beam data. The projection magnification is M = 10. The optimal case is associated with an object physically enlarged 10 times.

| Enhancement Method | Optimal | No Enhancement | Close Proximity | Tilted Detector |
|---|---|---|---|---|
| RMS Error | 0.03448 | 0.12105 | 0.20279 | 0.04862 |
| Correlation | 0.99267 | 0.90645 | 0.71908 | 0.98535 |

Section 5

We have derived an universal fan beam reconstruction algorithm based on the convolution backprojection method. The algorithm reconstructs from fan beam projections onto collinear detectors in arbitrary geometries. The algorithm accounts for horizontal and vertical source and detector displacements, such that in combination with one of the existing methods for precise determination of the various fan beam parameters directly from the projection data, it offers artifact-free and blur-free reconstruction with non-ideal scanners. We have shown that the algorithm is capable of reconstructing from non-redundant single sided projections, doubling the radius of the artifact-free zone at the expense of the image quality. Also, the algorithm can be applied to reconstruction from partially redundant projection data, where we combine the advantages of extending the artifact-free zone with high-quality reconstruction in the center portion of the investigated object. Tables 11 and 12 in the Appendix suggest that the image quality in reconstructions from partially or non-redundant projection data is substantially improved by application of smoothing during the reconstruction. We have applied the algorithm to the method of synthetic scanner arrays developed otherwise [M. Müller, G. R. Arce, and R. A. Blake Jr.; "Truncated Projection Artifacts and Reconstruction in Computerized Tomography", submitted to *IEEE Transactions on Image Processing.*; M. Müller and G. R. Arce, "The Cone Beam Algorithm and Synthetic Scanner Arrays in Three-Dimensional Computerized Tomography", technical report in the Department of Electrical Engineering at the university of Delaware, 1993.], where we reconstruct partial images immediately from the partial sets of projections and obtain the final result by superposition of the intermediate partial reconstructions. We have shown that the method of partial reconstructions does not work well with linear arrays due to the discontinuous Jacobian, but yields excellent results when applied to circular arrays. Compared to a resorting approach the new method results in images of higher resolution since we avoid interpolation and sampling operations inherent in the preprocessing approach.

The application of the algorithm to microtomography has led to a novel method of resolution enhancement, where we propose a detector tilt to stretch the projection of a small object over the entire detector width. As we have shown, the algorithm reconstructs from the enhanced projection data and yields images of excellent resolution, contrast, signal-to-noise ratio, and is less sensitive to aliasing artifacts due to the discrete implementation. However, while tilting the detector does stretch the projection over a larger portion of the detector, it also results in obliquely incident rays. To achieve a ten-fold resolution enhancement (M=10), for instance, the detector has to be tilted by $\psi_d$=84.2 deg. With standard phosphor-layer based intensifying screens tilting may pose a problem, since increased blurring due to a longer path of X-ray intersection through the screen tends to cancel the gain in resolution. However, application of the method of the present invention with low-energy X-rays and cellular phosphor quantum converters (e.g., phosphor arrays) improves the performance of tomographic scanners.

EXAMPLES

Below we provide tables giving the rms-error and correlation for all cases treated in the present application for reconstruction with applied smoothing, i.e. frequency domain application of a raised-cosine Hanning window.

TABLE 10

Rms-error and correlation in reconstructions from different types of center-displaced projections with smoothing applied during reconstruction.

| Displacement | Detector (FIG. 3a) | | Source (FIG. 3b) | | Scanner (FIG. 3c) | |
|---|---|---|---|---|---|---|
| Reconstruction | Standard | Universal | Standard | Universal | Standard | Universal |
| RMS-Error | 0.13476 | 0.00029 | 0.13621 | 0.00485 | 0.19649 | 0.00490 |
| Correlation | 0.87731 | 1.00000 | 0.87452 | 0.99985 | 0.72865 | 0.99985 |

TABLE 11

Rms-error and correlation in reconstructions from single-sided projections for low and high projection resolution with smoothing applied during reconstruction.

| Scanner Type | Type-I (FIG. 5a) | | Type-II (FIG. 5b) | |
|---|---|---|---|---|
| Resolution $N_\phi \times N_3$ | $301^2$ | $601^2$ | $301^2$ | $601^2$ |
| RMS-Error | 0.07957 | 0.07475 | 0.07714 | 0.15123 |
| Correlation | 0.96047 | 0.96621 | 0.96275 | 0.96976 |

TABLE 12

Rms-error and correlation in reconstructions from partially redundant projection data with smoothing applied during reconstruction.

| Redundancy | $\eta = 1.0$ | $\eta = 0.8$ | $\eta = 0.6$ | $\eta = 0.4$ | $\eta = 0.2$ | $\eta = 0.0$ |
|---|---|---|---|---|---|---|
| $\tilde{\tau}_o/\tau_o$ | 2.0 | 1.8 | 1.6 | 1.4 | 1.2 | 1.0 |
| $\tau_o'/\tau_o$ | 0.0 | 0.2 | 0.4 | 0.6 | 0.8 | 1.0 |
| RMS-Error | 0.07475 | 0.05526 | 0.04053 | 0.03087 | 0.01512 | 0.00000 |
| Correlation | 0.96621 | 0.98104 | 0.98967 | 0.99397 | 0.99855 | 1.00000 |

TABLE 13

Rms-error and correlation in images obtained through superposition of partial reconstructions from truncated projections for various fan spread angles with smoothing applied during reconstruction.

| Fan Spread Angle | 8.578 deg | 5.725 deg | 2.864 deg | 1.719 deg | 0.689 deg |
|---|---|---|---|---|---|
| RMS-error | 0.35434 | 0.25361 | 0.10819 | 0.05925 | 0.05348 |
| Correlation | 0.62525 | 0.74547 | 0.93373 | 0.97871 | 0.98252 |

TABLE 14

Rms-error and correlation coefficient in reconstructions from resolution enhanced projection data using the method of tilted detectors compared with a reconstruction from ideal fan beam data with smoothing applied during reconstruction.

| Magnification M | 1 | 2 | 5 | 10 | 32 |
|---|---|---|---|---|---|
| Tilt Angle $\psi$ | 0 deg | 60 deg | 78.5 deg | 84.3 deg | 88.2 deg |
| RMS Error | 0.15185 | 0.12145 | 0.07353 | 0.04144 | 0.01479 |

TABLE 14-continued

Rms-error and correlation coefficient in reconstructions from resolution enhanced projection data using the method of tilted detectors compared with a reconstruction from ideal fan beam data with smoothing applied during reconstruction.

| Magnification M | 1 | 2 | 5 | 10 | 32 |
|---|---|---|---|---|---|
| Tilt Angle $\psi$ | 0 deg | 60 deg | 78.5 deg | 84.3 deg | 88.2 deg |
| Correlation | 0.84304 | 0.90305 | 0.96605 | 0.98929 | 0.99862 |

TABLE 15

Rms-error and correlation coefficient in reconstructions from resolution enhanced projection data using the method of close proximity and tilted detectors, compared with a reconstruction from ideal fan beam data Projection Magnification M = 32. Smoothing applied during reconstruction

| Enhancement Method | Close Proximity | Tilted Detector |
|---|---|---|
| RMS Error | 0.04845 | 0.01479 |
| Correlation | 0.98543 | 0.99862 |

TABLE 16

RMS-error and correlation coefficient in reconstructions from resolution enhanced projections in the presence of penumbral blurring compared with a reconstruction from ideal fan beam data. The projection magnification is M = 10. The optimal case is associated with an object physically enlarged 10 times. Smoothing applied during reconstruction.

| Enhancement Method | Optimal | No Enhancement | Close Proximity | Tilted Detector |
|---|---|---|---|---|
| RMS Error | 0.01124 | 0.12093 | 0.19262 | 0.02783 |
| Correlation | 0.99921 | 0.90420 | 0.73963 | 0.99511 |

TABLE 17

Rms-error and correlation in images obtained with a circular fan beam scanner array with a spread angle of 8.578 deg. superposition of partial reconstructions. Smoothing applied during reconstruction.

| Method | Preprocessing/ Resorting | | Partial Reconstruction | |
|---|---|---|---|---|
| Resolution $N_\phi \times N_3$ | $201^2$ | $601^2$ | $201^2$ | $601^2$ |
| RMS-Error | 0.04081 | 0.03210 | 0.05679 | 0.03349 |
| Correlation | 0.98959 | 0.99361 | 0.98013 | 0.99328 |

Therefore, the preferred embodiments of the present invention are:

(1) A setup for performing computerized tomography comprising:

at least one radiation source which generates a fan-shaped radiation beam lying in a fan-plane;

a radiation receiver;

a turntable located between the at least one radiation source and the radiation receiver which holds the object to be scanned by the setup;

means for tilting the radiation receiver about a tilt axis which extends perpendicularly to the fan-plane of the radiation beam; and means for shifting the radiation receiver so that the tilt axis of the radiation receiver is horizontally displaced from the central ray of the fan-shaped radiation beam.

(2) A setup for performing computerized tomography comprising:

at least one radiation source which generates a fan-shaped radiation beam lying in a fan-plane;

a radiation receiver which receives the radiation generated by the at least one radiation source and converts it into electrical energy;

a turntable located between the at least one radiation source and the radiation receiver which holds the object to be scanned by the setup;

a first means for converting the electrical energy provided from the radiation receiver into a form which can be viewed on a video display unit;

a second means for tilting the radiation receiver about a tilt axis which extends perpendicularly to the fan-plane of the radiation beam; and a third means for shifting the radiation receiver so that the tilt axis of the radiation receiver is horizontally displaced from the center of the fan-shaped radiation beam.

(3) The setup of (2), wherein said first means includes a computer.

(4) The setup of (2), wherein said second and third means consist of one piece of equipment that can both tilt and horizontally shift the radiation receiver.

(5) The setup of (2), wherein the radiation receiver comprises at least one detector.

(6) The setup of (1), wherein the means for tilting the radiation receiver and the means for shifting the radiation receiver consist of one piece of equipment that can both tilt and horizontally shift the radiation receiver.

(7) The setup of (1), wherein the radiation receiver comprises at least one detector.

(8) A method of performing computerized tomography which comprises:

scanning an object located between a radiation source and a radiation receiver with a fan-shaped radiation beam which, after passing through the object hits the radiation receiver;

tilting the radiation receiver about a tilt axis which extends perpendicularly to the fan-plane of the radiation beam; and shifting the radiation receiver so that the tilt axis of the radiation receiver is horizontally displaced from the center of the fan-shaped radiation beam;

wherein the tilting and shifting of the radiation receiver is performed before or during said scanning.

(9) The method of (8), wherein during the scanning step, the radiation receiver converts the radiation received from said radiation source into electrical energy which is then converted by a computer into a form which can be viewed on a video display unit.

In each of these preferred embodiments, the electrical energy from the radiation receiver (which usually comprises at least one detector) is passed through a computer which uses the universal fan beam algorithm (described above) to reconstruct the partial projection data (which is in the form of electrical energy from the radiation receiver) into a complete image which is free of blurring and other related artifacts. The tilting of the radiation receiver permits the projection of the object being scanned to be spread over a larger portion of the radiation receiver than would be obtained by having the radiation receiver in its normal (non-tilted) position and thus provides greater resolution in the final image. Moreover, the combination of tilting and shifting the radiation receiver provides the maximum utilization of the radiation receiver by eliminating the asymmetries in the effective range of the receiver that result when the receiver is only tilted.

While the invention has been particularly shown and described with reference to preferred embodiments thereof, it will be understood by those skilled in the art that various changes in form and details may be made without departing from the spirit and scope of the invention as defined in the appended claims.

What is claimed is:

1. A setup for performing computerized tomography comprising:

at least one radiation source which generates a fan-shaped radiation beam lying in a fan-plane;

a radiation receiver;

a turntable located between the at least one radiation source and the radiation receiver;

means for tilting the radiation receiver about a tilt axis which extends perpendicularly to the fan-plane of the radiation beam; and means for shifting the radiation receiver so that the tilt axis of the radiation receiver is horizontally displaced from the central ray of the fan-shaped radiation beam.

2. A setup for performing computerized tomography comprising:

at least one radiation source which generates a fan-shaped radiation beam lying in a fan-plane;

a radiation receiver which receives the radiation generated by the at least one radiation source and converts it into electrical energy;

a turntable located between the at least one radiation source and the radiation receiver;

a first means for converting the electrical energy provided from the radiation receiver into a form which can be viewed on a video display unit;

a second means for tilting the radiation receiver about a tilt axis which extends perpendicularly to the fan-plane of the radiation beam; and a third means for shifting the radiation receiver so that the tilt axis of the radiation receiver is horizontally displaced from the center of the fan-shaped radiation beam.

3. The setup of claim 2, wherein said first means includes a computer.

4. The setup of claim 2, wherein said second and third means consist of one piece of equipment that can both tilt and horizontally shift the radiation receiver.

5. The setup of claim 2, wherein the radiation receiver comprises at least one detector.

6. The setup of claim 1, wherein the means for tilting the radiation receiver and the means for shifting the radiation receiver consist of one piece of equipment that can both tilt and horizontally shift the radiation receiver.

7. The setup of claim 1, wherein the radiation receiver comprises at least one detector.

8. A method of performing computerized tomography which comprises:

scanning an object located between a radiation source and a radiation receiver with a fan-shaped radiation beam which, after passing through the object hits the radiation receiver;

tilting the radiation receiver about a tilt axis which extends perpendicularly to the fan-plane of the radiation beam; and shifting the radiation receiver so that the tilt axis of the radiation receiver is horizontally displaced from the center of the fan-shaped radiation beam;

wherein the tilting and shifting of the radiation receiver is performed before or during said scanning.

9. The method of claim 8, wherein during the scanning steps the radiation receiver converts the radiation received from said radiation source into electrical energy which is then converted by a computer into a form which can be viewed on a video display unit.

* * * * *

UNITED STATES PATENT AND TRADEMARK OFFICE
CERTIFICATE OF CORRECTION

PATENT NO. : 5,493,593
DATED : Feb. 20, 1996
INVENTOR(S) : Muller, et al

It is certified that error appears in the above-indentified patent and that said Letters Patent is hereby corrected as shown below:

In Column 30, line 36, "steps" should be --step,--.

Signed and Sealed this

Tenth Day of September, 1996

Attest:

BRUCE LEHMAN

Attesting Officer    Commissioner of Patents and Trademarks